US008604281B2

(12) United States Patent
Werner et al.

(10) Patent No.: US 8,604,281 B2
(45) Date of Patent: *Dec. 10, 2013

(54) TRANSGENIC PLANTS WITH CONTROLLED DISTRIBUTION OF A TRAIT TO PROGENY

(75) Inventors: Stefan Werner, Halle (DE); Anatoly Giritch, Halle (DE); Serik Eliby, Halle (DE); Sylvestre Marillonnet, Halle (DE); Victor Klimyuk, Halle (DE); Yuri Gleba, Halle (DE)

(73) Assignee: Bayer CropScience NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/470,812

(22) Filed: May 14, 2012

(65) Prior Publication Data

US 2013/0024986 A1 Jan. 24, 2013

Related U.S. Application Data

(63) Continuation of application No. 12/621,765, filed on Nov. 19, 2009, now Pat. No. 8,193,410, which is a continuation of application No. 10/514,905, filed as application No. PCT/EP03/02986 on Mar. 21, 2003, now Pat. No. 7,642,404.

(30) Foreign Application Priority Data

May 31, 2002 (DE) .................................. 102 24 214
Jun. 5, 2002 (DE) .................................. 102 24 980

(51) Int. Cl.
*C12N 15/82* (2006.01)
*C12N 15/31* (2006.01)
*C12N 15/62* (2006.01)
*C12N 9/22* (2006.01)
*A01H 1/02* (2006.01)
*A01H 1/04* (2006.01)
*A01H 5/00* (2006.01)
*A01H 5/10* (2006.01)

(52) U.S. Cl.
CPC ........ *C12N 15/8274* (2013.01); *C12N 15/8265* (2013.01); *C12N 15/8289* (2013.01); *C12N 15/8213* (2013.01); *C12N 15/8231* (2013.01)
USPC ........... 800/300; 800/260; 800/274; 800/278; 800/288; 800/291; 800/303; 800/287; 435/69.1; 435/69.7; 435/69.8; 435/199; 435/462; 435/463; 435/468

(58) Field of Classification Search
None
See application file for complete search history.

(56) References Cited

U.S. PATENT DOCUMENTS

| 6,015,794 A | 1/2000 | Haseloff et al. |
| 6,392,119 B1 | 5/2002 | Gutterson et al. |
| 6,852,911 B1 | 2/2005 | Izhar |
| 7,026,526 B2 | 4/2006 | Snell |

FOREIGN PATENT DOCUMENTS

| WO | 92/13090 A1 | 8/1992 |
| WO | 00/52146 A2 | 9/2000 |
| WO | 00/71701 A1 | 11/2000 |
| WO | 01/59091 A2 | 8/2001 |
| WO | 02/096192 A2 | 12/2002 |

OTHER PUBLICATIONS

Groth et al. Journal of Molecular Biology 335(3): 667-678 (Jan. 2003).
Shingledecker et al., Gene 207: 187-195 (1998).
Chong et al. The Journal of Biological Chemistry 271(36): 22159-22168 (1996).
Ayre, B., et al., "Design of Highly Specific Cytotoxins by Using Trans-splicing Ribozxymes," Proc. Natl. Acad. Sci. USA, 1999, pp. 3507-3512, vol. 17.
Burgess, D., et al., "A novel, two-component system for cell lethality and its use in engineering nuclear male-sterility in plants," The Plant Journal, 2002, pp. 113-125, vol. 31(1).
Chen, et al., "Herbicide resistance from a divided EPSPS protein: The split Synechocystic DnaE intein as an in vivo affinity domain" Gene, 2001, pp. 39-48, vol. 263(1-2).
Gils, M., et al., "A novel hybrid seed system for plants" Plant Biotechnology Journal, 2008, pp. 226-235, vol. 6(3).
Goldman, et al., "Female sterile tobacco plants are produced by stigma-specific cell ablation" The EMBO Journal, 1994, pp. 2976-2984, vol. 13(13).
Kandasamy, et al., "Ablation of Papillar Cell Function in Brassica Flowers Results in the Loss of Stigma Receptivity to Pollination" The Plant Cell, 1993, pp. 263-275, vol. 5(3).
Li, B., et al. "Human Acyl-CoA:Cholesterol Acyltransferase-1 (ACAT-1) Gene Organization and Evidence That the 4.3-Kilobase ACAT-1 mRNA is Produced from Two Different Chromosomes" The Journal of Biological Chemistry, 1999, pp. 11060-11070, vol. 274(16).

(Continued)

*Primary Examiner* — David T Fox
(74) *Attorney, Agent, or Firm* — Lerner, David, Littenberg, Krumholz & Mentlik, LLP

(57) ABSTRACT

A process of producing transgenic multi-cellular plants or parts thereof expressing a trait of interest that has a controlled distribution of said trait to progeny, comprising (i) producing a first plant or a cell thereof having in a first locus of a nuclear chromosome a first heterologous nucleotide sequence comprising a first fragment of a nucleotide sequence encoding said trait of interest, (ii) producing a second plant or a cell thereof having in a second locus of a nuclear chromosome homologous to said nuclear chromosome of step (i), a second heterologous nucleotide sequence comprising a second fragment of the nucleotide sequence encoding said trait of interest, and (iii) hybridising said first and said second plants or cells thereof to generate progeny exhibiting said functional trait of interest. Also disclosed is a process of producing hybrid seeds for agriculture.

23 Claims, 29 Drawing Sheets

(56) References Cited

OTHER PUBLICATIONS

McCreath, et al., "Production of gene-targeted sheep by nuclear transfer from cultured somatic cells," Nature, 2000, pp. 1066-1069 +1 (Erratum), vol. 405.

Pelletier, et al., "Plant protoplast fusion and somatic plant cell genetics" Physiol. Veg., 1984, pp. 377-399, vol. 22(3).

Sessa et al., "The expression of an abundant transmitting tract-specific endoglucanase (Sp41) is promoter-dependent and not essential for the reproductive physiology of tobacco" Plant Molecular Biology, 1995, pp. 969-982, vol. 29.

Sun, et al. "Protein trans-Splicing to Produce Herbicide-Resistant Acetolactate Synthase" Applied and Environmental Microbioklogy, 2001, pp. 1025-1029, vol. 67(3).

Thomson, J., et al., "Artificial Gene-clusters Engineered into Plants Using a Vector System Based on Intron- and Intein-Encoded Endonucleases," In Vitro Cell. Dev. Biol., 2002, pp. 537-542, vol. 38, Society for In Vitro Biology.

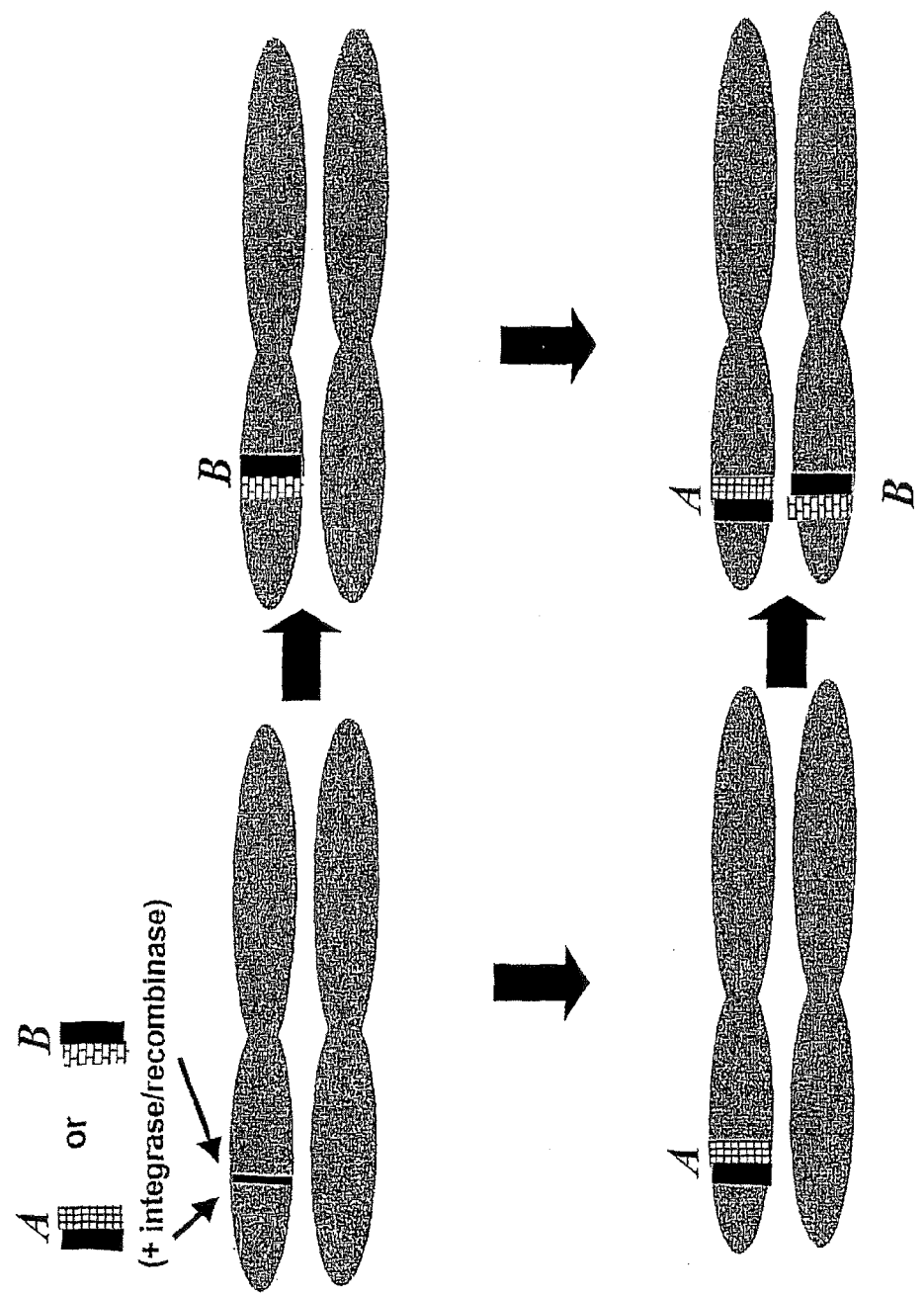

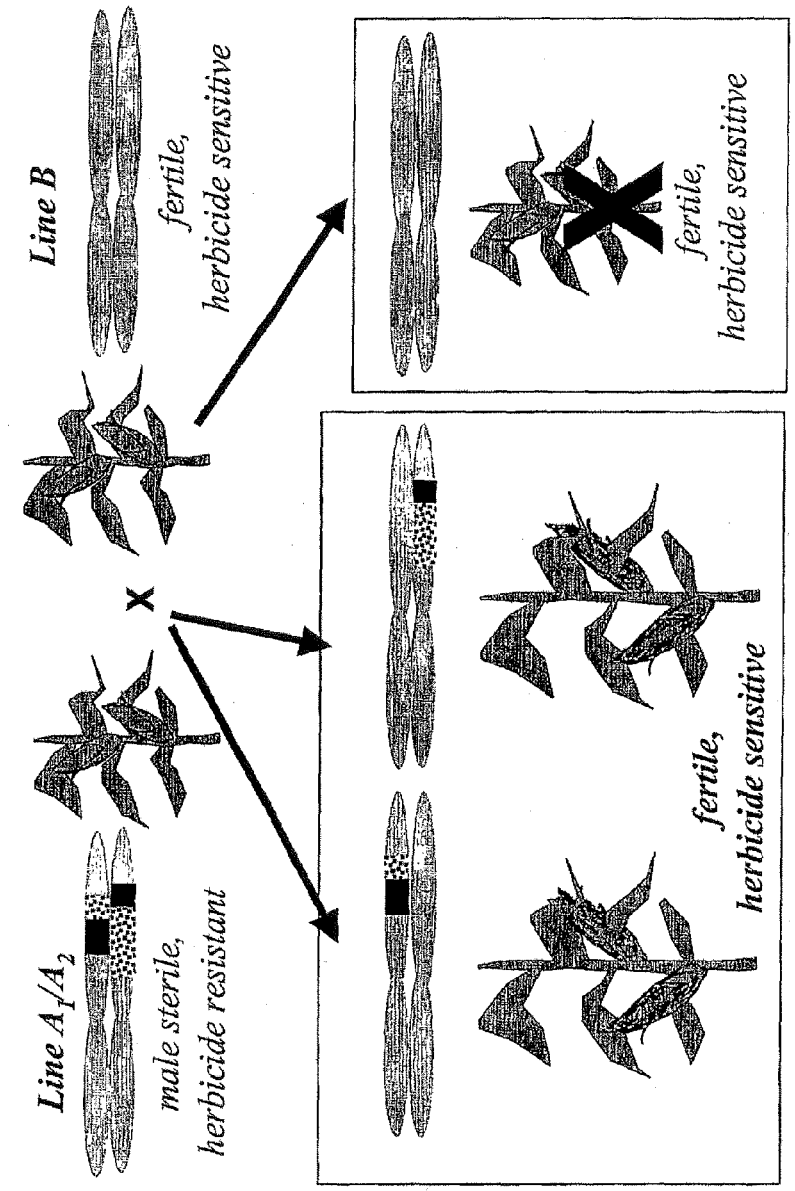

TRANSGENIC PLANTS WITH CONTROLLED DISTRIBUTION OF A TRAIT TO PROGENY

CROSS-REFERENCE TO RELATED APPLICATIONS

The present application is a continuation of U.S. patent application Ser. No. 12/621,765, filed on Nov. 19, 2009, now U.S. Pat. No. 8,193,410, which application is a continuation of U.S. application Ser. No. 10/514,905, filed Nov. 17, 2004, now U.S. Pat. No. 7,642,404, which is a national phase entry under 35 U.S.C. §371 of International Application PCT/EP2003/02986, filed Mar. 21, 2003, which claims the priority from DE 102 24 214.3, filed May 31, 2002 and DE 102 24 980.6, filed Jun. 5, 2002, all of which are incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 30, 2012, is named PCT-12195-3 ST25.txt and is 13.5 kilobytes in size.

FIELD OF THE INVENTION

The present invention relates to a process of producing hybrid seeds. The invention also relates to a process of producing a transgenic multicellular plant organism expressing a trait of interest and having a controlled distribution of said trait to progeny or to other organisms. The invention also relates to a process of producing a transgenic multicellular plant organism expressing two traits of interest, whereby said traits have a controlled distribution to progeny. Preferably, one of said traits is male sterility. Moreover, the invention relates to a process of producing hybrid seeds, notably for agricultural purposes. The invention further relates to a plant expressing a trait, whereby the distribution of said trait to progeny is controlled, i.e., the probability of transferring said trait to illicit progeny, notably by cross-pollination, is very low.

BACKGROUND OF THE INVENTION

The commercial use of genetically engineered crop species has caused concerns about the possible transfer of transgenes and traits encoded by transgenes from genetically modified plants (GM plants) into landraces, wild relative or other non-GM plant varieties or related crop species (Ellstrand, N.C., 2001, *Plant Physiol.* 125, 1543-1545; "Quist & Chapela, 2001, *Nature,* 414, 541-543), which could change the ecological balance in the affected ecosystems or lead to other, first of all, socioeconomic problems. Additionally, there is a certain fear that transgenes, especially antibiotic resistance genes used as transformation markers, can escape, through so-called horizontal transfer, into surrounding microorganisms (Chiter et al. 2000, *FEBS Lett.,* 481, 164-168), thus modifying the microflora in an undesirable way.

Although many of these worries are not well justified scientifically (Christou, P., 2002, *Transgenic Res.,* 11, iii-v), the creation of safe and controlled transgene management systems is highly desirable, as it might prevent potential problems in the future and shall help to protect the germplasm of existing plant species in the most efficient way. In addition, there are problems caused by contamination of organically grown crops or non-GM crops with transgenic cultivars. This has a serious impact on the marketing of transgenic as well as non-transgenic crops, an issue which cannot be ignored by producers.

Unlike other products generated by humans, products created by biotechnology are potentially self-replicating machines. Therefore, any transgenic material created by current technology and released into the environment has a potential of persisting there for a very long time. Common practice of plant genetic engineering is based on the use of expression cassettes and vectors that contain continuous coding sequence for the gene of interest. Such expression cassettes are integrated into a host chromosome and upon hybridization or another genetic information exchange between a GM plant and another organism, whether licit or illicit, the expression cassette is transmitted with a high probability to the progeny or another recipient as a functional transcriptional unit.

WO00/52146 describes general ideas for encrypting a trait of interest by splitting gene(s) in two or more fragments and rejoining the fragments by trans-splicing after mating parental organisms, whereby the parental organisms provide said fragments. WO00/52146 does not go beyond general ideas. It does not contain an enabling disclosure on how these ideas can be reduced to practice. Notably, it does not contain an example. WO00/71701 describes assembly of a functional protein by intein-mediated protein trans-splicing/interaction for improving containment of a transgene encoding said protein. WO00/71701 does not describe bringing together fragments of a protein by mating parent organisms. Further, the frequency of transmission of transgene according to WO00/71701 is not sufficiently low for large scale applications like agriculture, notably when a transgene provides a selective advantage.

WO0116287 relates to the creation of allelic position for transgenes, whose expression determines a phenotype, with the aim that the transgenes segregate to different gametes. This patent application does not address the problem of controlling movement of transgenes, but rather trait generation, specifically male-sterility, encoded by at least two transgenes. Further, it does not mention intein-mediated trans-splicing. Moreover, this application does not describe control over trait movement by splitting a trait-encoding gene in two or more fragments.

Trait assembly from parts encoding the trait is not of high value without knowing how to achieve the most favorable positions of the encoding fragments in practically the most feasible way, in order to provide the strictest control over undesired transmission of said trait. For large scale applications like for agriculture, biological safety requires that undesired transmission of a transgene is reduced to a frequency of practically zero.

Crop plants expressing as a trait of interest male or female sterility are widely used for hybrid seed production. Hybrid crops have on average 20% yield advantage over inbred varieties and production of hybrid seeds is a large industry. Many different technologies are used to produce hybrid seeds (for review see: Perez-Prat E. & van Lookeren Campagne, M M, 2002, *Trends Plant Sci.,* 7 199-202). These technologies can be conditionally divided into at least four groups according to the pollination control mechanism: mechanical, chemical, genetic and transgenic. However, one critical requirement is common for all these technologies: ideally, a 100% male sterile line should be used for the hybridization process and 100% male fertility restoration in $F_1$ progeny should be achieved. Such stringent requirements are absolutely necessary for producing hybrid seeds free of contamination with selfed seeds.

The current methods of hybrid seed production are unsatisfactory in the above respect. These processes are either expensive, as in the case of mechanical de-tasselling (castration) of corn, or "leaky" as in the case of genetic approaches or both as in the case of chemical treatment-based method (e.g., U.S. Pat. No. 4,569,688).

Genetic approaches preferably include the use of lines with cytoplasmic male sterility (CMS) mutants and fertility restorers (e.g., WO02098209). Transgenic approaches use predominantly plants with genetically engineered nuclear male sterility (NMS) or CMS and fertility restoration in $F_1$ progeny (WO8910396; U.S. Pat. No. 5,530,191; U.S. Pat. No. 6,255,564; WO9832325; WO9201799; U.S. Pat. No. 6,392,1191; WO0116287). These approaches also require the use of a so-called maintainer line in order to propagate and maintain the male-sterile line.

The transgenic systems built on one transgene providing for male sterility and another transgene carrying the function of restoring male fertility (e.g., U.S. Pat. No. 6,255,5640) guarantee neither complete restoration of male fertility in hybrid progeny nor complete elimination of potentially negative effects of the transgene providing for male sterility on the general health of said progeny. In other words these systems are leaky. In addition, none of the systems mentioned above offers a convenient way of producing and maintaining the male-sterile line. This is an important element of any genetically engineered system for hybrid seed production, as the successful application of such a system for large-scale production depends on whether the male-sterile female parent line can be propagated in an economical and efficient way. In other words, currently there is no universal, reliable and economical system for hybrid seed production, which integrates all requirements necessary for maintenance of the original lines, hybridization process, restoration of male fertility in hybrid progeny and at the same time has high biological safety parameters, e.g., provides for tight control over transgene segregation. A general scheme of hybrid seeds production using currently existing genetic/transgenic approaches is shown in FIG. 12.

In the present invention, we describe a new process of producing hybrid seeds (FIG. 13) which has all necessary characteristics to match the requirements of an ideal hybridization system. A comparison of the hybrid seed production system of the invention with prior art methods is presented in Table 1.

It is therefore an object of the invention to provide a process of producing a transgenic plant expressing a trait of interest, notably male sterility, whereby distribution of said trait to progeny is strictly controlled and occurs with low probability.

It is a further object of the invention to provide a process of producing a biologically safe transgenic plant, notably a male sterile plant, that expresses a trait of interest, whereby gene fragments encoding said trait are positioned such that undesired transmission of said trait occurs with low probability.

It is a further object of the invention to provide a process of positioning transgenic DNA sequences on homologous chromosomes, notably in the same locus of homologous chromosomes of a multi-cellular organism.

It is also an object of the invention to provide a process of producing a male sterile plant line.

It is another object of the invention to provide a universal and environmentally safe process of producing hybrid seeds using a sterile plant line, whereby complete fertility restoration occurs in said hybrid seeds.

GENERAL DESCRIPTION OF THE INVENTION

The invention provides a process of producing a transgenic multi-cellular plant organism or parts thereof expressing a trait of interest and having a controlled distribution of said trait to progeny, wherein said process comprises (i) producing a first plant or a cell thereof having in a first locus of a nuclear chromosome a first heterologous nucleotide sequence comprising a first fragment of a nucleotide sequence encoding said trait of interest, (ii) producing a second plant or a cell thereof having in a second locus of a nuclear chromosome homologous to said nuclear chromosome of step (i), a second heterologous nucleotide sequence comprising a second fragment of the nucleotide sequence encoding said trait of interest, and (iii hybridising said first and said second plant or cells thereof to generate progeny exhibiting said functional trait of interest due to binding between a protein or polypeptide encoded by said first heterologous nucleotide sequence and a protein or polypeptide encoded by said second heterologous nucleotide sequence. Said binding preferably involve protein trans-splicing.

Said multi-cellular plant organisms or said parts produced by the above process may express two traits of interest, a trait (1) and a trait (2), both traits having a controlled distribution to progeny.

The inventors of this invention have developed for the first time a method of rendering transgenic plants environmentally safe in that the transgene or a trait of interest expressed by said plant has a controlled distribution to progeny of said plant. The invention solves a major problem of biotechnology, notably of plant biotechnology, since transfer of a transgene from a GM plant to other organisms can now be effectively controlled and limited. Transfer of a transgene to other organisms includes transfer to sexual progeny by cross-pollination as well as lateral gene transfer. The above processes make obtainable genetically modified multi-cellular plants with a controlled containment of a trait of interest.

In an important embodiment, said trait of interest is male or female sterility, preferably male sterility. In this case, the transgenic multi-cellular plant organism of the invention may be used for hybrid seed production by crossing with another plant that is male fertile or female fertile, respectively. The hybrid seeds produced using the transgenic multi-cellular plant of the invention may be 100% fertile due to a controlled distribution of the sterility trait to progeny. In a particularly preferred embodiment, said transgenic multi-cellular plant of the invention may express two traits of interest, a male sterility trait and a herbicide resistance trait, what makes amenable a novel process of producing hybrid seeds with several advantages over prior art processes (see below).

In the process of the invention, the nucleotide sequence encoding (or involved in) said trait is split into two or more fragments. Preferably, said nucleotide sequence is split into two fragments of said nucleotide sequence, thus obtaining a 5' and a 3' part of the nucleotide sequence. Said 5' part corresponds essentially to said first fragment. Said 3' part corresponds essentially to said second fragment. Said nucleotide sequence is typically a coding sequence (or an open reading frame) of a protein involved in said trait. However, said nucleotide sequence may contain one or more introns. To obtain said fragments, said nucleotide sequence is preferably split such that each obtained fragment, upon expression, is incapable of generating said trait in the absence of the other fragment. Each fragment contains a sequence portion necessary for the function of the protein involved in said trait. For example, if said protein involved in said trait is an enzyme, each fragment preferably contains amino acids necessary for catalysis or substrate binding of the enzyme. A protein involved or encoding a trait may be split into said fragments in many different ways provided that expression of said trait requires all said fragments and binding thereof to each other. Structural and functional information known about the protein involved in said trait may be helpful for finding a suitable splitting site of said nucleotide sequence. In any case, one can easily test experimentally whether a fragment generated by splitting a nucleotide sequence at a randomly chosen site is capable of expressing a trait encoded by said nucleotide sequence. The following description focuses on the preferred embodiment, wherein said nucleotide sequence encoding said trait is split into two fragments.

Expression of said trait requires the presence of both said fragments in the same plant, preferably in the same cells thereof. Expression of said trait further requires transcription and translation of said first and said second fragment and binding of the translation products of said fragments to each other with or without peptide bond formation. Preferably, said binding involves peptide bond formation between said fragments.

The first fragment is incorporated into a first heterologous nucleotide sequence, the second fragment is incorporated into a second heterologous nucleotide sequence. Preferably, said heterologous nucleotide sequences are DNA sequences.

Preferably, said first and said second heterologous nucleotide sequence further codes for a first and a second binding polypeptide, respectively, that renders said polypeptides encoded by said first and said second heterologous nucleotide sequences capable of said binding. Each binding polypeptides is preferably expressed as a protein fusion with the polypeptide encoded by said first or said second fragment.

Said polypeptide or protein encoded by said first heterologous nucleotide sequence comprises, preferably consists of, a first binding polypeptide and a polypeptide encoded by said first fragment. Said polypeptide or protein encoded by said second heterologous nucleotide sequence comprises, preferably consists of, a second binding polypeptide and a polypeptide encoded by said second fragment.

After transcription and translation, each of said polypeptides or proteins has at least the following two functions:
(i) providing a part of the protein involved in said trait;
(ii) the capability of binding to the polypeptide or protein encoded by the other fragment. Amino acid sequence portions responsible for said functions (i) and (ii) may or may not overlap.

Said binding may or may not involve peptide bond formation between said proteins or polypeptides encoded by said first and second heterologous nucleotide sequences. Without peptide bond formation, said binding polypeptides may bind to each other by affinity. In this case, said binding polypeptides may be polypeptides known to bind to each other e.g., from naturally occurring binding domains of protein complexes. Preferably, said binding polypeptides involved in said binding affinity or at least one of them can be artificially engineered. Said binding polypeptides may e.g., be the components of an antigen-antibody pair. Further, said binding polypeptides may be selected artificially using e.g., random peptides phage display libraries (for review see: Barbas C F., 1993, *Curr. Opin. Biotechnol.*, 4, 526-530; Irving et al., 2001, *Curr. Opin. Chem. Biol,* 5:314-324; Hoogenboom H R, 1997, *Trends Biotechnol.*, 15:62-70) or yeast two-hybrid system (for review see Fields & Sternglanc, 1994, *Trends Genet.*, 10, 286-292; Bartel & Fields., 1995, *Methods Enzymol.*, 254: 241-263). Further, they may be intein fragments that may have been rendered non-functional for intein splicing.

In an important embodiment, said binding comprises peptide bond formation between said protein and polypeptides encoded by said first and second heterologous nucleotide sequences. Peptide bond formation between the polypeptides encoded by said fragments is preferred. Said binding is or comprises preferentially intein-mediated trans-splicing. For this purpose, said first and said second heterologous nucleotide sequences further code for proteins or polypeptides capable of protein trans-splicing. By said trans-splicing, the proteins and polypeptides encoded by said first and said second fragments may be linked by peptide bond formation. In this embodiment, said binding polypeptides are preferably derived from an intein capable of trans-splicing. Trans-splicing inteins may be selected from the nucleolar and organellar genomes of different organisms including eukaryotes, archaebacteria and eubacteria. Inteins that may be used for performing this invention are listed at www.neb.com/neb/inteins.html. Also, an intein mentioned in a reference cited herein may be used. The choice of the intein might depend on the consensus sequences as well as the conditions required for efficient trans-splicing.

For engineering said heterologous nucleotide sequences, the nucleotide sequence coding for an intein may be split into a 5' and a 3' part that code for the 5' and the 3' intein (as denoted herein), respectively. Sequence portions not necessary for intein splicing (e.g., a homing endonuclease domain) may be deleted. The intein coding sequence is split such that the 5' and the 3' inteins are capable of trans-splicing. Regarding a suitable splitting site of the intein coding sequence, the considerations published by Southworth et al. (EMBO J. (1998) 17, 918-926) may be followed. The capability of the 5' and the 3' inteins for trans-splicing may of course be tested experimentally, e.g., as described by Southworth et al. (ibid). Experimental testing may be done by trans-splicing. Experimental testing of intein portions that can be deleted without compromising trans-splicing functionality may be done by trans-splicing or by cis-splicing.

The 5' intein corresponds essentially to the first binding polypeptide. The 3' intein corresponds essentially to the second binding polypeptide. For engineering said heterologous nucleotide sequences, the 5' intein coding sequence is linked to the 3' end of said first fragment. The 3' intein coding sequence is linked to the 5' end of said second fragment. Notably in the vicinity of the linking site, nucleotides and/or codons (amino acids) may be changed to achieve a desired trans-splicing functionality.

Said first heterologous nucleotide sequence thus may comprise: said first fragment, said first binding polypeptide, regulatory sequences for transcription (e.g., promoter, 3' transcription termination sequence) and for translation. Said second heterologous nucleotide sequence may comprise: said second fragment, said second binding polypeptide, regulatory sequences for transcription (e.g., promoter, 3' transcription termination sequence) and for translation. Further, it may contain a selectable and/or a counter-selectable marker needed for producing said first and/or said second plant and sequences recognised by a site-specific recombinase or transposon sequences (cf. below).

The process of the invention may also be used to assemble two or more traits, notably by trans-splicing. However, different intein systems should be used for the assembly of each trait in order to avoid trait ads-splicing due to the universal nature of interaction between intein parts, which is independent of attached protein fragment destined for trans-splicing.

In the process of the invention, said first plant or cells thereof may be produced by introducing said first heterologous nucleotide sequence into a precursor plant or cells thereof. Said second plant or cells thereof may be produced by introducing said second heterologous nucleotide sequence into a precursor plant or cells thereof. Said introducing may be done according to methods generally known in the art.

Preferably, both heterologous nucleotide sequences are stably incorporated into a chromosome of the nuclear genome of the first and the second plant. Said first and said second plants obtained thereby are preferably made homozygous with respect to the respective heterologous nucleotide sequences according to procedures known in the art, notably by selfing. Said first and said second plants belong preferably to the same family, more preferably to the same genus, and most preferably to the same species of organisms.

The invention provides multi-cellular plants (and parts thereof like seeds) expressing a trait of interest and having a controlled distribution of said trait to progeny, whereby a protein involved in said trait is generated by binding, notably by trans-splicing, polypeptides encoded by said heterologous sequences. Said polypeptides are encoded on homologous chromosomes of said organism in a first and a second heterologous nucleotide sequence.

In principle, several relative locations of said first and said second heterologous nucleotide sequences and the respective fragments exist in the transgenic plant of the invention. Said first and said second heterologous sequences in said transgenic plant of the invention should be positioned such that they segregate as unlinked loci. Said unlinked loci are preferably positioned so as to minimize meiotic recombination or crossing-over and creation of linkage between said loci.

Possible relative locations of said first and said second heterologous nucleotide sequences and said fragments contained therein are generally shown in FIG. 2B using a diploid organism as an example.

In case I of FIG. 2B, said first and said second fragments are located on the same chromosome, i.e., they are physically linked on the same DNA molecule but are separated from each other by chromosome sequences native to the organism. The fragments will belong to different transcriptional units. Since crossing-over in meiosis may lead to separation of the fragments (or the heterologous sequences containing the fragments), the probability of transferring the trait encoded by both fragments to progeny is reduced compared to the conventional case, where the trait is encoded by a continuous coding sequence.

In case II (see FIG. 2B), said first and said second fragment are located on different heterologous chromosomes. The frequency of inheriting said trait encoded by the two fragments on different chromosomes upon self-crossing is about 50% and upon crossing with an organism not carrying any of these fragments 25%. In prior art cases I and II, the probability of transferring both fragments to progeny or to other organisms is too high for practical purposes, notably if the trait encoded in said fragments provides an advantage for survival or propagation. These cases do not represent biologically safe cases of a transgenic plant.

The inventors of this invention have found that the frequency of transferring said trait to progeny (upon crossing with plants not having said trait) and to other organisms can be enormously reduced when said fragments are located on homologous chromosomes as schematically shown in FIG. 2B, case III and IV.

In case III (FIG. 2B), the two fragments are present at different loci on homologous chromosomes, i.e., are linked in repulsion. The closer the fragments are located, the lower the frequency of recombination between said loci and, consequently, transferring the trait to progeny as the result of cross-hybridisation. In the most preferred case (case IV in FIG. 2B), the fragments are located in the same locus on homologous chromosomes. Thus, the trait reliably segregates in cross-progeny (hybrid progeny) of the multi-cellular plant of the invention.

Such relative locations of said first and said second heterologous nucleotide sequences on homologous chromosomes of the plant of the invention are achieved by hybridising, notably crossing, said first and said second plant or cells thereof. Said first and said second plant may be obtained by methods known in the art. Further possibilities are disclosed in the following.

In one embodiment, many transformants are produced with said first as well as with said second heterologous nucleotide sequence. Then, the chromosome having said heterologous sequence incorporated as well as the location of the transformed sequence in the chromosome may be determined by genetic or molecular biological methods. Next, a transformed plant or cell clone thereof having said first heterologous nucleotide sequence at a suitable location may be selected. Then, a transformed plant or cell clone thereof having said second heterologous nucleotide sequence at a suitable location relative to said first sequence may be selected. Thereby, a suitable pair of first and second plants may be chosen.

In a second embodiment, targeted integration into a desired locus of a desired chromosome is employed making use of homologous recombination. Preferably, targeted integration is done using a multi-cellular plant having a targeting site pre-integrated into a chromosome in combination with site-specific recombination. The latter approach is particularly useful for introducing said first and said second heterologous nucleotide sequence into the same locus of the same chromosome, as the same starting organism line having a pre-integrated targeting site may be used for transforming said first and said second heterologous nucleotide sequences. Targeted integration is described e.g., in international patent application PCT/EP02/03266 (WO02/077246). Methods of creating sites for targeted integration in plants with different expression profiles are described is described in PCT/US02/11924. Methods of improving the efficiency of site-targeted integration is described e.g., in international patent application PCT/EP02/03266.

Alternatively, said first heterologous nucleotide sequence can be incorporated into a chromosome of the nuclear genome of the first organism and said second heterologous nucleotide sequence can be incorporated into the plastid or mitochondrial genome of the same or another organism. However, incorporation of both heterologous nucleotide sequences into nuclear chromosomes is preferred.

Preferred methods of producing said first and said second plant are schematically depicted on the right hand side ("Excision") of FIG. 2E and in FIGS. 5 to 8. In these preferred methods, steps (i) and (ii) of claim 1 are carried out by (a) introducing a parent heterologous nucleotide sequence comprising said first and said second heterologous nucleotide sequences into a nuclear chromosome of parent organisms or cells thereof, (b) optionally selecting organisms or cells thereof having said parent heterologous nucleotide sequence integrated in a desired chromosome or chromosome locus, (c) subsequently splitting said parent heterologous nucleotide sequence so that said first and said second heterologous nucleotide sequences are located on homologous chromosomes in different plant organisms or cells.

Said parent heterologous nucleotide sequence comprises said first and said second heterologous nucleotide sequence. Preferably, it further comprises sequences for excising said first and/or said second heterologous sequence (for details see below). Said introducing (a) may be done by any known transformation method (see below). *Agrobacterium*-mediated transformation preferred. Plants or cells carrying said parent heterologous nucleotide sequence may be selected using a selectable marker contained therein. Whole plants may be regenerated from transformed cells or tissue. Preferably, plants homozygous for said parent sequence are created.

A plant (or a group of plants) carrying said parent sequence may then be used for excising said first heterologous nucleotide sequence out of said parent sequence. Thus, said second plant may be obtained. Another plant (or group of plants) may be used for excising said second heterologous nucleotide sequence for obtaining said first plant. The heterologous sequences which are not excised are located in said first and said second plant in homologous chromosomes, notably in the same locus of said homologous chromosomes, i.e., in iso-loci.

The first and second plants or cells thereof thus obtained (or progeny thereof) are advantageously analysed for any reintegration of an excised heterologous nucleotide sequence into the genome e.g., by genetic or molecular biological techniques (e.g., by PCR and use of nucleotide probes for Southern hybridisation). Plants or cells thereof may then be selected that contain said heterologous nucleotide sequence reintegrated at a desired locus on a chromosome homologous to the chromosome harboring the heterologous nucleotide sequence that has not been excised. Thus, the transgenic plant of the invention may directly be obtained. Preferably, plants or cells thereof that are free of the excised heterologous nucleotide sequence are selected. Said selection may comprise analysis by genetic or molecular biological techniques. Preferably, said selection is supported by a counter-selectable marker in the heterologous sequence to be excised. Said first and said second plant are preferably made homozygous for said heterologous sequence that has not been excised.

Said excising may e.g., be done using site-specific recombinases (cf. FIG. 2E). It is highly convenient that said excising is done using transposons, notably non-autonomous transposons (i.e., a transposon not encoding the respective transposase). For the latter embodiment, said first and/or said second heterologous nucleotide sequence in said parent heterologous nucleotide sequence is/are embedded in such a transposon. Said excision comprises providing a transposase for said transposon. Notably, (A) said first heterologous nucleotide sequence in said parent heterologous nucleotide sequence is contained in a first transposon and said second heterologous nucleotide sequence is contained in a second transposon and
(B) said first heterologous nucleotide sequence is excised by providing a first transposase functional with said first transposon and said second heterologous nucleotide sequence is excised by providing a second transposase functional with said second transposon.

Said first and said second transposons in said parent heterologous nucleotide sequence preferably overlap such that excision of said first or said second heterologous nucleotide sequence leads to disruption of said second or said first non-autonomous transposon, respectively. Overlapping transposons may conveniently be used with a selectable and a counter-selectable marker in the overlapping region as depicted in FIGS. 7 and 8.

Further, said splitting of step (c) does not necessarily require different recombinases for said excising said first or said second heterologous nucleotide sequence. In a very convenient embodiment, said first heterologous nucleotide sequence in said parent heterologous nucleotide sequence is flanked by differing recombination sites of a site-specific integrase and said second heterologous nucleotide sequence in said parent heterologous nucleotide sequence is flanked by differing recombination sites of the same site-specific integrase (cf. FIGS. 21 and 22), and step (c) is carried out by providing said site-specific integrase to said parent organism or cells thereof,
selecting progeny of said parent organism or cells thereof containing said first heterologous nucleotide sequence but not said second heterologous nucleotide sequence, and
selecting progeny of said parent organism or cells thereof containing said second heterologous nucleotide sequence but not said first heterologous nucleotide sequence.

In step (iii) the process of the invention, said first and said second plants or cells thereof are then hybridised for obtaining the transgenic multi-cellular plant of the invention. Hybridising may be sexual crossing or fusion of cells of said plants. Cell fusion may be fusion of germ cells or of somatic cells. Preferably, hybridising involves pollination of plants or somatic cell fusion of protoplasts. Sexual crossing of plants is most preferred. Said hybridising brings said fragments encoding or being involved in said trait together in one plant or cells thereof such that said plant exhibits said trait of interest due to protein trans-splicing. Exhibiting said trait due to protein binding or protein trans-splicing means that binding or trans-splicing is a necessary condition for the expression of said trait of interest. The production of the transgenic organism of the invention may comprise further steps in addition to said hybridising. In the case of plants, examples of such further steps include: growing and harvesting seeds, seeding, and growing the plant of the invention. In the case of protoplast fusion, such further steps include: propagating the fused protoplasts to obtain colonies, regeneration of plants.

Controlled distribution of said trait to progeny means that the probability of transferring said trait to progeny is significantly reduced compared to conventional transgenic organisms that have a transgene involved in said trait of interest encoded in one locus of a chromosome, notably as a single transcriptional unit, or on heterologous chromosomes. The frequency of appearance of said trait in progeny upon crossing said transgenic multi-cellular plant of the invention with a plant devoid of said first and said second heterologous sequences is less than 10%, preferably less than 1%, more preferably less than 0.1%, even more preferably less than 0.01%, an most preferably less than 0.001%. For comparison, the frequency of appearance of a transgene in progeny upon crossing a conventional transgenic (diploid) organism having said transgene in a single transcriptional unit and being heterozygous with respect to the transgene with another organism of the same species not having said transgene is about 50%. Whether a transgenic plant expressing a trait of interest fulfills the criteria of the invention regarding said frequency can be easily checked experimentally.

Herein, peptide bond means the amide linkage between the carboxyl group of one polypeptide and the amino group of another polypeptide. The linkage does not allow free rotation and can occur in cis or trans configuration, the latter the most common in natural peptides, except for links to the amino group of proline, which are always cis (source: www.mblab.gla.ac.uk/dictionary/). Peptide bond formation can be achieved through intein-mediated trans-splicing.

In the process of the invention, transgenic multi-cellular plant organisms are produced. Among plants, crop plants including barley, oat, rye, wheat, *Zea mays*, rice, millet, potato, oilseed rape, canola, tomato, cotton, sorghum, and tobacco are preferred. The processes of the invention may be applied to diploid and to polyploid plants.

Examples for traits expressible according to the invention, notably in plants, are male sterility, herbicide resistance, insecticide resistance, selectable marker, a counter-selectable marker, organism morphology, seed content, seed stability, climate adaption, vitamin content, carbohydrate content and composition, fat content and composition etc. Further, said trait may be expression of a protein of interest, notably a pharmaceutical protein. Examples for such proteins are given below. In one case (cf. example 1), reporter gene is expressed in a plant of the invention. In another example of this invention (example 2) EPSPS (5-enolpyruvylshikimate-3-phosphate synthase) gene conferring herbicide resistance, e.g., glyphosate tolerance, is expressed. Said multi-cellular plants and said transgenic multi-cellular plants of the invention may be further genetically or transiently modified e.g., for providing functions necessary for said trans-splicing and/or said expressing of the trait of interest. Further, a second transgene involved in expression of said trait of interest or of a different trait may be expressed.

The process of the invention may be used for a wide variety of applications. It may e.g., be used for expressing a trait of interest in said transgenic organism. Said trait may be any property of said organism, whether encoded by a single or by several genes. Said trait may be caused by expression of at least one protein. Two or more proteins may be necessary for said trait. In this case, it may be sufficient to control the expression of only one protein as described herein. It is, however, environmentally safer to control all the proteins producing a trait by the processes of the invention.

A highly important application of said process is the production of hybrid seeds for generating plants for agricultural purposes or for protein production in said plants, whereby said plants have a controlled distribution of a trait to progeny. Said hybrid seeds allow the generation of plants expressing a trait of interest that is neither expressed in a parental line and quickly segregates in progeny.

Producing plants or cells thereof expressing two traits of interest with controlled distribution of said traits to progeny The transgenic multi-cellular plants or parts thereof produced according to the invention may be made to express two (or more) traits of interest, whereby both traits may have a controlled distribution to progeny as defined above. For the preferred case of two such traits of interest, these are referred to in following as trait (1) and trait (2). The above description regarding said trait of interest may apply to said trait (1) or to said trait (2). Preferably, it applies to said trait (1) and to said trait (2). However, expression of trait (1) or trait (2) may depend on RNA trans-splicing of mRNA expression products of said first and said second heterologous nucleotide sequence. Translation of the trans-spliced RNA may in this case generate one of said traits (1) or (2). RNA trans-splicing is described in detail in WO02/96192 and in references cited therein. It is also possible to expressed two or more traits via RNA trans-splicing.

Preferably, the progeny generated in step (iii) of the process of the invention (i.e., the transgenic multi-cellular plants or parts thereof according to the invention) exhibits trait (1) and trait (2) due to binding between a protein or polypeptide encoded by said first heterologous nucleotide sequence and a protein or polypeptide encoded by said second heterologous nucleotide sequence. Further, said progeny may exhibit trait (1) or trait (2) due to inteinmediated trans-splicing. Further, said progeny may exhibit trait (1) and trait (2) due to intein-mediated trans-splicing.

In the process of producing a multi-cellular plant or parts thereof expressing two traits of interest, steps (i) and (ii) may be carried out similarly as described above in detail for one trait. The plant produced in step (i) (plant A1 in FIG. 13) may contain a (first) fragment of a nucleotide sequence encoding trait (1) and a (first) fragment of a nucleotide sequence encoding trait (2). The plant produced in step (ii) (plant A2 in FIG. 13) may contain another (a second) fragment of a nucleotide sequence encoding trait (1) and another (a second) fragment of a nucleotide sequence encoding trait (2). Said first fragments (of trait (1) and of trait (2)) in the plant produced in step (i) may be on the same or on different chromosomes. Similarly, said second fragments (of trait (1) and of trait (2)) in the plant produced in step (ii) may be on the same or on different chromosomes. It is preferred that said first fragments are on the same chromosome and that said second fragments are on the same chromosomes. More preferably, said first fragments are in the same locus of a chromosome and said second fragments are in the same locus of a chromosome. Most preferably, the locus having said first fragments of said first plant and said locus having said second fragments of said second plant are the same loci on homologous chromosomes, i.e., are iso-loci.

In the process of producing a multi-cellular plant or parts thereof expressing two traits of interest, steps (i) and (ii) may be carried out similarly as described above in detail for one trait. The plant produced in step (i) (plant A1 in FIG. 13) may contain a (first) fragment of a nucleotide sequence encoding trait (1) and a (first) fragment of a nucleotide sequence encoding trait (2). The plant produced in step (ii) (plant A2 in FIG. 13) may contain another (a second) fragment of a nucleotide sequence encoding trait (1) and another (a second) fragment of a nucleotide sequence encoding trait (2). Said first fragments (of trait (1) and of trait (2)) in the plant produced in step (i) may be on the same or on different chromosomes. Similarly, said second fragments (of trait (1) and of trait (2)) in the plant produced in step (ii) may be on the same or on different chromosomes. It is preferred that said first fragments are on the same chromosome and that said second fragments are on the same chromosomes. More preferably, said first fragments are in the same locus of a chromosome and said second fragments are in the same locus of a chromosome. Most preferably, the locus having said first fragments of said first plant and said locus having said second fragments of said second plant are the same loci on homologous chromosomes, i.e., are iso-loci.

In the aforementioned preferred embodiment, a strictly controlled distribution of trait (1) and of trait (2) in the plant produced by the process of the invention can conveniently be achieved, if said first and said second heterologous nucleotide sequence are located in iso-loci in said first and said second plant. Therefore, progeny obtained by crossing said transgenic multi-cellular plant of the invention that expresses said two traits of interest with another plant not containing said fragments will express neither trait (1) nor trait (2).

Steps (i) and (ii) are preferably carried out by
(a) introducing a parent heterologous nucleotide sequence comprising said first and said second heterologous nucleotide sequences into a nuclear chromosome of parent organisms or cells thereof,
(b) optionally selecting organisms or cells thereof having said parent heterologous nucleotide sequence integrated in a desired chromosome or chromosome locus,
(c) subsequently splitting said parent heterologous nucleotide sequence so that said first and said second heterologous nucleotide sequences are located on homologous chromosomes in different plant organisms or cells, whereby said first heterologous nucleotide sequence of said parent nucleotide sequence contains the first fragment of trait (1) and the first fragment of trait (2), and said second heterologous nucleotide sequence of said parent nucleotide sequence contains the second fragment of trait (1) and the second fragment of trait (2). Said splitting of step (c) may be carried out as described above, whereby plant A1 and plant A2 may be obtained. Preferably, said plants produced in step (i) and in step (ii) are selfed for rendering them homozygous for said first and/or said second heterologous nucleotide sequence.

Examples for trait (1) and for trait (2) may be those given above.

Process of Hybrid Seed Production

In an embodiment of utmost importance, trait (1) is herbicide resistance and trait (2) is male or female sterility, whereby male sterility is preferred. In this embodiment, the process of the invention may be used for hybrid seed production for agricultural purposes. Thus, the invention provides a process of producing hybrid seeds, comprising producing a transgenic multi-cellular plant according to the invention (referred to herein as plant A1/A2 in FIG. 13). Preferably, trait (1) is a herbicide resistance and trait (2) is male sterility. Said process of producing hybrid seeds typically further comprises crossing said transgenic multi-cellular plant organism with another plant that is male fertile (referred to herein as plant B in FIG. 13). Plant B should not contain a fragment of a nucleotide sequence encoding said herbicide resistance or said male sterility. The hybrid seeds growing on the male-sterile herbicide resistant plant A1/A2 may then be harvested. The invention also provides the hybrid seed obtained thereby.

The use of said herbicide resistance trait said the process of producing hybrid seeds has the following advantages (cf. FIG. 13): said resistance may be used for selecting plants containing said parent heterologous nucleotide sequence (line A in FIG. 13). Further, said herbicide resistance may be used for selecting male sterile cross-progeny in step (iii) of the invention (cross-progeny of line A1 and line A2 in FIG. 13), as non-sterile self progeny of line A1 and non-sterile self-progeny of line A2 is not herbicide resistant. Consequently, purely male sterile stands of plants may be obtained, and, upon crossing with line B, progeny seeds growing on the male sterile line A1/A2 will be 100% hybrid. Self-progeny seeds growing on plants of line B may be separated by harvesting seeds of line A1/A2 separately from seeds growing on line B. In contrast to prior art processes of producing hybrid seeds using male sterile plant lines, the process of producing hybrid plants disclosed herein is of much more efficiency and less laborious to perform, as the plant lines A1 and A2 may easily maintained by selfing.

Line A containing the pro-locus sequence (FIG. 13) may be male sterile. This is advantageous for generating primary transformants of line A with a desired phenotype (e.g., male sterility, herbicide resistance etc.), but maintenance of line A may then be difficult. Line A may therefore be designed such that it is fertile, but lines A1 and A2 may still provide male sterile plant A1/A2 upon crossing. This may be achieved by separating, in said parent heterologous nucleotide sequence of line A (pro-locus), one of the fragments of the nucleotide sequence encoding the male sterility trait from its promoter. Then, said pro-locus would not provide for male sterility, as one of the fragments encoding male sterility is not expressed. Creation of iso-loci (lines A1 and A2) may bring together promoter and fragment such that said fragment can be expressed, thus allowing to obtain male sterile A1/A2 plants. As an example, said first heterologous nucleotide sequence may interrupt said second heterologous nucleotide sequence in the pro-locus. Upon creation of lines A1 and A2, excision of said first heterologous nucleotide sequence may restore the functionality of said second heterologous nucleotide sequence.

Due to the controlled distribution of both traits to progeny, the cross-progeny (F1 progeny in FIG. 13) will show hybrid vigor and have restored fertility and restored sensitivity to the herbicide the plant A1/A2 was resistant against. Preferably, sterility and herbicide sensitivity are restored in at least 96% of the progeny, more preferably in at least 99% of the progeny. Consequently, said F1 progeny may be used for large scale planting on farm fields without any danger of outcrossing or transferring a functional herbicide resistance gene in the environment.

In example 4 of the invention, engineering of split AHAS gene providing for resistance to imidazoline and sulfonylurea herbicides is described. The AHAS gene was PCR amplified from *Arabidopsis* genomic DNA, mutated and cloned in vectors (FIG. 16) for testing its functionality in transient assays.

In example 5, engineering of split barnase providing for a cytotoxic RNase is described. In both examples, we use the intein system to provide for trans-splicing of proteins encoded by split gene fragments. Trans-splicing is mediated by two different intein systems which do not cross-react with each other. This system is based on *Synechocystis* sp. PCC6803 DnaE intein for AHAS and the DnaB intein for barnase. The intermediate constructs with split AHAS-intein fusions and split barnase-intein fusions are shown in FIGS. 17 and 18, respectively.

Transient test experiments showed the intein-mediated assembly of functional proteins encoded by gene fragments. The invention is not limited to the use of the AHAS gene providing for herbicide resistance. Many other genes conferring herbicide resistance can be used, subject to correct splitting and reconstruction by intein-mediated trans-splicing. Examples of such genes include inter alia 5-enolpyruvylshikimate-3-phosphate synthase, phosphinothricin acetyl transferase (BAR), betaine aldehyde dehydrogenase (BADH), dihydrofolate reductase (DFR1), acetolactate synthase (ALS), glyphosate oxidoreductase.

Further, barnase is one of several possible genes that may provide for male sterility. Many other genes that affect pollen development when expressed in anther cells or at a desired stage of pollen formation may be employed. Actually, any gene, the gene product of which is capable of interfering with the function and development of pollen can be used in this invention. Examples of such genes inter alia ribosomal inhibitor proteins (Cho et al., 2001, *Mol. Cells,* 11, 326-333), sucrose isomerase (WO159135), protease, glucanase (Tsuchia et al., 1995, *Plant Cell Physiol.,* 36, 487-494), etc. Alternatively, genes responsible for self-incompatibility (preventing self-pollination of plants containing said genes) may be used to provide for hybrid seeds production, notably instead of the male sterility trait discussed above (Entani, T., et al., 2003, *Genes Cells,* 8, 203-213; Ushijima, K., et al., 2003, *Plant Cell,* 15, 771-781).

Various pollen or tapetum-specific promoters can be used to drive the expression of a gene/gene fragments for producing male sterility. Examples of tapetum specific promoters are promoters of the A3 and A9 genes (U.S. Pat. No. 5,723,754; Hodge et al., 1991, *J Exp. Botany,* 42, 238 Suppl. p. 46), the tapetum-specific promoter from rice Osg6B gene (Tsuchia et al., 1994, Plant Mol. Biol., 26, 1737-1746), the promoter of tobacco gene TA29 (Kriete et al., 1996, Plant J., 9:809-818), etc. Tissue-specific expression of a gene providing for male-sterility is described in detail in WO98/32325.

In the next step of cloning, said gene fragments were assembled in pairs in intermediate constructs (FIG. 19) designed for final pro-locus vector engineering (FIG. 21) according to the description in example 6. Said pro-locus vector is designed for generation of parental line A, as described in example 8. Said parental line that will be male-sterile can be selected by using the herbicide resistance provided by split AHAS gene. For generating lines A1 and A2 from the parental plant, site-specific recombination may be used. A description of vectors providing for recombinase activity is presented in example 7. The transgenic plants carrying recombinase genes may be generated in the same way as the parental plants carrying pro-locus. Methods of transformation are exemplified in example 8.

In order to generate lines A1 and A2 carrying iso-loci, primary transformants corresponding to the parental line were cross-pollinated with pollen from the plant providing for recombinase activity (example 8). The progeny from such crosses was tested by PCR for the presence of heterologous DNA corresponding to one and the absence of the heterologous DNA corresponding to the another iso-locus and vice-versa. The generation and structure of iso-loci is shown in FIG. 22. Generated lines A1 and A2 carrying different iso-loci were tested for their functionality by cross-pollination. If homozygous lines were used, all progeny from such lines was herbicide resistant and male sterile. In FIG. 22, we demonstrate the possibility of generating iso-loci from a pro-locus with the help of one site-specific recombinase. For recombinase PhiC31, recombination (excision or integration) requires two different recombination sites, AttP and AttB. Recombination catalysed by this integrase is an irreversible process, as it leads to the formation of AttL or AttR sites that are not recognised by recombinase PhiC31. The pro-locus shown in FIG. 22 contains three such sites and random interaction between two of them (catalysed by the integrase) would lead to excision event with two possible outcomes, generating either line A1 or line A2 with iso-loci. In contrast, a similar approach with parental line transformed with vector pICH12970 (FIG. 21) will produce four different variants of iso-loci with and without HPT selectable marker due to the presence of an additional AttB site.

The approach with said pro-locus in parental line A has important advantages over known hybrid seed production systems: it allows to directly select primary transformants showing the required male sterile phenotype; fertility restoration during the generation of lines A1 and A2 with iso-loci from parental line may be tested. This reduces the time necessary for developing the hybrid seed production system of the invention and makes its maintenance convenient and straightforward.

In addition, the approach of the invention is easily compatible with other methods, for example with methods of controlling seed germination. Controlling seed germination may address specific biosafety issues, especially in the case of producing industrial enzymes, proteins for human and animal health, etc., in hybrid plants. Controlling seed germination can eliminate the problem caused by plant-"volunteers" which frequently contaminate the following harvest and may pose a serious biosafety problem, especially in case of "pharma" proteins. There are several reports addressing the issue of controlling seed germination (U.S. Pat. No. 5,723, 765; WO9744465; U.S. Pat. No. 5,129,180; U.S. Pat. No. 5,977,441), however, these methods are not integrated into a process of producing hybrid seeds. Controlling the germination of seeds harvested from hybrid plants may be done according to the general teaching of this invention. Preferably, the hybrid (F1) plant is homozygous for an inactive locus A3 (see FIG. 14D) that can control seed germination after being activated (the activated locus A3 is designated A3* in FIG. 14D). This would provide all progeny of F1 plants with locus A3. Said homozygocity in Fl may be achieved by introducing a heterologous sequence controlling seed germination in a predetermined position of a nuclear chromosome of line A1/A2 (or its precursor lines A1, A2 or line A) and in line B e.g., via homologous recombination or site-directed integration. Alternatively, introgression of the desired locus by standard breeding methods is also possible. In addition, the hybrid plant (F1) should contain an activator (A4+B4) for said inactive locus (A3), said activator may be encoded by two heterologous nucleotide sequences, A4 and B4 (FIG. 14D). Sequences A3, A4, and B4 may be brought together as the result of crossing between line A1/A2 and line B to produced F1 plants. In F1 plants, the activator can be rendered functional by intein- or ribozyme-mediated trans-splicing of protein or RNA sequences, respectively, expressed from sequences A4 and B4. Preferably, said activator is a recombinase or a transposase under control of a transiently active promoter (U.S. Pat. No. 597,741), whereby said promoter is preferably not embryo-, seed- or seed germination specific, i.e., it does not overlap with or precede the expression pattern of the promoter driving the expression of gene(s) of the A3 locus that controls seed germination. The promoter controlling A3 and said gene controlling seed germination (A3) may be separated by a blocking sequence which can be removed by said recombinase/transposase used as said activator. Alternatively, said promoter controlling A3 or said gene controlling seed germination can be re-oriented relative to each other by site-specific recombination, resulting in activation and expression of A3. The activated A3 (A3*) will be inherited to progeny of F1 plants. Self-progeny of F1 plants will be homozygous for A3*, cross progeny of F1 plants will be heterozygous for A3*. Consequently, progeny seeds of the F1 plants will not be viable, i.e., stop growth in an early stage of development.

The development of a plant can be divided into two major groups of stages following germination: vegetative stages (V) and reproductive stages (R). Vegetative stages begin with emergence stage (VE) followed by the cotyledon stage (VC) and by consecutive stages of vegetative development until the beginning of reproductive stages (beginning bloom). Thus, the invention also provides plants grown from the hybrid seeds of the invention, wherein progeny seeds of said (hybrid) plants do not reach the cotyledon stage, preferably they do not reach the VC stage, preferably they do not reach the VE stage, most preferably they do not germinate. Using this embodiment, hybrid plants with a potentially problematic genetic content may be used e.g., for expressing a protein of interest, without the danger that seeds from these plants give rise to unwanted plants in the next growing season.

B—depicts four possible relative locations of the first and the second heterologous nucleotide sequences on host chromosomes of an organism. Case III and IV show relative locations of said heterologous sequences in the transgenic multi-cellular plant of the invention. A diploid organism having two chromosomes and a trait of interest encoded by two fragments (A and B) is used as an example.

C—depicts the basic principle of achieving allelic locations of said first and said second heterologous nucleotide sequences providing for trans-splicing by means of site-targeted integration.

D—depicts the basic principle of achieving allelic locations of said first and said second heterologous DNA sequences providing for trans-splicing by means of transposition.

E—general scheme of methods for achieving allelic locations of different heterologous DNA sequences on homologous chromosomes.

Figure 3:
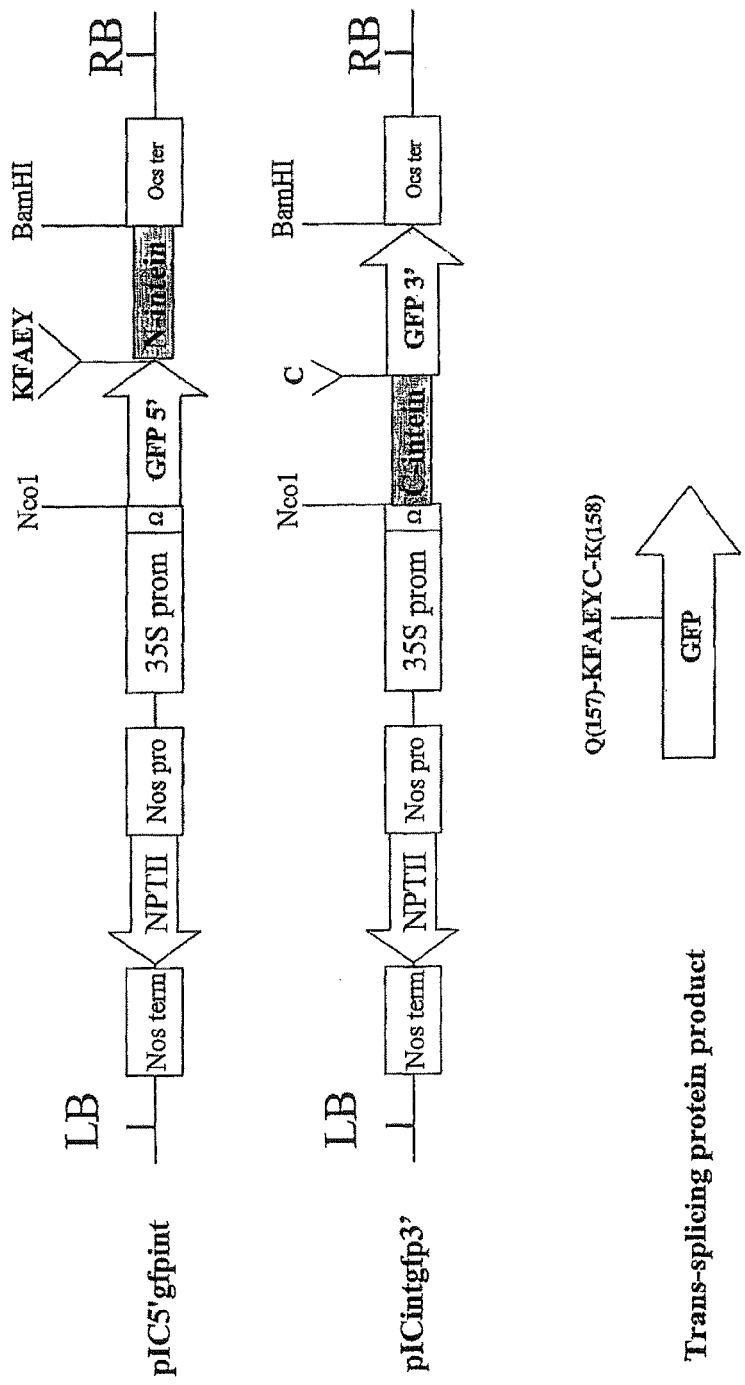

FIG. 3 shows schematic representations of T-DNA regions for plasmids plC5'gfpint and plCintgfp3'.

Figure 4:
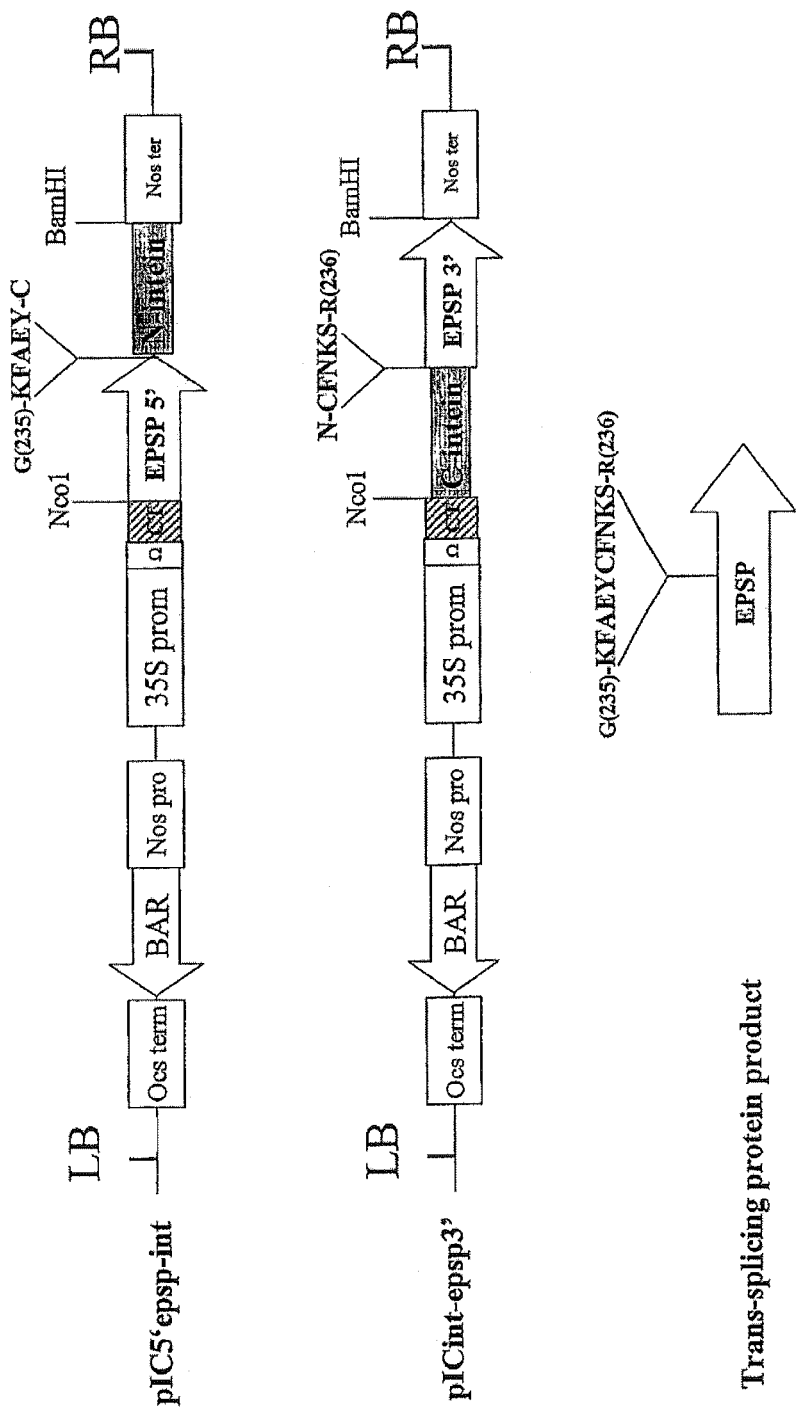

FIG. 4 depicts schematic representations of T-DNA regions for plasmids plC5'epsp-int and plCint-epsp3'.

Figure 5:
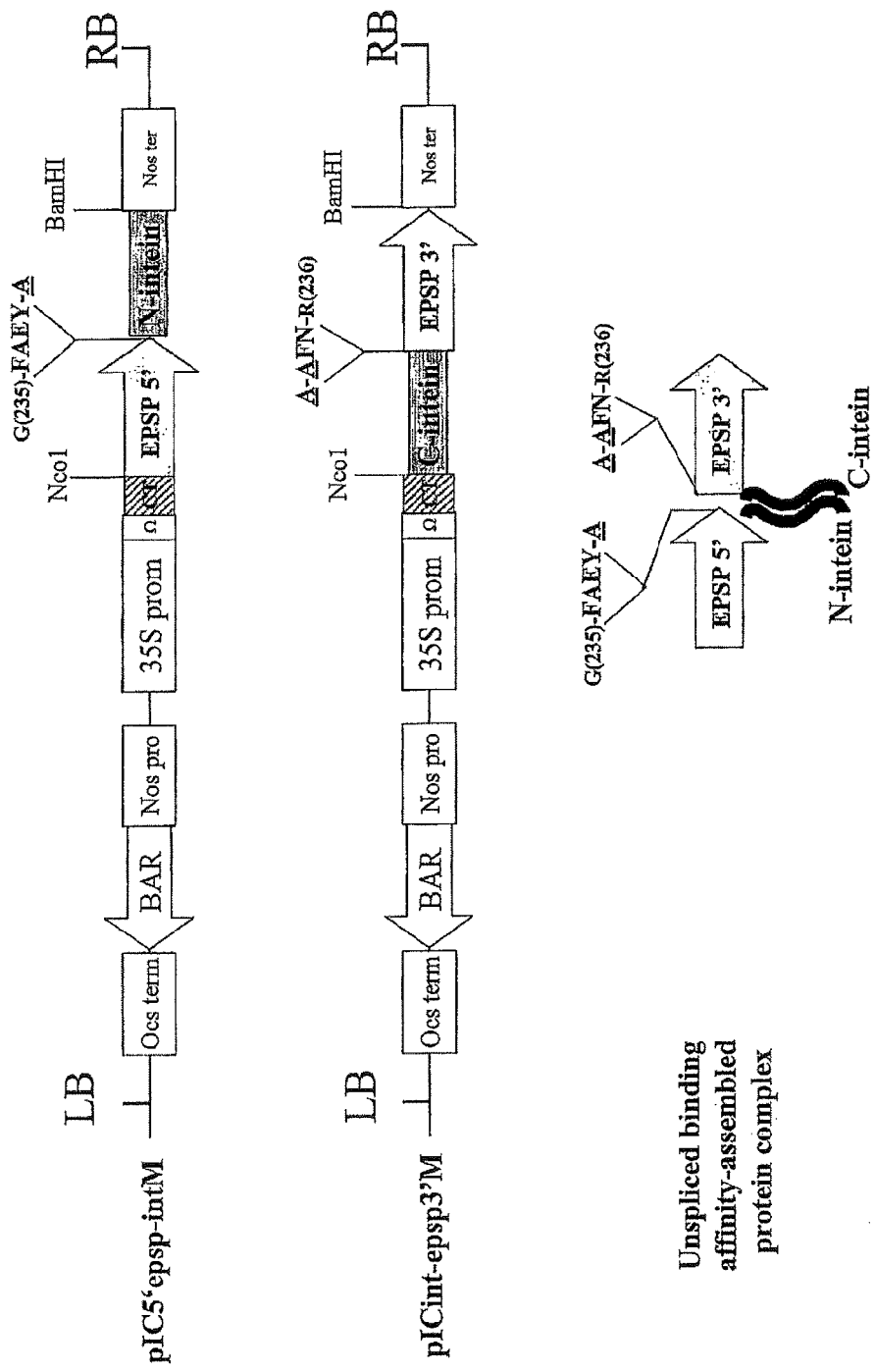

FIG. 5 depicts schematic representations of T-DNA regions for plasmids plC5'epsp-intM and plCint-epsp3'M.

Figure 6:
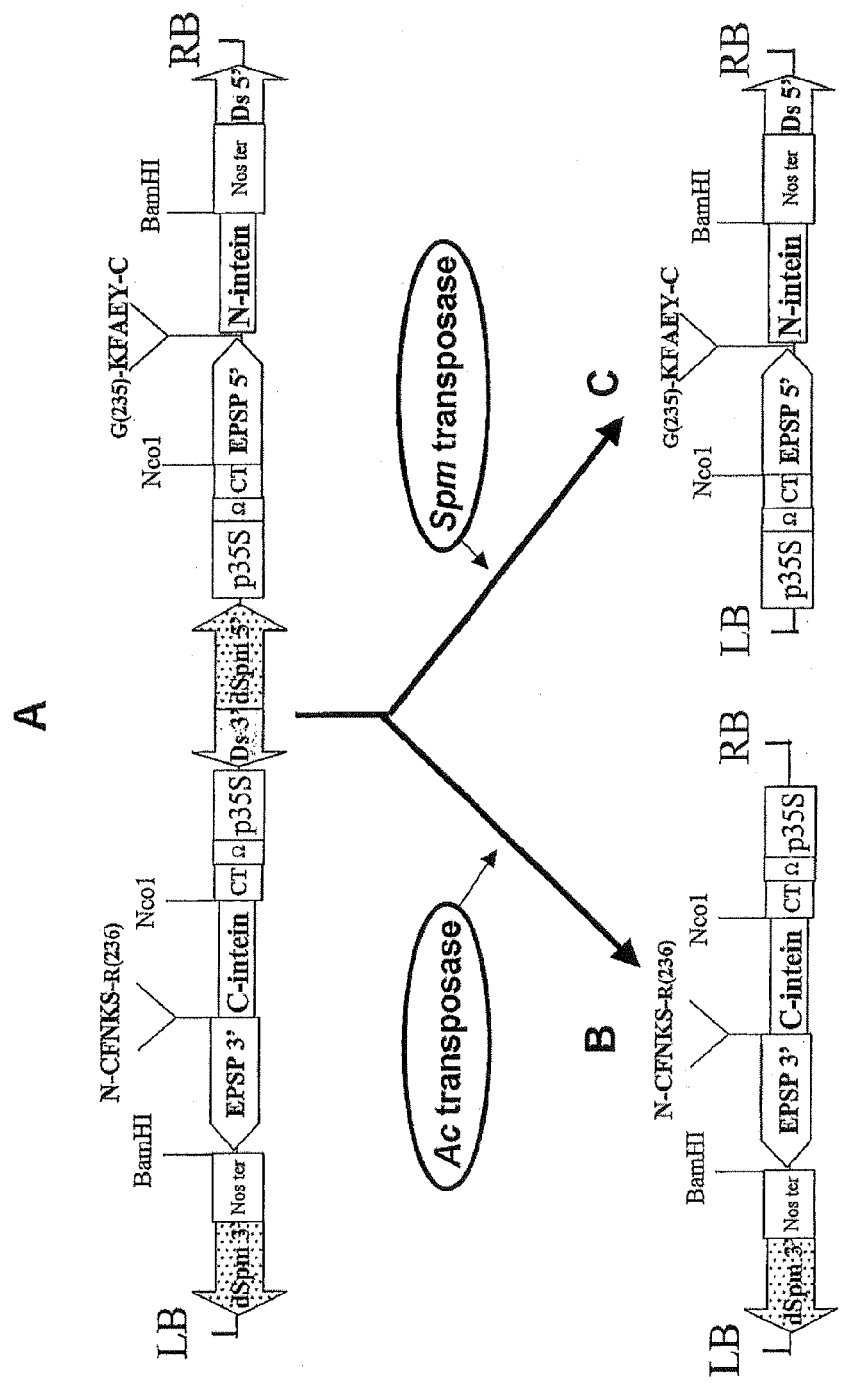

FIG. 6 depicts a schematic representation of a construct designed for achieving allelic location for the 5' or 3' parts of EPSP coding sequence (A) and its derivatives (B and C) resulting from excision of non-autonomous transposable elements (Ds or dSpm, respectively) upon exposure to transposase source.

Figure 7:
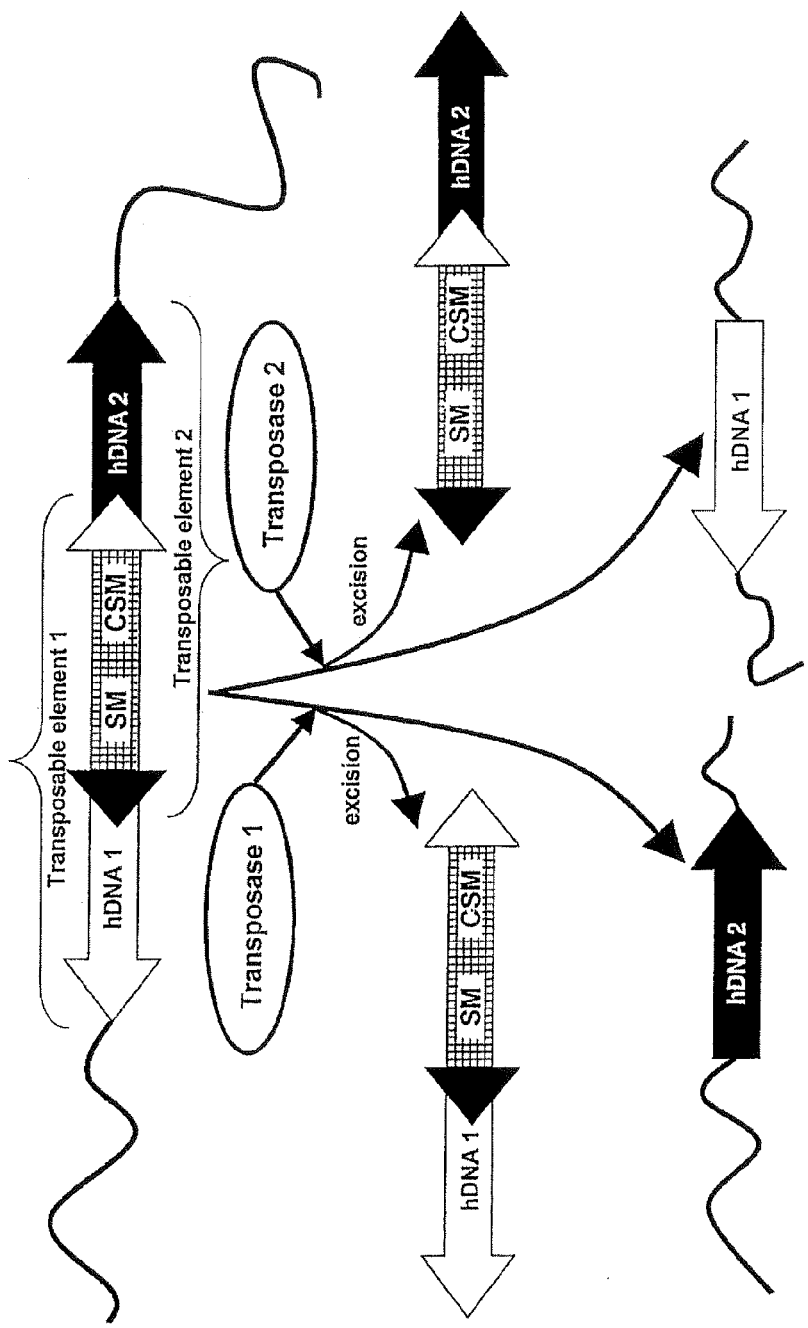

FIG. 7 depicts a general scheme of a construct (center) designed for achieving allelic locations of different heterologous DNA fragments (hDNA 1 and hDNA 2) by way of transposition-mediated removal of unwanted fragments upon exposure to a transposase source. SM—selectable transformation marker; CSM—counter-selectable marker. On the top, the unwanted fragments excised by the action of the respective transposase are shown. At the bottom, the desired fragment left behind by the transposition are shown.

Figure 8:
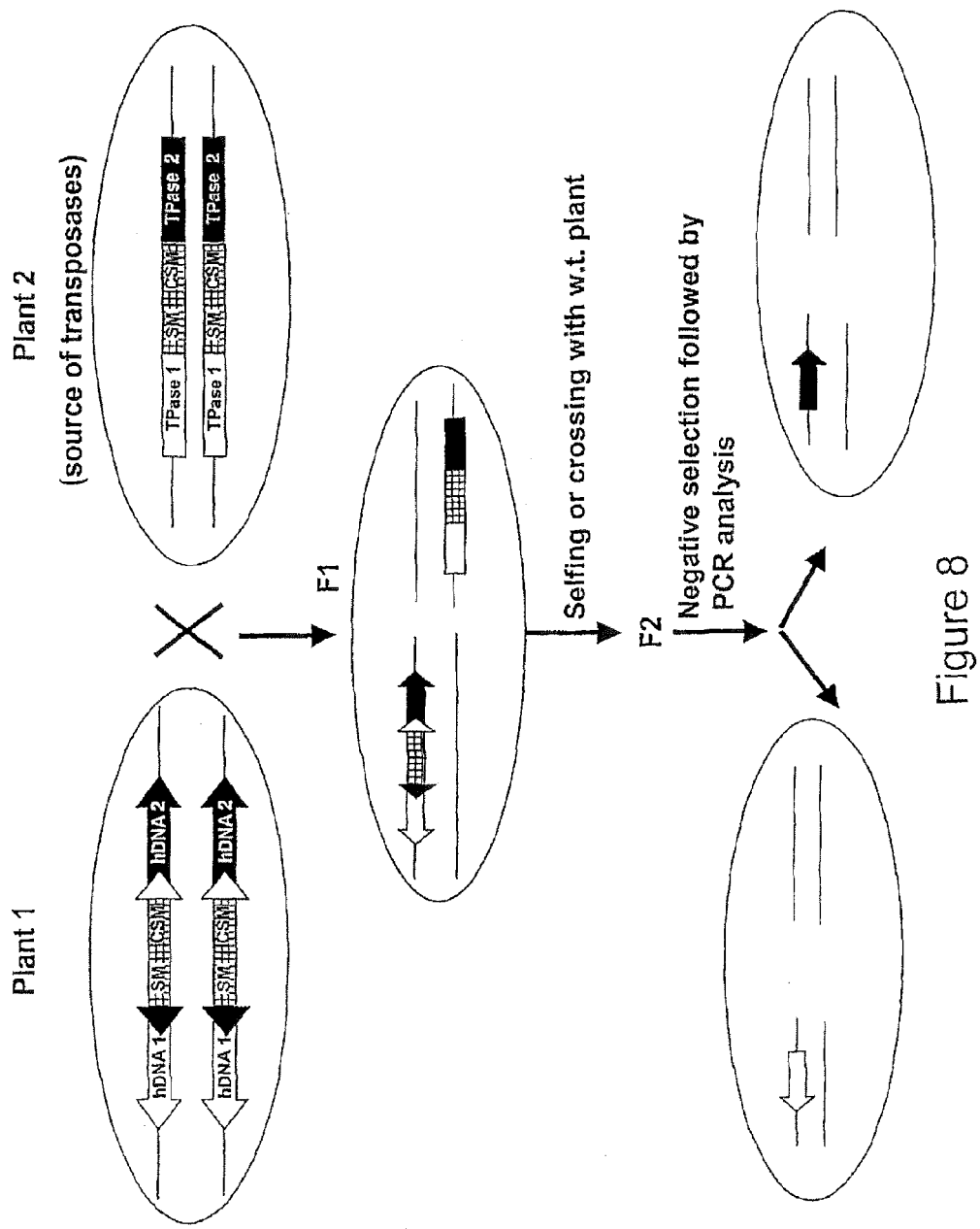

FIG. 8 shows a schematic representation of a method of generating plants with different heterologous DNA fragments (hDNA 1 and hDNA 2) in allelic locations using transposition. A transposase is provided to progeny of plant 1 by crossing plant 1 with plant 2. SM—selectable marker gene; CSM—counter-selectable marker gene; TPase—transposase.

Figure 9:
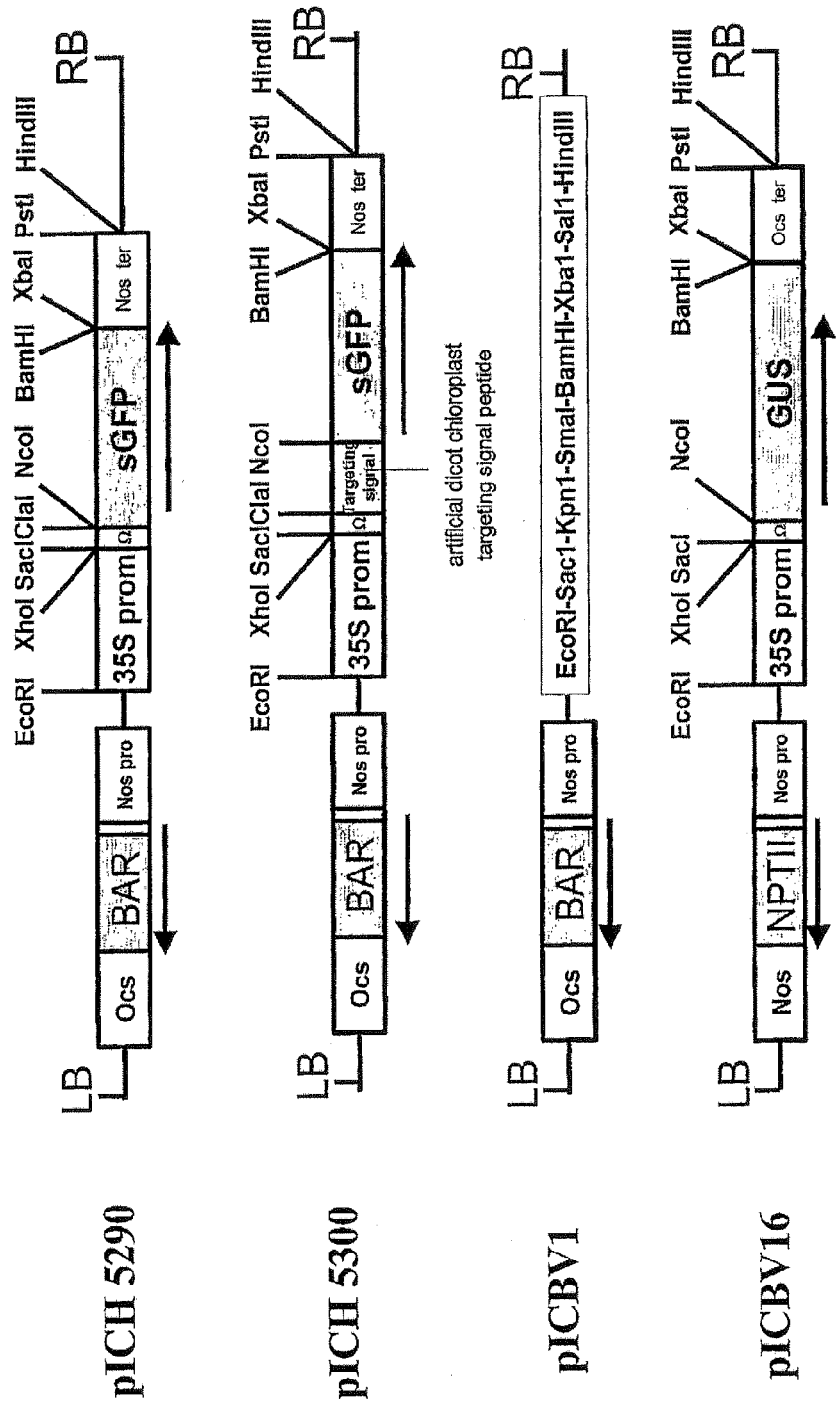

FIG. 9 depicts intermediate constructs and Binary vectors used to make constructs shown in FIGS. 3 and 4.

Figure 10:
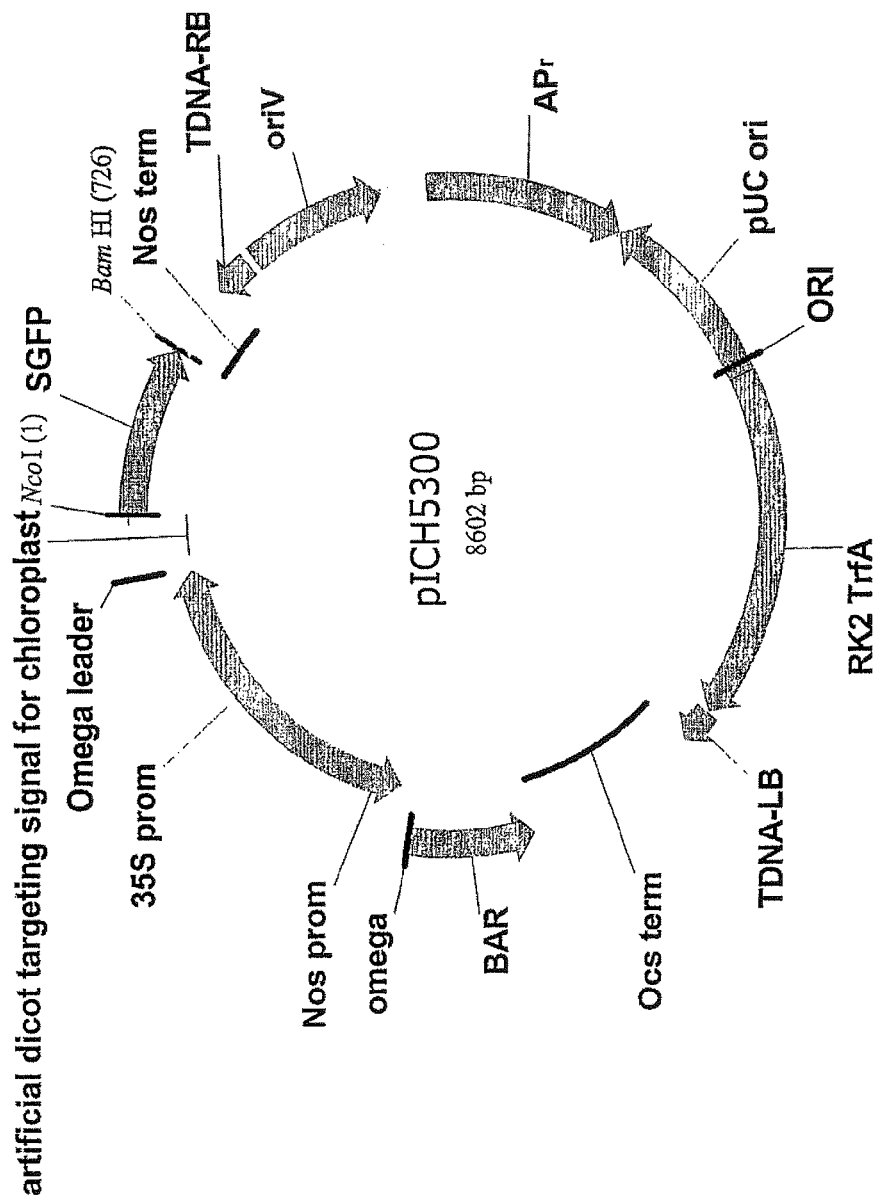

FIG. 10 depicts a map of plasmid plCH5300.

Figure 11:
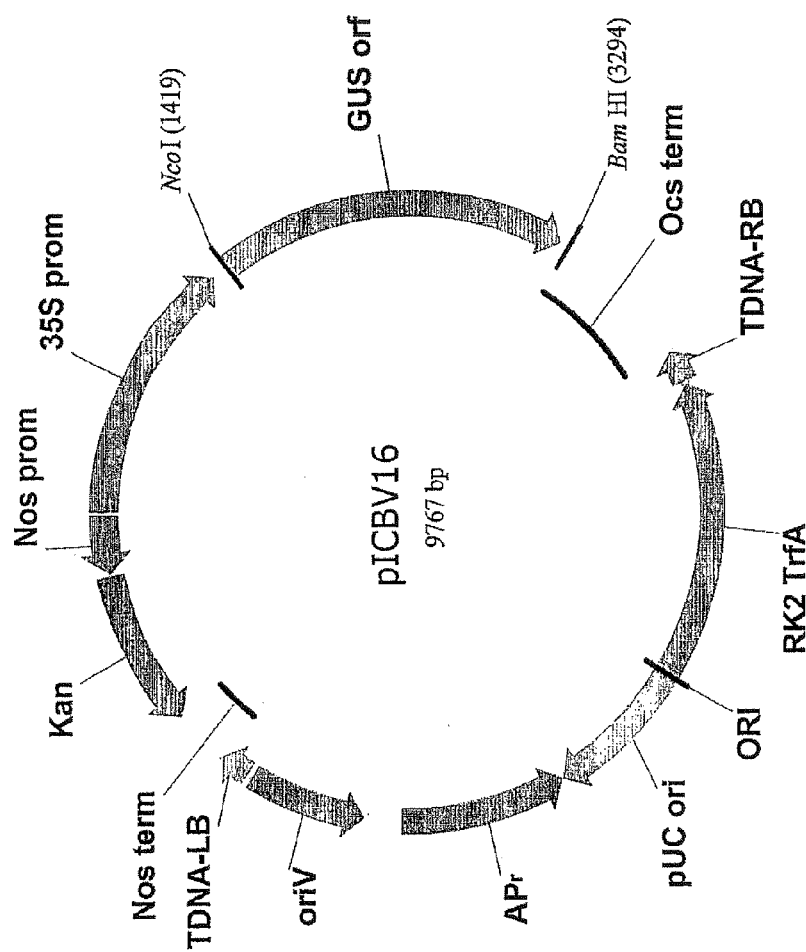

FIG. 11 depicts a map of Icon Genetics Binary vector plCBV16.

Figure 12:
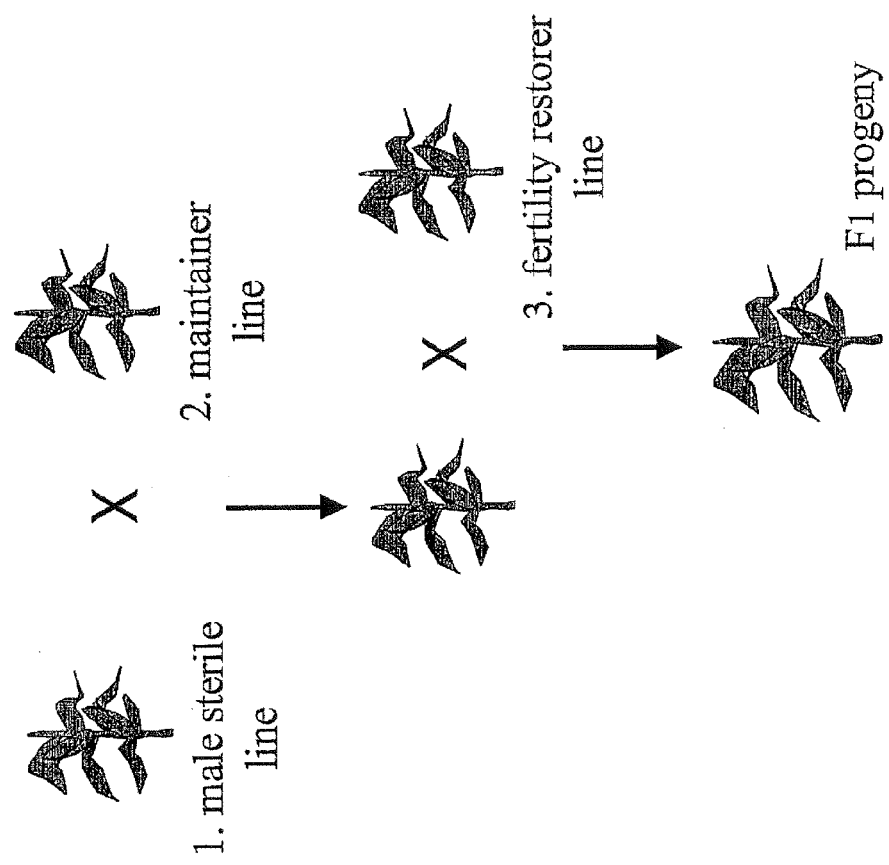

FIG. 12 depicts the general schemes for existing genetic/transgenic hybridization systems. Current systems require to engineer three plant lines—a male sterile line, a maintainer line, and a fertility restores line.

Figure 13:
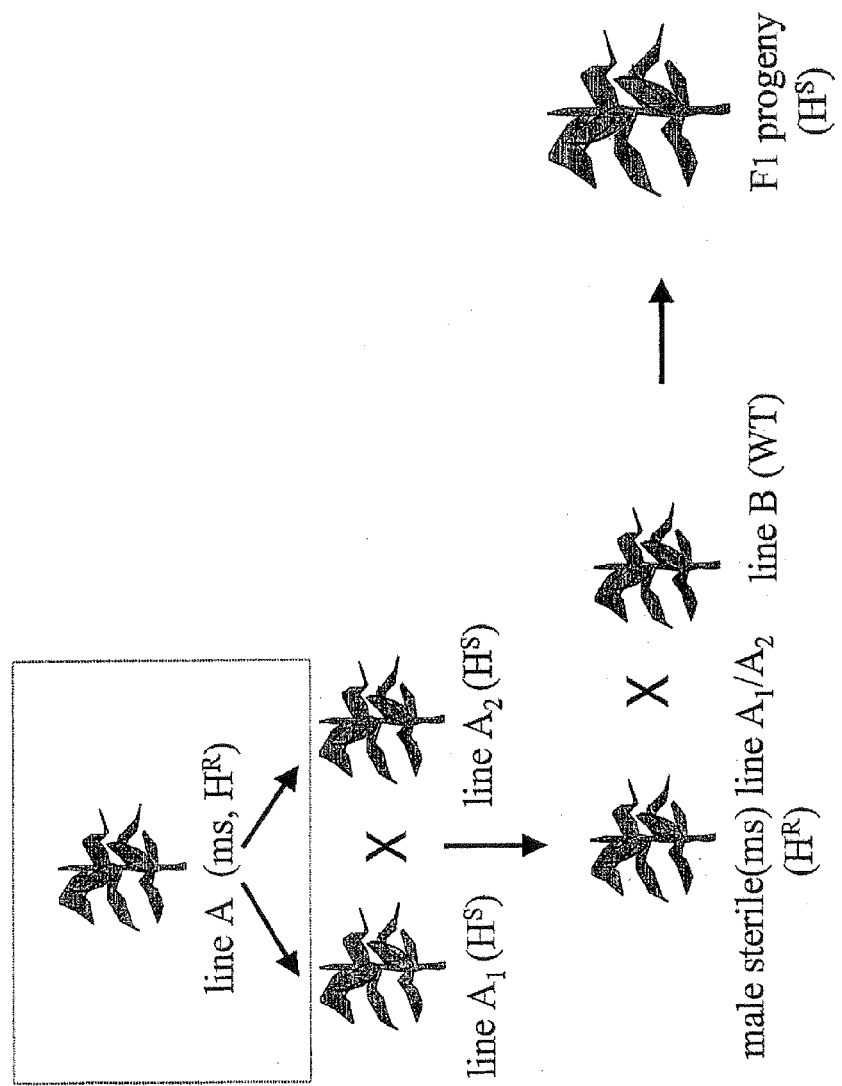
Figure 14A:
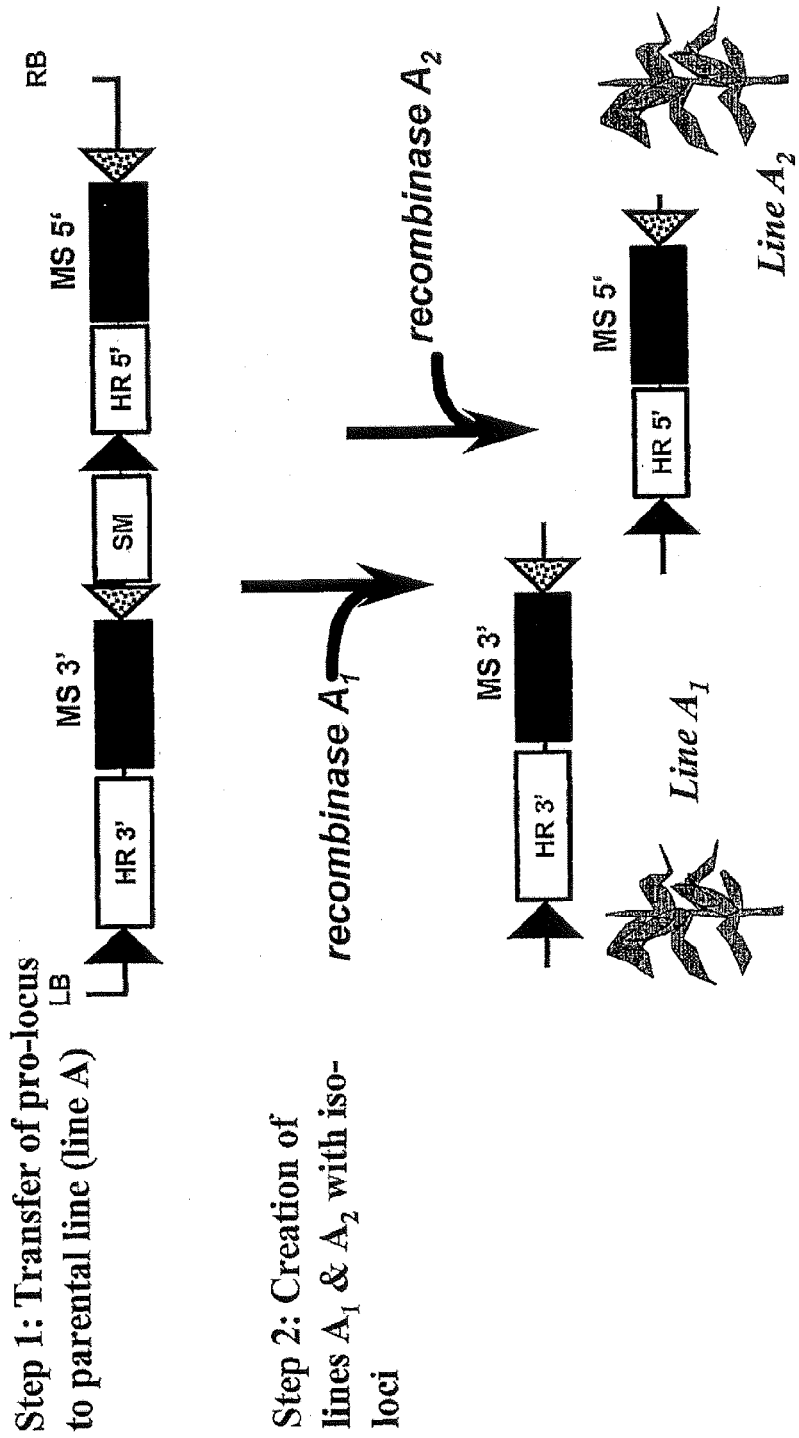
Figure 14B:
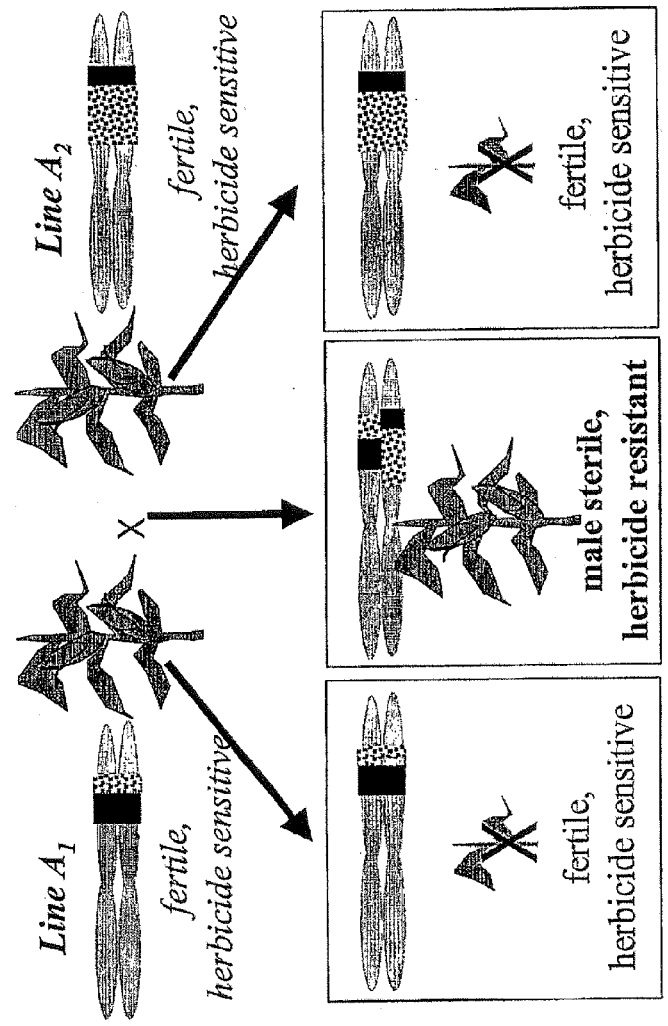
Figure 14D:
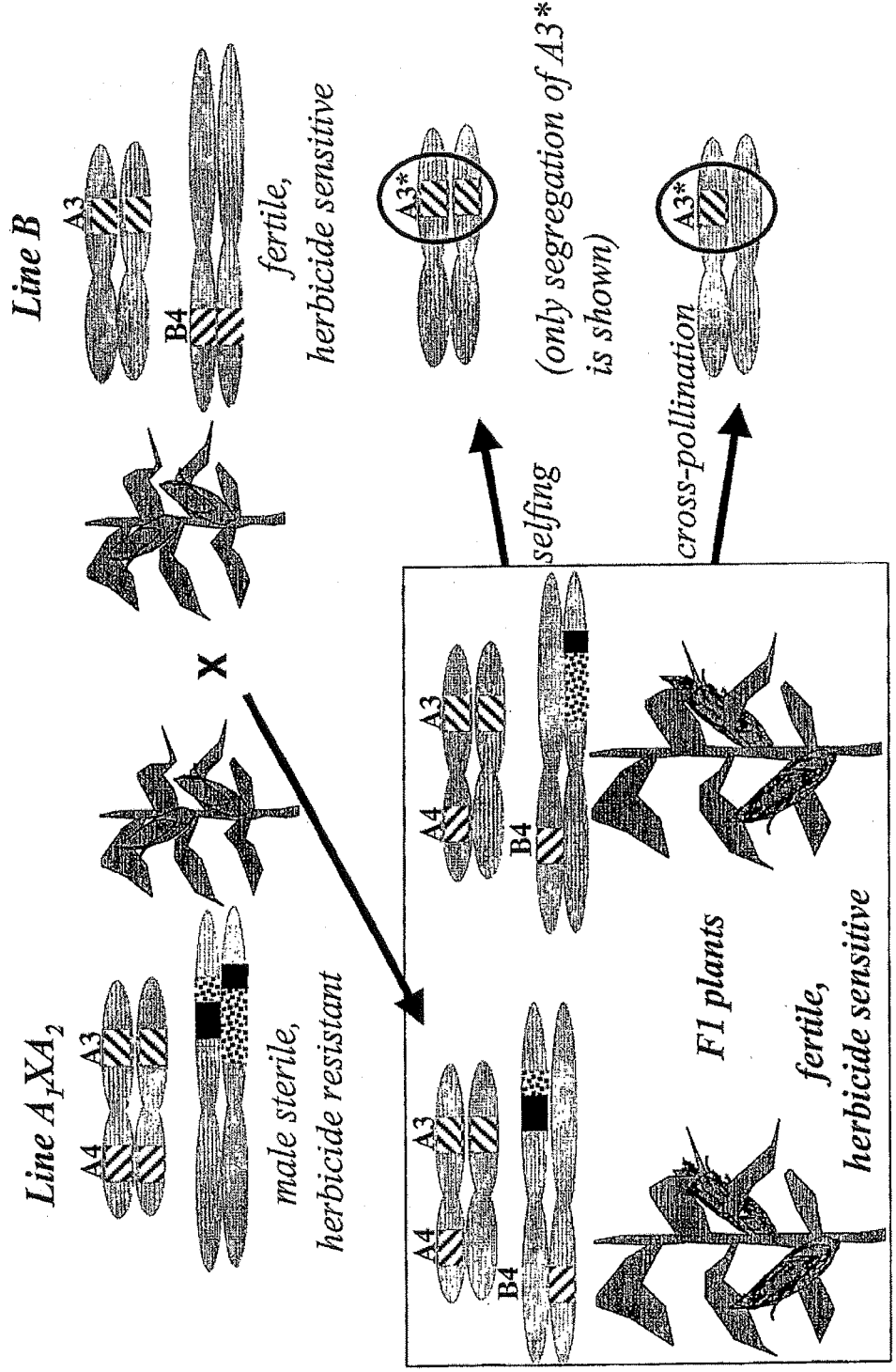

FIG. 13 depicts schematically the principle of the process of producing hybrid seeds according to the present invention. This system requires to design only one original parental line A with pro-locus containing the parent heterologous nucleotide sequence of the invention. Line A may be herbicide resistant ($FI^R$) and male sterile (ms), allowing selection using the appropriate herbicide for the resistance trait employed. Splitting of said parent heterologous nucleotide sequence leads to line A1 and line A2 containing said first and said second heterologous nucleotide sequence, respectively. Lines A1 and A2 are therefore male fertile and herbicide sensitive ($H^s$). Lines A1 and A2 may be maintained by selfing. Crossing of line A1 and line A2 leads to the male sterile and herbicide resistant line A1/A2 of the invention, whereby self-progeny of line A1 and self-progeny of line A2 may be eliminated using said herbicide resistance. Crossing of line A1/A2 with a line B that may be a wild-type (WT) line leads to seeds (F1 progeny) growing on A1/A2 plants. When said F1 progeny seeds are sewed, F1 plants growing therefrom will show hybrid vigor.

FIG. 14A-D shows steps of the process of producing hybrid seeds according to the invention. A—scheme of creating lines A1 and A2 with iso-loci from parental line A having a pro-locus containing the parent heterologous nucleotide sequence depicted at the top. Treatment of line A with recombinase A1 removes a part of the parent heterologous nucleotide sequence containing fragments HR5' and MS5', thus forming line A1. Treatment of line A with recombinase A2 removes a part of the parent heterologous nucleotide sequence containing fragments HR3' and MS3', thus forming line A2.

All the gene fragments may be designed as translational fusions with intein fragments capable of trans-splicing. Filled and dotted triangles show the recombination sites recognised by different site-specific recombinases.

SM—selectable marker; HR 3'-3' fragment of gene conferring herbicide-resistance; HR 5'-5' fragment of the gene conferring herbicide resistance; MS 3'-3' fragment of the gene providing for male sterility; MS 5'-5' fragment of the gene providing for the male sterility.

B—creation of male sterile line (at the bottom in the middle) by crossing line A1 and line A2. Self-progeny of line A1 (left picture at the bottom) and self-progeny of line A2 (right picture at the bottom) can be eliminated due to herbicide sensitivity, allowing pure stands of the male sterile herbicide resistant line A1/A2 (at the bottom in the middle).

C—production of hybrid seeds by crossing line A1/A2 (line A1×A2). All progeny is herbicide sensitive and male sterile. Cross progeny shows hybrid vigor, whereas self-progeny of line B does not. Self-progeny seeds growing on plants of line B may be separated from cross-progeny seeds growing one line A1/A2 by harvesting them separately.

D—shows production of hybrid seeds providing for F2 progeny with controlled seed germination. A3 locus provides for controlling the seed germination once activated (A3*) by activator provided by A4 and B4 loci.

Figure 15:
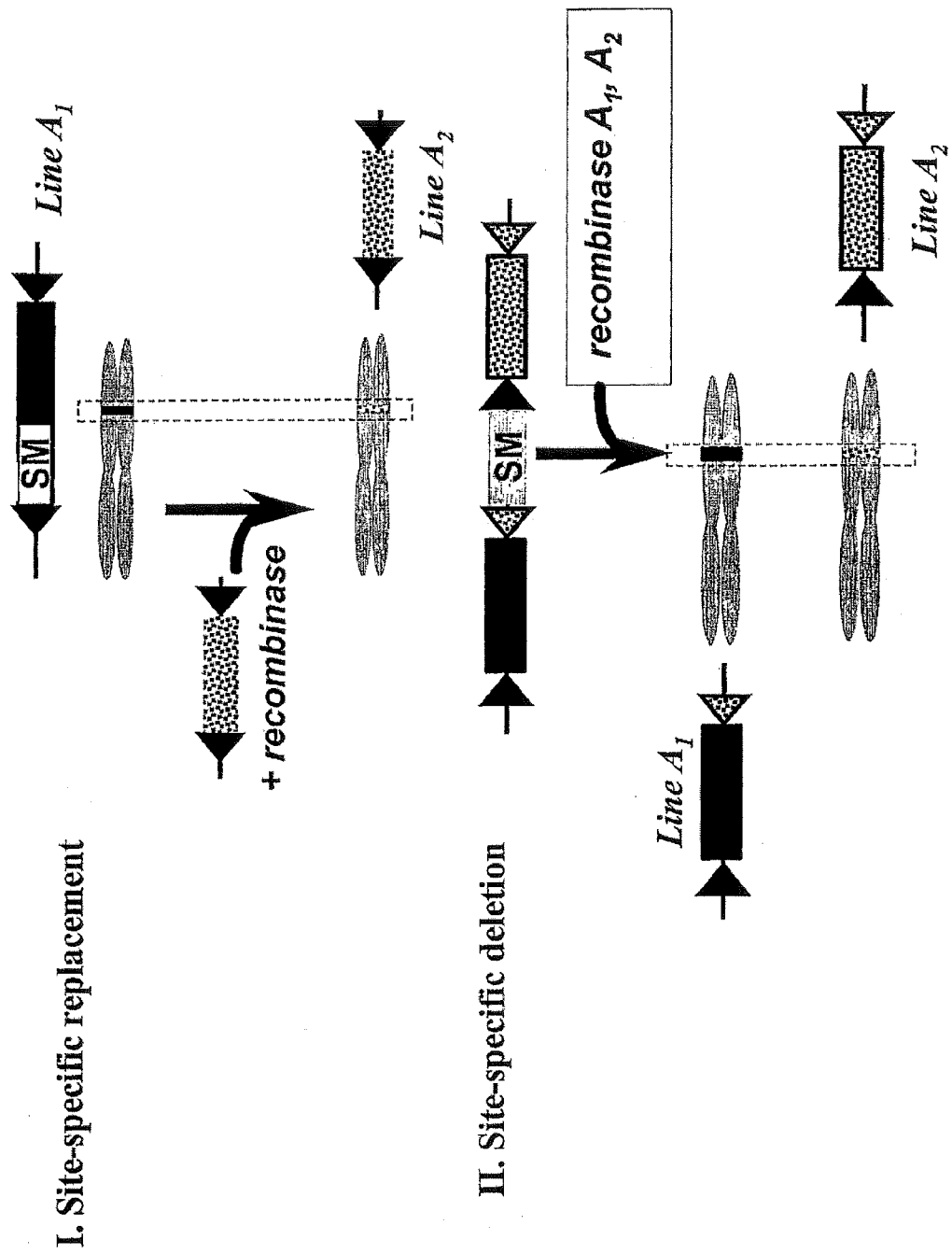

FIG. 15 depicts a possible approaches to generate iso-loci. SM—selectable marker. Filled and dotted triangles show the recombination sites recognised by different site-specific recombinases.

Figure 16:
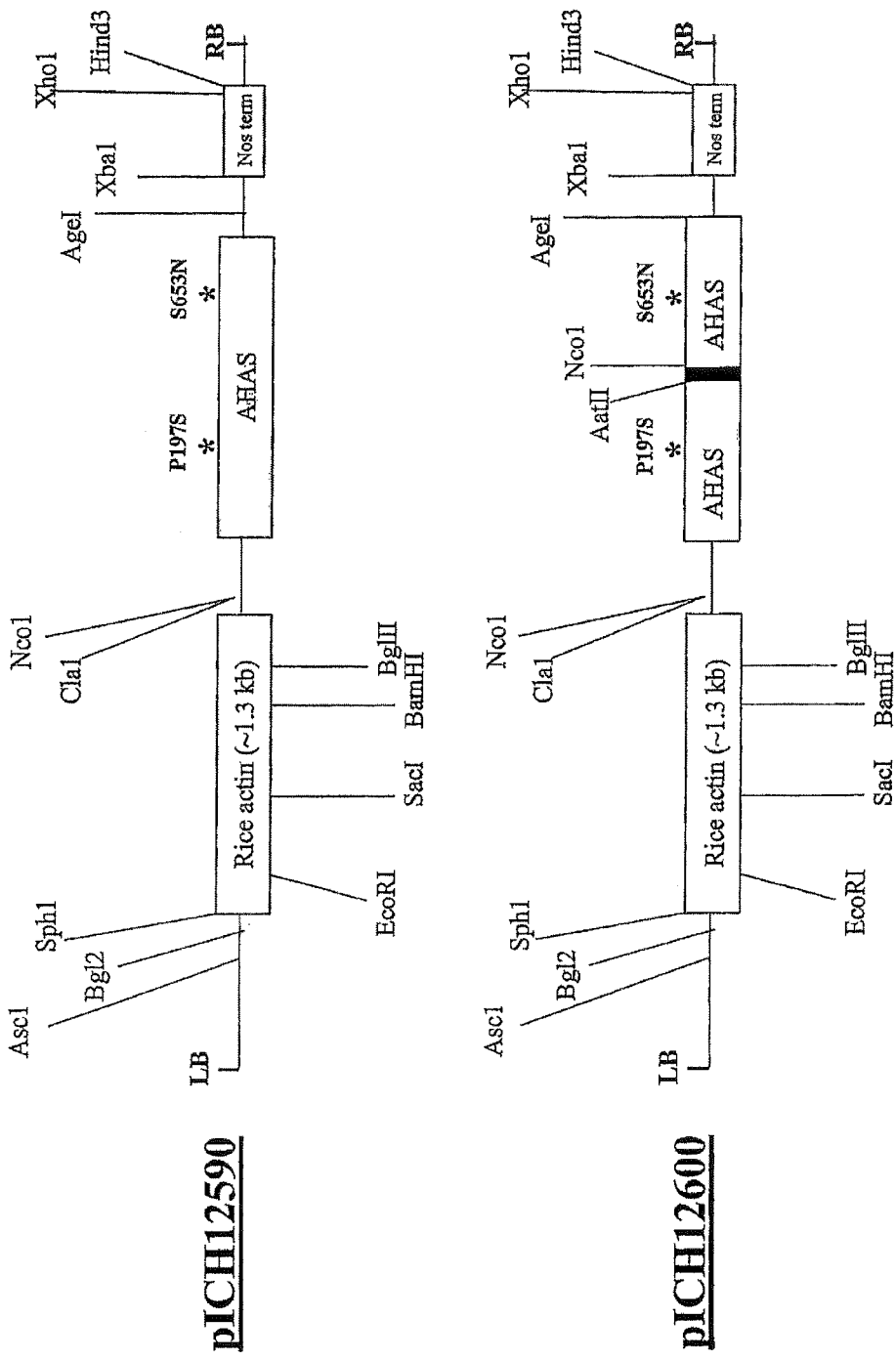

FIG. 16 depicts schematic representations of T-DNA regions of plasmids plCH12590 and plCH12600.

Figure 17:
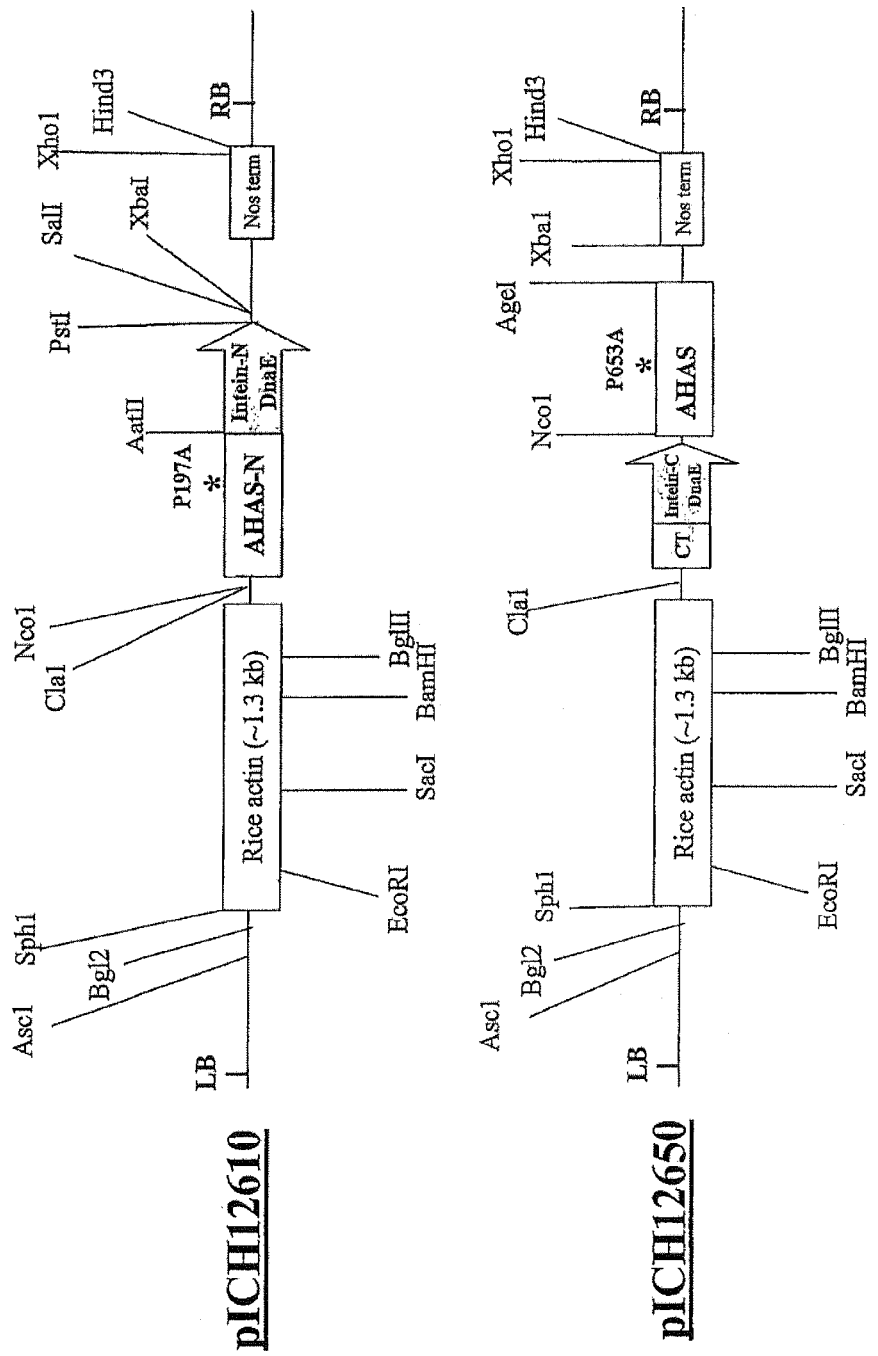

FIG. 17 depicts a schematic representation of the T-DNA regions of plasmids plCH12610 and plCH12650.

Figure 18:
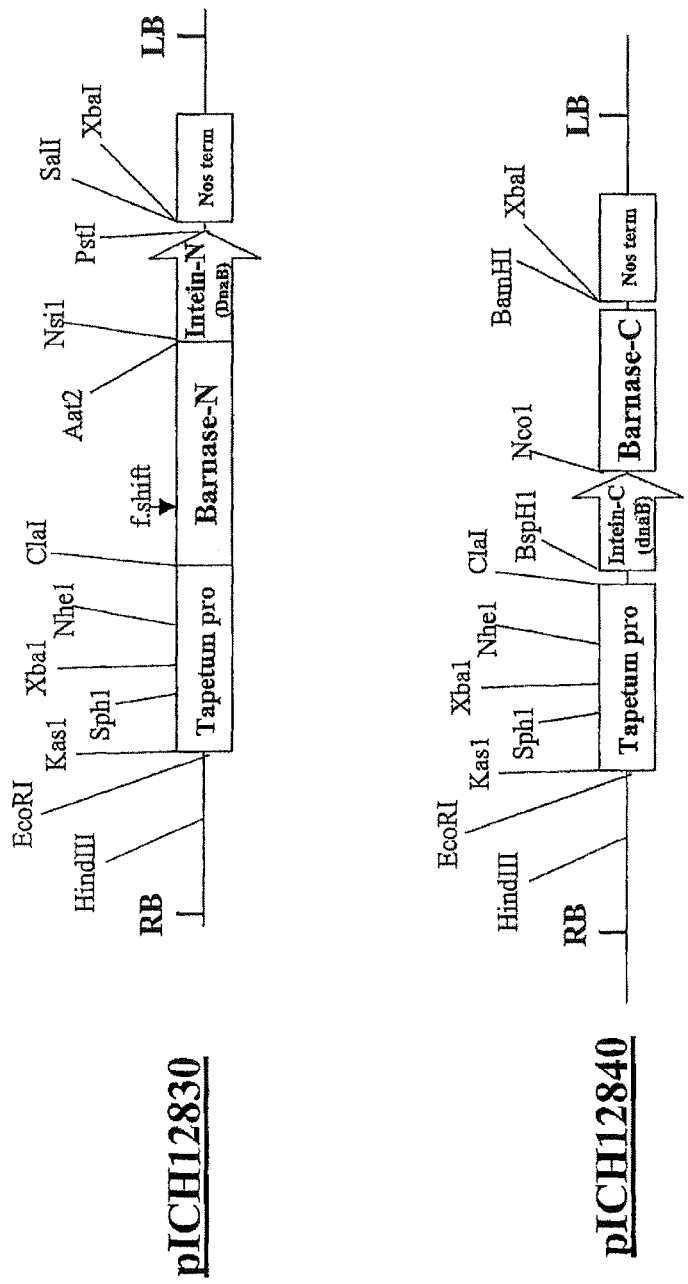

FIG. 18 depicts schematic representations of T-DNA regions for plasmids plCH12830 and plCH12840.

Figure 19:
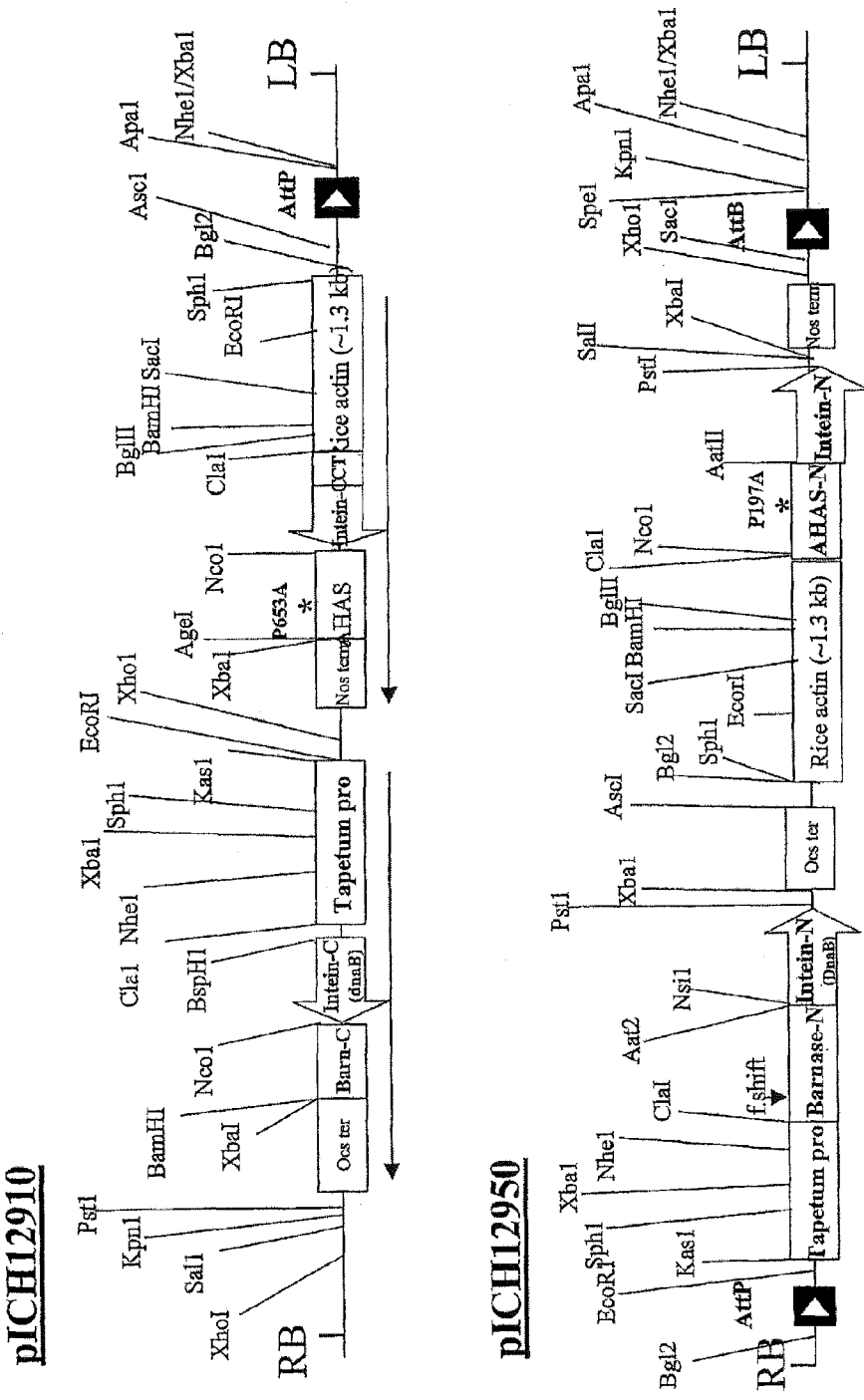

FIG. 19 depicts a schematic rerepresentation of T-DNA regions of constructs plCH12910 and plCH12950.

Figure 20:
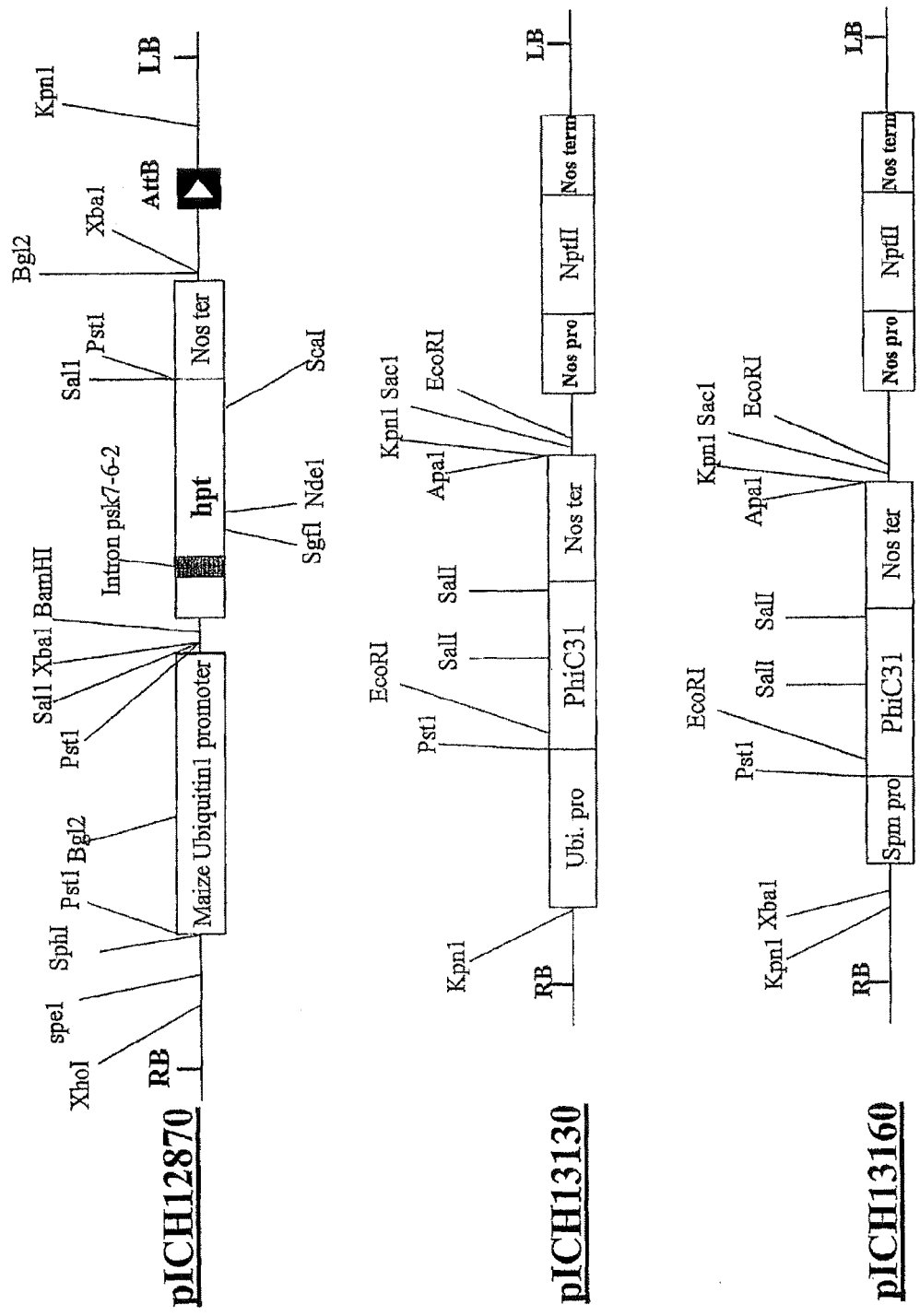

FIG. 20 depicts schematic representation of T-DNA regions of plasmids plCH12870, plCH13130 and plCH13160.

Figure 21:
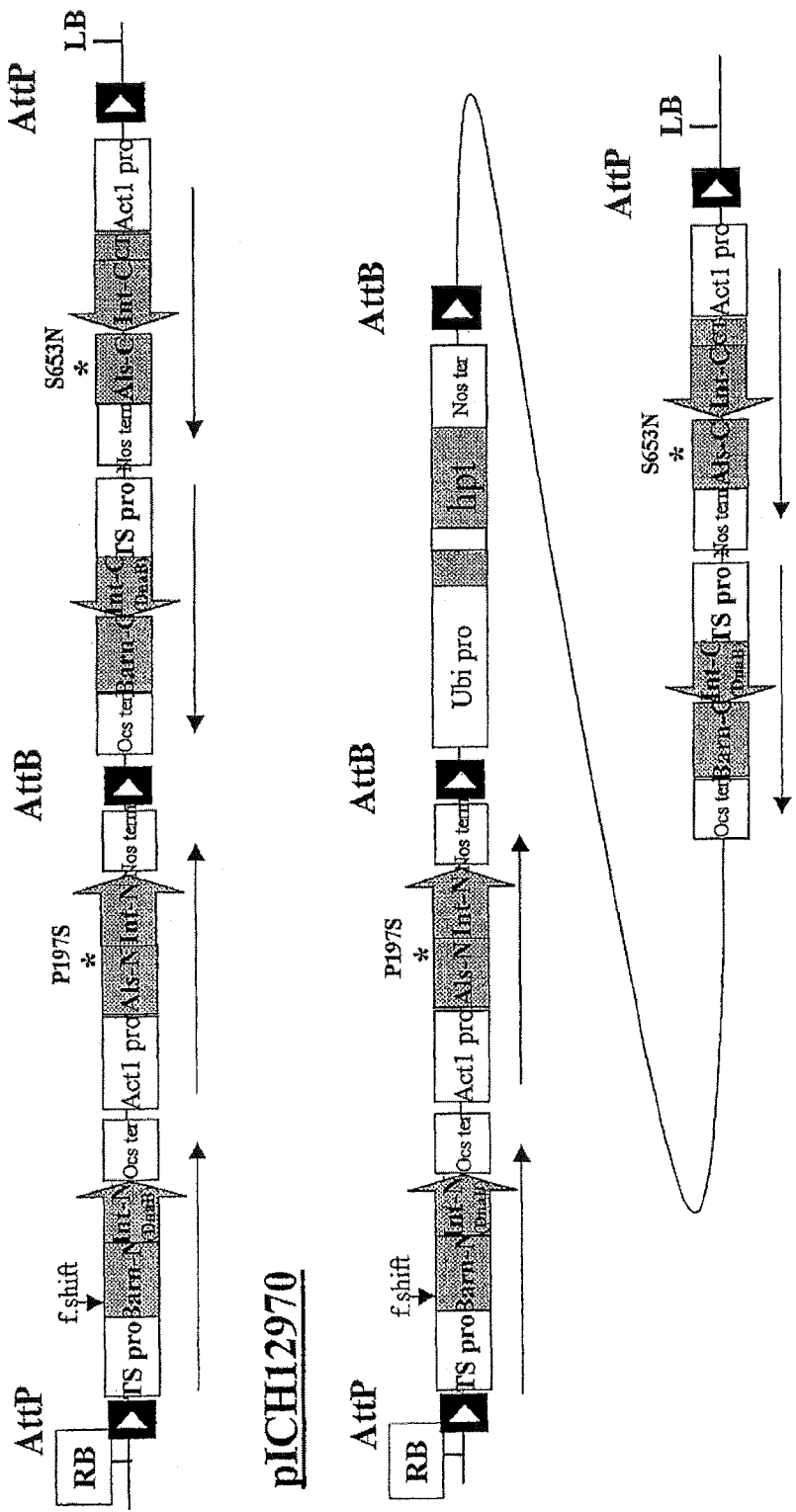

FIG. 21 depicts schematic representation of T-DNA regions of plasmids plCH12960 and plCH12970.

Figure 22:
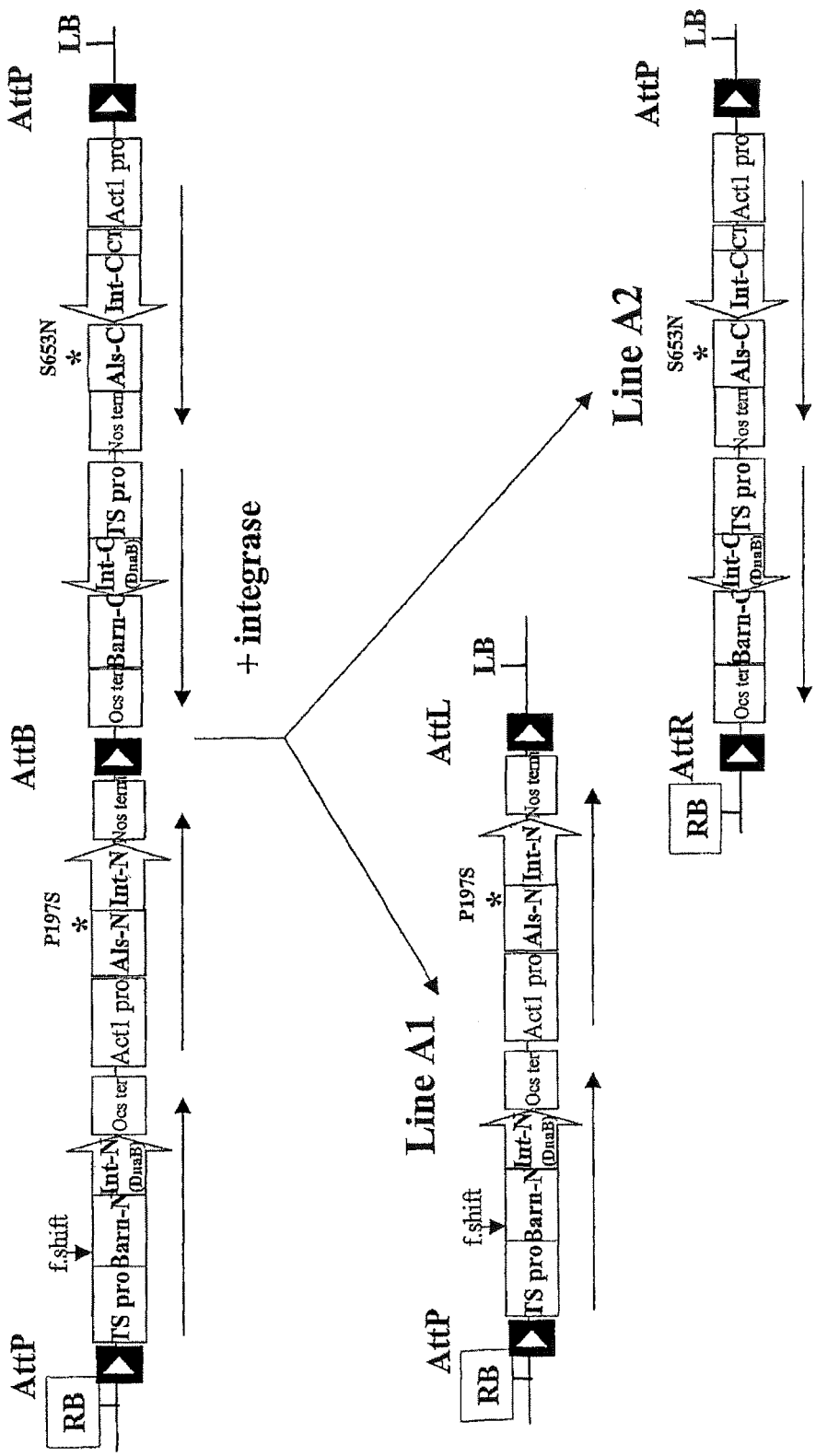

FIG. 22 depicts pro-locus from plCH12960 of line A (top) and splitting of the parent heterologous nucleotide sequence for generating iso-loci from a pro-locus of the T-DNA region of plCH12960. The pro-locus contains AttP and AttB recombination sites of an integrase. Application of the integrase leads to statistic removal of one part of the pro-locus or the other part, thus leading to line A1 and to line A2. Molecular analysis e.g., by PCR is typically be carried out for analysing the recombination result.

DETAILED DESCRIPTION OF THE INVENTION

In this invention, we propose to split the coding sequence of a transgene involved in a trait of interest into two or more fragments that can be bound to each other on the protein level, notably by trans-splicing. Heterologous nucleotide sequences containing these fragments are introduced into the genome of a host plant, preferably into homologous chromosomes, or in the genome and the plastome of a transgenic multi-cellular plant, by hybridising parent plants. Once transcribed and translated, the protein fragments can be assembled by protein trans-splicing, thus forming a functional protein, notably a protein which can provide for the trait of interest. Since the plant breeding process usually involves very specific parental crosses, managing said process of the invention does not pose serious additional problems. Any undesired, spontaneous cross between the transgenic plant of the invention and unwanted organisms effectively disassembles said trait, thus abolishing expression and greatly reducing the chance of functional gene transfer to illicit progeny.

The processes of the invention allow to build mechanisms that would control either the expression of the transgene per se or it could be utilized to control the transgenic variety, as the progeny of any illicit cross is rendered non-viable. Both of these possibilities are inter alia contemplated in our invention.

The invention also allows one skilled in the art to design schemes for selecting primary transformants based on a selectable marker that is effective and operable in the $T_o$ progeny, but fragments or alleles of which, upon subsequent crosses, segregate to different transgenic progeny and thus disappear as a functional selectable marker gene.

Furthermore, the invention allows rapid in vivo assembly of different genes by crossing parents that contain different fragments of a transcriptional unit of interest, thus allowing to swap different functional domains, such as translational enhancers, transit or signal or targeting peptides, purification tags, different functional domains of proteins, etc., by simply crossing plants carrying desired fragments of such a functional gene.

There is a description of a hybrid seeds production system based on barnase gene fragments. If said fragments are expressed in the same cell (anther cells), the protein fragments produced associate, whereby barnase activity is restored, generating male sterility (U.S. Pat. No. 6,392,119; Burgess et al., 2002, *Plant J.*, 31, 113-125). Hybrid seeds produced with the help of said approach recover fertility due to the segregation of barnase gene fragments to different gametes, thus causing the inactivation of the cytotoxic gene responsible for male sterility. However, said system has serious limitations as it is built on protein fragment interactions, not trans-splicing. As the result, said system is temperature-sensitive: temperatures higher than 18° C. may restore fertility of the male-sterile line by dissociating the barnase protein fragments.

In the present invention, protein binding and/or trans-splicing can be achieved by using engineered inteins. Inteins were first identified as protein sequences embedded in-frame within protein precursor and excised during protein maturation process (Perler et al., 1994, *Nucleic Aids Res.*, 22, 1125-1127; Perler, F. B., 1998, *Cell*, 92, 1-4). All information and catalytic groups necessary to perform a self-splicing reaction reside in the intein and two flanking amino acids. The chemical mechanism of protein splicing is described in detail by Perlere and colleagues (1997, *Curr. Pin. Chem. Biol.*, 1, 292-299) and by Shao & Kent (1997, *Chem. Biol.*, 4, 187-194). Inteins usually consist of N- and C-terminal splicing regions and central homing endonuclease region or small linker region. Over 100 inteins are known so far that are distributed among the nuclear and organellar genomes of different organisms including eukaryotes, archaebacteria and eubacteria (www.neb.com/neb/inteins.html). It was shown that intein molecules are capable of trans-splicing. The removal of the central homing endonuclease region does not have any effect on intein self-splicing. This also made possible the design of trans-splicing systems, in which the N-terminal and C-terminal fragments of intein are co-expressed as separate fragments and, when fused to exteins (protein fragments, being ligated together with the help of intein), can perform trans-splicing in vivo (Shingledecker et al., 1998, *Gene*, 207, 187-195). It was also demonstrated with N- and C-terminal segments of the Mycobacterium tuberculosis RecA intein, that protein trans-splicing could take place in vitro (Mills et al., 1998, *Proc. Natl. Acad. Sci. USA*, 95, 3543-3548). This phenomenon was also identified for DnaE protein of *Synechocystis* sp. Strain PCC6803 (Wu et al., 1998, *Proc. Natl. Acad. Sci. USA*, 95, 9226-9231). Two different genes located more than 700 Kb.p. apart on opposite DNA strands encode this protein. It was also shown that two intein sequences encoded by those genes reconstitute a split mini-intein and are able to mediate protein trans-splicing activity when tested in *Echerichia coli* cells. The intein molecule of the same origin (DnaE intein from *Synechocystis* sp. Strain (PCC6803) was used to produce functional herbicide-resistant acetolactate synthase II from two unlinked fragments (Sun et al., 2001, *Appl. Environ. Microbiol.*, 67, 1025-29) and 5-enolpyruvylshikimate-3-phosphate synthase (EPSPS) (Chen et al., 2001, *Gene*, 263, 39-48) in *E. coli*.

Figure 1:
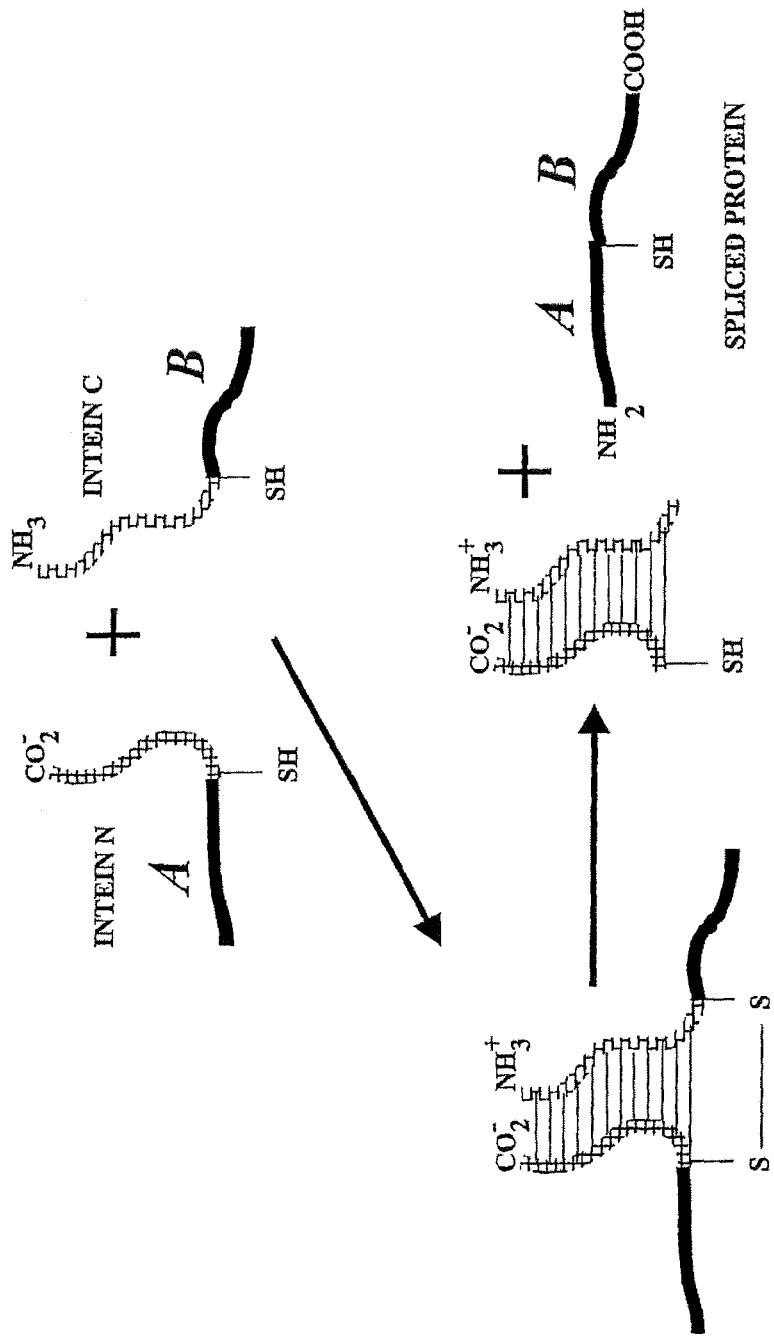
FIG. 1
General scheme of intein mediated trans-splicing resulting in functional protein formation.

The general principle of intein-mediated trans-splicing is shown in FIG. 1.

Figure 2A:
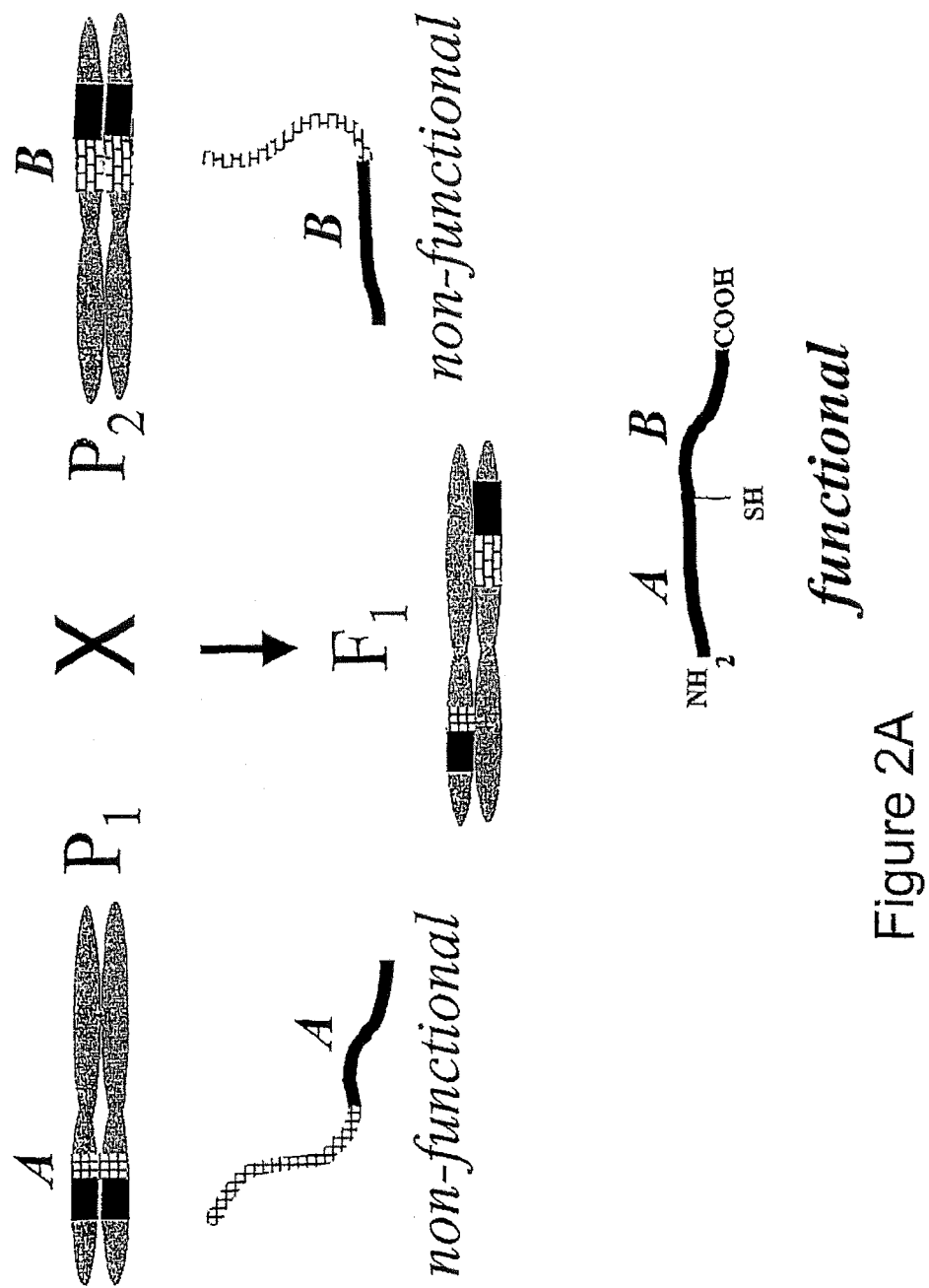
FIG. 2
A—depicts the general principle of the invention, where trans-splicing-mediated formation of a functional protein takes place in cells of hybrid progeny.

Yet another well-established application of inteins is their use for intein-based protein purification systems (for short review see Amitai & Pietrokovski (1999, *Nature Biotechnol.*, 17, 854-855). The self-leavage of intein from its extein releases extein as free protein molecule after the expose to either pH (Wood et al., 1999, *Nature Biotechnol.*, 17, 889-892) or temperature (Sourthworth et al., 1999, *Biotechniques*, 27, 110-114) changes. Alternatively, nucleophilic agents (e.g., DTT) also initiate cleavage, but such agent remains covalently linked to the released protein (Klabunde et al., 1998, *Nat. Struct. Biol.*, 5 31-37). To the best of our knowledge, there is no prior art describing the use of intein-mediated protein trans-splicing for assembly of useful traits in plant cells in a biologically safe and controllable way. The general scheme of trans-splicing mediated trait assembly in $F_1$ progeny is shown in FIG. 2A. None of two parental lines ($P_1$ and $P_2$) has a fully functional linear gene encoding said trait. In contrast, each contains fragments (A or B) of said gene preferably located on homologous chromosomes. As a result of hybridization between $P_1$ and $P_2$, a progeny is generated that provides for a functional trait due to trans-splicing mediated assembly of proteins encoded by fragments A and B. It is evident from said Figure, that only one fourth of $S_1$ progeny derived from self-pollination of the primary hybrid will retain the trait of interest, while the other half will inherit only one out of the two fragments required for providing said trait, and one fourth will have neither A or B. It is also evident, that cross-pollination with any other plant (illicit cross) having none of the fragments A and B will not lead to transmission of the trait, as only one of the two fragments necessary for functional gene is transmitted to each progeny plant.

There are several developed approaches and engineered inteins, which can be used to practice this invention (references cited above). They actually cover the use of all known types of inteins in order to engineer trans-splicing events in eukaryotic cells. In EXAMPLE 3 we describe intein-mediated interaction, which brings together two domains of EPSP synthase providing for herbicide resistance. It demonstrates the possibility of assembling a functional protein dimer by bringing together domains necessary for function without actually protein trans-splicing taking place. Such intein-mediated protein-protein interactions also offer an alternative in some specific cases to provide for a trait without protein trans-splicing.

The processes of the invention may be used as a convenient way of assembling a desired sequence and/or expression unit from different parts in trans, using as modules or building blocks different transgenic plants. Their hybrid progeny would put together modules inherited from different parents through engineered intein-mediated trans-splicing. It is possible to form a trait of interest by choosing the appropriate pair of transgenic parents containing required modules, very much like by choosing an appropriate pair of parental plants for producing high value hybrid seeds in traditional breeding. Examples of such modules include different signal peptides, binding domains (e.g., cellulose, pectin, starch binding domains, etc.), retention signals, compartmentalization signals, activation domains, domains with enzymatic activities, affinity tags, regulatory sequences, different genes of interest and parts thereof. In this regard the trait of interest is understood broadly and includes not only a functional protein with a specific capabilities but in particular a protein targeted to a specific compartment or macromolecular matrix, or protein engineered for subsequent isolation/purification.

Additionally, trans-splicing on protein level gives many important advantages which cannot be provided by RNA trans-splicing. Said advantages are the result of the following features:

a) intein-mediated trans-splicing directly results in the protein molecule, while ribozyme-mediated trans-splicing forms RNA molecule, which, in most cases, shall be translated into the protein, thus restricting the choice of cellular/intercellular compartment for said trans-splicing;

b) targeting of intein-mediated trans-splicing components provides for a lot of flexibility, as we are dealing with protein molecules, while targeting of RNA molecules is preferably restricted to cytosol;

c) engineered inteins, in addition to said above, allow for regulating trans-splicing by changing pH, temperature or nucleophilic agents.

d) Inteins engineered for trans-splicing interact with high efficiency and can bring together protein domains that will provide for enzymatic activity following such interaction even without the covalent link (trans-splicing) taking place.

Such diversity in the choice of parameters for regulation of intein-mediated trans-splicing or interaction (combination of compartmentalization choices with modulation of abiotic parameters) gives flexibility and remarkable variability of choices compared to the RNA-trans-splicing approach.

However, all these potential applications have a limited value without knowing how to achieve the most preferable location of said heterologous fragments relative to each other, preferably on nuclear chromosomes.

Figure 2B:
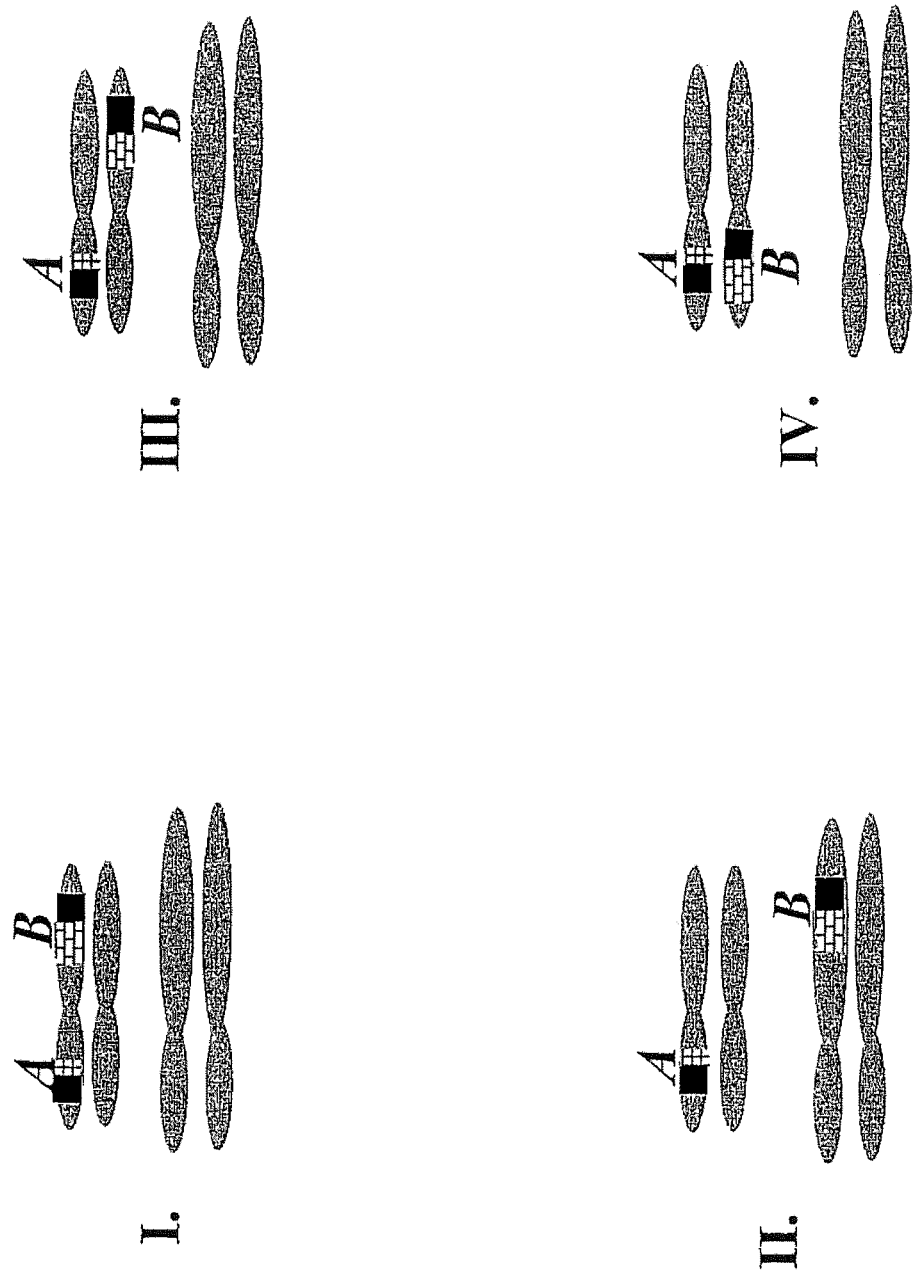

According to this invention, said fragments are on different homologous chromosomes (FIG. 2B, case III and IV). In case III, self-progeny can inherit the trait, but said trait will not be inherited by progeny resulting from crossing with plants possessing neither of said fragments if meiotic crossing-over is neglected or absent. Meiotic recombination between the two homologous chromosomes may, however, physically link said fragments A and B. The frequency of such recombination events directly depends from the relative distance between said fragments on the two homologous chromosomes.

In order to suppress physical linkage of said fragments by meiotic recombination, said fragments are preferably positioned at short relative distance on homologous chromosomes or, most preferably, at the same locus on the homologous chromosomes (FIG. 2B, case IV), thus minimizing the frequency of meiotic recombination between such fragments practically to zero. There are different technical solutions to achieve this most preferable allelic location of said fragments. Said fragments can be integrated at the same locus in pre-engineered integration site by means of site-specific recombination (FIG. 2C). Examples of such systems include the Cre-Lox system from bacteriophage P1 (Austin et al., 1981, Cell, 25, 729-736), the Flp-Frt system from *Saccharomyces cerevisiae* (Broach et al., 1982, Cell, 29, 227-234), the R-RS system from *Zygosaccharomyces rouxii* (Araki et al., 1985, *J. Mol. BioL,* 182, 191-203) and the integrase from the *Streptomyces* phage PhiC31 (Thorpe & Smith, 1998, *Proc. Natl. Acad. Sci.,* 95, 5505-5510; Groth et al., 2000, *Proc. Natl. Acad. Sci.,* 97, 5995-6000).

Figure 2D:
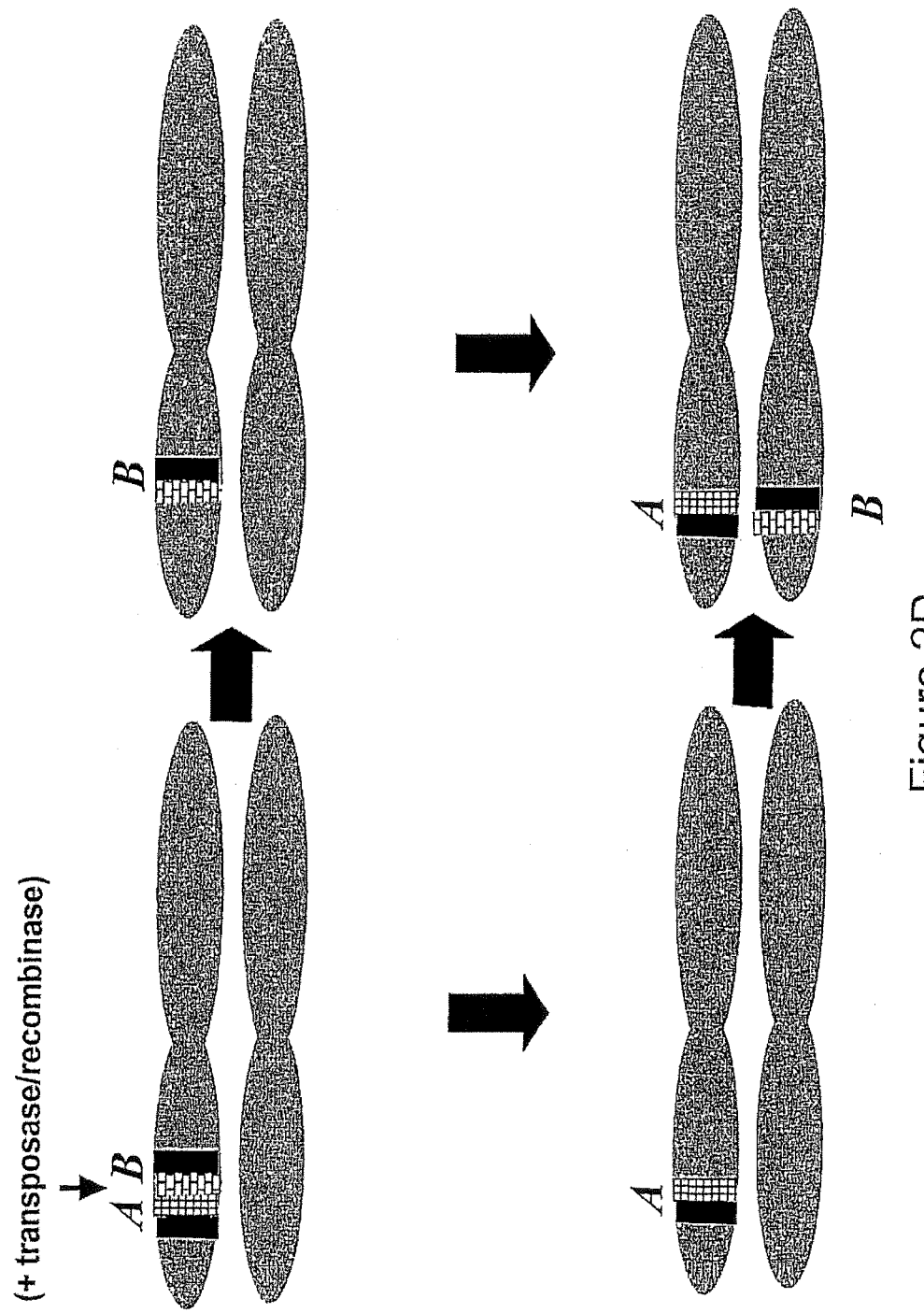

Said fragments A and B can be integrated within chromosomal DNA as one construct AB (FIG. 2D). The design of the construct should allow selective removal of one of the DNA fragments (A or B) using mechanism of controllable DNA rearrangement (excision or transposition), thus generating progeny containing either fragment A or fragment B in the same locus, bringing together both fragments or their transcripts by crossing plants possessing only one of said fragments or both fragments, but only one of required transcripts, will lead to expressing a trait of interest.

An example of said controlled DNA rearrangement is to flank fragments A and B with sequences recognized by different site-specific recombinases and, upon provision of the respective recombinase, to selectively remove either fragment A or fragment B. Alternatively, the placement of a transcription initiation region (promoter) flanked by inverted recombination sites just between said fragments can lead to selective transcription of either fragment A or B depending on said transcription initiation region orientation. The inversion of orientation (but not excision) of said region can be induced by exposure to the recombinase source. As the result, it is possible to achieve selective transcription of either fragment A or fragment B without (physically) removing them, but using DNA inversion as a switch. However, the case of selective expression of one heterologous DNA fragment in the presence of both heterologous DNA sequences at the same location is not among the preferred embodiments of this invention, as this may not provide the required level of control over trait expression and movement.

Figure 2E:
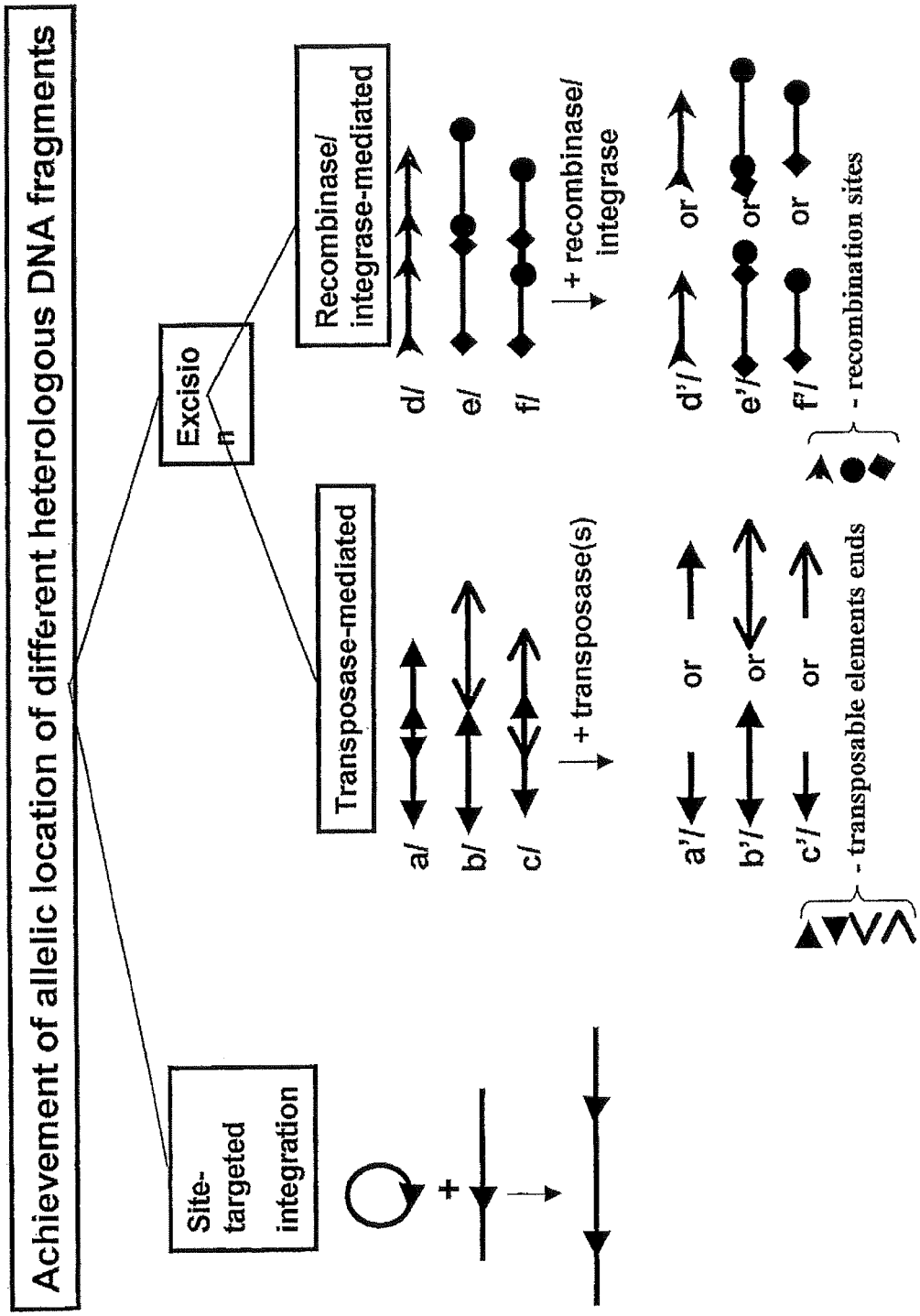

An important embodiment of said controlled DNA rearrangement comprises the use of transposition, wherein one of the fragments, for example fragment B, is located and transcribed within a non-autonomous transposable element, and its excision from the construct will trigger transcription of fragment A. Excision of the transposon may or may not be followed by its reinsertion elsewhere and progeny can be selected that contains fragment A or B only. Taking into the consideration that most of transposon reinsertions occur at positions closely linked to the donor site (Jones et al., 1990, *Plant Cell,* 2, 701-707; Carroll et al., 1995, *Genetics,* 139, 407-420), the chance of selecting progeny containing fragments A and B linked in repulsion (on different chromosomes of chromosome pair) is very high. FIG. 2E summarizes a variety of approaches for achieving an allelic location of the first and the second heterologous nucleotide sequences including site-targeted integration and excision of said fragments. Transposase-mediated or recombinase-mediated excision of said fragments can be achieved with the help of one (FIG. 2E, a/, a'/, d/ and d'/) or two different transposon or recombinase systems (FIG. 2E, b/, b'/, c/, c'/, e/, e'/, f/ and f'/). The use of two different systems is preferred. The use of two different transposon systems is more preferred. The use of two different transposon systems with overlapping transposon ends is the most preferred (c/ and c'/) embodiment.

The description of construct design for trait assembly through intein-mediated protein trans-splicing (FIGS. 3, 4) or intein-mediated protein fragment interaction (FIG. 5) is described in examples 1, 2 and 3, respectively. The use of site-specific recombination or transposition allows positioning of the first and the second heterologous nucleotide sequence from a construct at the same loci on homologous chromosomes, which is most favorable for controlled distribution of a trait of interest to cross-progeny. A schematic representation of such a construct (in the T-DNA of a vector for Agrobacterium-mediated transformation) and excision of one or the other of said heterologous nucleotide sequences with the use of two different plant transposon systems (Spm/dSpm and Ac/Ds) is shown in FIG. 6. Here, the two components (heterologous nucleotide sequences) of intein trans-splicing system are located on the same T-DNA (FIG. 6A), but flanked by different transposon ends (Ds or dSpm) recognized by different transposases, Ac or Spm, respectively. In brief, the construct in the T-DNA has two non-autonomous transposable elements with overlap at one end. The exposure of a plant or of plant cells carrying such construct to a Spm or Ac transposase source, will lead to the excision of the fragment flanked by the Ds sequences (exposure to Ac transposase), or of the fragment flanked by the dSpm sequences (exposure to Spm transposase). The resulting T-DNA structures are shown in FIGS. 6, B and C, respectively. These resulting constructs are stable even in the presence of Spm (in case of B) or Ac (in case of C) transposase, as one of the two ends of the non-autonomous transposon required for transposition, is excised together with the other non-autonomous transposable element. Such stabilization of the remaining transposable element is very useful, especially in the case of plants carrying an endogenous transposase source, e.g., corn in case of Ac or Spm transposase. The scheme of transposon-based selective removal of unwanted DNA fragments is shown in FIG. 7. Here, transposition also leads to removal of other unwanted sequences, e.g., a selectable (SM) and a counter-selectable marker (CSM) genes, thus facilitating the screening for plants/plant cells carrying only the required heterologous nucleotide sequence (hDNA 1 or 2). One of the possible schemes for generating plants with different heterologous nucleotide sequences in allelic relation is shown in FIG. 8. These examples with selectable marker genes is not limited to genes conferring antibiotic or herbicide resistance. An extensive list of such genes is shown below. Examples of some counter-selectable marker genes applicable to plant systems, bacterial codA and cytochrome P-450 (Kopreck et al., 1999, *Plant J.,* 19, 719-726; Gallego et al., 1999, *Plant Mol. Biol.,* 39, 83-93), are described in a number of papers, including their application in combination with transposon systems (Tissier et al., 1999, *Plant Cell,* 11, 1841-1852).

There are well studied transposon systems for plants that are abundantly described in the literature (for reviews see: Dean et al., 1991, *Symp. Soc. Exp. Biol.,* 45, 63-75. Walbot, V., 2000, *Plant Cell Physiol.,* 41, 733-742; Fedoroff, N., 2000, *Proc. Natl. Acad. Sci. USA.,* 97, 7002-7007). The Ac/Ds (Briza et al., 1995, *Genetics,* 141, 383-390; Rommens et al., 1992, *Plant Mol. Biol.,* 20, 61-70; Sundaresan et al., 1995, *Genes Dev.,* 9 1797-810; Takumi, S. 1996, *Genome,* 39, 1169-1175; Nakagava et al., 2000, *Plant Cell PhysioL.,* 41, 733-742) and Spm/dSpm (Cardon et al., 1993, *Plant J.* 3 :773-784; Aarts et al., 1995, *Mol. Gen. Genet.,* 247, 5555-64; Tissier et al., 1999, *Plant Cell,* 11, 1841-1852) systems are well established for transposon tagging in many plant species including many crop plants, and their adoption for practicing this invention is routine for those familiar with the art. This invention is not limited to Ac/Ds and Spm/dSpm systems. Actually, any transposon system active in plants employing a "cut-and-paste" (excision and reinsertion) mechanism for its transposition can be employed in this invention.

In the examples, we used *Agrobacterium*-mediated T-DNA delivery in plant cells, whereby said T-DNA contains said first and/or said second heterologous nucleotide sequence as a vector. Different methods may be used for the delivery of vectors into plant cells such as direct introduction of said vector into cells by means of microprojectile bombardment, electroporation or PEG-mediated transformation of protoplasts. Agrobacterium-mediated plant transformation is preferred. Thus, DNA may be transformed into plant cells by various suitable technologies such as by a Ti-plasmid vector carried by *Agrobacterium* (U.S. Pat. No. 5,591,616; U.S. Pat. No. 4,940,838; U.S. Pat. No. 5,464,763), particle or microprojectile bombardment (U.S. Pat. No. 5,100,792; EP 00444882B1; EP 00434616B1). In principle, other plant transformation methods can also be used e.g., microinjection (WO 09209696; WO 09400583A1; EP 175966B1), electroporation (EP00564595B1; EP00290395B1; WO 08706614A1), etc. The choice of the transformation method depends on the plant species to be transformed. For example, microprojectile bombardment may be preferred for monocots transformation, while for dicots, *Agrobacterium* mediated transformation gives generally better results.

The trans-splicing system described in our invention comprises two fragments, which are provided in trans and are located in allelic positions on homologous chromosomes. This means that our system is better controlled and safer, e.g., it can have zero trait expression level in the uninduced state and zero trait transfer during cross-pollination with other plants.

Genes of interest, or fragments thereof, that can be expressed, in sense or antisense orientation, using this invention include: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/metabolism enzyme, glutamine synthase, plant osmotin, 2S albumin, thaumatin, site-specific recombinase/integrase (FLP, Cre, R recombinase, int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CryIC toxin, delta endotoxin, polyopeptide toxin, protoxin etc.), insect specific toxin AaIT, cellulose degrading enzymes, E1 cellulase from *Acidothermus cellulolicus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, Brassica AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, Umbellularia californica C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, 6-desaturase, protein having an enzymatic activity in the peroxysomal-oxidation of fatty acids in plant cells, acyl-CoA oxidase, 3-ketoacylCoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, ribozyme, protein having posttranslational cleavage site, protein fusion consisting of a DNA-binding domain of Gal4 transcriptional activator and a transcriptional activation domain, a translational fusion of oleosin protein with protein of interest capable of targeting the fusion protein into the lipid phase, DHPS gene conferring sulfonamide resistance, bacterial nitrilase, 2,4-D monooxygenase, acetolactate synthase or acetohydroxyacid synthase (ALS, AHAS), polygalacturonase, bacterial nitrilase, fusion of amino terminal hydrophobic region of a mature phosphate translocator protein residing in the inner envelope membrane of the plastid with protein of interest to be targeted into said membrane etc.

Any human or animal protein can be expressed, notably in hybrid seeds and plants grown therefrom, using the trans-splicing system of the invention. Examples of such proteins of interest include inter alia the following proteins (pharmaceutical proteins): immune response proteins (monoclonal antibodies, single chain antibodies, T cell receptors etc.), antigens, colony stimulating factors, relaxins, polypeptide hormones, cytokines and their receptors, interferons, growth factors and coagulation factors, enzymatically active lysosomal enzyme, fibrinolytic polypeptides, blood clotting factors, trypsinogen, 1-antitrypsin (AAT), as well as function-conservative proteins like fusions, mutant versions and synthetic derivatives of the above proteins.

The process of the invention may further comprise expressing a gene encoding a post-transcriptional gene silencing (PTGS) suppressor protein or a function-conservative variant or fragment thereof in a plant for suppressing PTGS of said transgenic coding sequence. Said PIGS suppressor protein gene or function-conservative variant or fragment thereof may be provided to a plant on the same vector carrying said transgenic coding sequence or on an extra vector. Said PIGS suppressor protein is preferably of viral or plant origin. Examples of PIGS suppressor proteins are potato virus X p25 protein, African cassava mosaic virus AC2 protein, rice yellow mottle virus P1 protein, tomato bushy stunt virus 19K protein, rgs CAM or a function-conservative variant or fragment of one of these proteins. Said function-conservative variant or fragment preferably has a sequence identity of 75%, preferably at least 75%, to one of the above proteins. Details on PIGS suppressor proteins and their use can be found in WO0138512.

The invention further provides a transgenic multi-cellular plant organism expressing a trait of interest, said organism having a controlled distribution of said trait to progeny, wherein expression of said trait involves production of a protein molecule by trans-splicing of polypeptide fragments, whereby said polypeptide fragments are encoded on different heterologous nucleotide sequences. Said different heterologous nucleotide molecules are incorporated on homologous chromosomes of this plant. Preferably, said polypeptides form, after trans-splicing or other specific polypeptide interaction, a heterologous protein.

The invention further comprises parts or products of the transgenic plant organisms of the invention and plant seeds obtained by said hybridising. Further, plants or plant material (notably seeds or cell thereof) obtained or obtainable according to step (i) or step (ii) of claim 1. Moreover, vectors for performing the process of the invention are provided, whereby said vectors comprise the parent heterologous nucleotide sequence as defined herein. Further, vectors for performing the process of the invention are provided, notably those shown in the figures and those used in the examples of the invention.

In summary, we propose trait/gene lock systems that are based on a modular principle of providing for trait by assembly of non-functional protein fragments or sub-units into a functional protein. Such systems rely on genetic control of the trait of interest by at least two loci that segregate independently during crosses, especially during illicit sexual crosses or in the process of a hypothetical horizontal transfer. Based on the present invention, such locks rely on functional protein assembly when the necessary loci are present and expressed in the same cell or in the same organism. Based on our invention, such gain of function is preferably achieved through protein trans-splicing. It was shown before, that intein-mediated trans-splicing allows for functional protein assembly from non-functional protein fragments in vitro (Mills et al., 1998, Proc. Natl. Acad. Sci. USA, 95, 3543-3548), as well as in different microorganisms (Shingledecker et al., 1998, Gene, 207, 187-195; Wu et al., 1998, Proc. Natl. Acad. Sci. USA, 95, 9226-9231; Sun et al., 2001, Appl. Environ. Microbiol, 67, 1025-29; Chen et al., 2001, Gene, 263, 39-48). The present invention, however, is not limited to protein trans-splicing as the mechanism of functional protein assembly. Such functionality leading to a trait of interest can be achieved also by providing different subunits of a heteromeric protein, as long as (a) the functionality of the protein of interest depends on the presence of the subunits in questions and (b) the genes for components of are encoded in such a way as to allow for preventing illicit crosses.

The invention also allows to assemble sequence coding for a protein from modules of e.g., signal peptides, binding domains, retention signals, trans-membrane signals, activation domains, domains with enzymatic activities, affinity tags, and regulatory sequences. Such a modular approach makes it simple to find an optimal expression cassette for a specific purpose or for finding an optimal secretory or transit peptide for a specific gene to be over-expressed and accumulated in the cell or a specific compartment thereof. It can be a valuable tool for functional genomics and proteomics studies. A library of plants may e.g., be created, whereby each member of the library contains a particular module (e.g., a specific signal peptide) of one of the above module classes e.g., as said first fragment. The second fragment will then code for a protein of interest. Following said hybridizing, the sequence of said protein is linked to said module by trans-splicing.

Protein splicing, can occur only between at least two genetically designed loci, it occurs in vitro with a very high efficiency, thus allowing for quantitative splicing of parental polypeptides, and it can occur between polypeptides that are encoded in different organellar genomes, such as nuclear genome, plastid or mitochondrial genomes, or extrachromosomal episomes, as long as the translated polypeptides are targeted to the same organelle.

It should be mentioned that the technology described herein can similarly be applied to multi-cellular animals. Humans are excluded.

EXAMPLES

Example 1

Intein-Mediated Trans-Splicing of GFP

The 5' end of the GFP gene was amplified by PCR using primers 35spr3 (cgc aca atc cca cta tcc ttc g) and gfppr8 (ctg ctt gtc ggc cat gat ata g) from plasmid pICH5290 (35S-omega leader-gfp coding sequence-ocs terminator in Icon Genetics binary vector pICBV1 containing BAR for plant selection, FIG. 9). A DNA fragment containing the C-terminal end of the DNAE intein from *Synechocystis* was amplified by PCR from genomic DNA (Strain PCC6803 from the American Type Culture Center) using primers gfpintel (cta tat cat ggcc gac aag cag aag ttt gcgg aatat tgcc tcagt) and intepr2 (ttt gga tcc tta ttt aat tgt ccc agc gtc aag). A fusion of the GFP and intein fragments was made by PCR using previously amplified DNA fragments and primers 35Spr3 and intepr2 for the second amplification. The PCR product was cloned as a Nco1-BamHI fragment in pICBV16 (Icon Genetics binary vector with NptII for plant selection FIG. 11; other binary vectors may also be used). The resulting plasmid, pIC5'gfpint (FIG. 3), was checked by sequencing.

The 3' end of the GFP gene was amplified by PCR using primers gfppr9 (aag aac ggc atc aag gtg aac) and nosterrev (tca tcg caa gac cgg caa cag g) from plasmid pICH5290. A DNA fragment containing the N-terminal end of the DNAE intein from *Synechocystis* was amplified by PCR from genomic DNA using primers intepr3 (ttt cca tgg tta aag tta tcg gtc gtc) and integfp2 (gtt cac ctt gat gcc gtt ctt aca aft ggc ggc gat cgc ccc att). A fusion of the intein and GFP fragments was made by PCR using previously amplified DNA fragments and primers intepr3 and nosterrev for the second amplification. The PCR product was cloned as a Nco1-BamHI fragment in pICBV16. The resulting plasmid, pICintgfp3' (FIG. 3) was checked by sequencing.

The GFP gene product that results from intein-mediated trans-splicing contains six additional amino acids (KFAEYC) between amino acids 156 (K) and 157 (Q). This insertion was shown to not significantly affect GFP fluorescence (Ozawa et al., 2001, *Anal. Chem.*, 73, 5866-5874). pIC5'gfpint and pICintgfp3' were transformed in *agrobacterium* strain GV3101 by electroporation. Both constructs were co-expressed transiently in *Nicotiana benthamiana* leaves using *Agrobacterium*-mediated transient expression (Vaquero et al., 1999, *Proc. Natl. Acad. Sci. USA*, 96, 11128-11133). GFP fluorescence was detected when both constructs were co-expressed but not when constructs were expressed individually.

Both constructs were also transformed in *Arabidopsis thaliana* (Col-0) plants as described by Bent et al. (1994, *Science*, 285, 1856-1860). Seeds were harvested three weeks after vacuum-infiltration, and germinated and screened for transformants on plates containing 50 mg/L Kanamycin. The same constructs were also used for *Agrobacterium*-mediated leaf disc transformation of *Nicotiana tabacum* plants (Horsh et al., 1985, *Science*, 227 1229-1231) using 50 mg/L of Kanamycin for selection of transformants. In tobacco and *Arabidopsis*, GFP fluorescence could not be detected in transformants with either construct alone, but was detected in $F_1$ plants containing both transgenes.

Example 2

Intein-Mediated Trans-Splicing of EPSP

The enzyme 5-enolpyruvylshikimate 3-phosphate synthase (EPSP synthase) catalyses the formation of 5-enolpyruvylshikimate 3-phosphate from phosphoenolpyruvate and shikimate 3-phosphate. EPSP synthase is the cellular target of the herbicide glyphosate (N-phosphonomethylglycine). A mutant allele of the aroA gene of *Salmonella typhimurium* with a P101S mutation encodes an EPSP synthase with decreased activity to glyphosate. Expression of this gene in plants confers resistance to glyphosate (Comai et al, 1985, *Nature*, 317, 741-744). The 5' end of the mutant EPSP gene was amplified by PCR from *Salmonella typhimurium* genomic DNA (prepared from strain ATCC 39256 from the American Type Culture Center) using primers epsp1 (tctcc atg gaa tcc ctg acg tta caa c) and epsppr2 (acc tgg aga gtg ata ctg ttg). A DNA fragment containing the C-terminal end of the DNAE intein from *Synechocystis* was amplified by PCR from pIC5'gfpint using primers intepr5 (caa cag tat cac tct cca ggt aag ttt gcg gga tat tgc ctc agt) and intepr2. A fusion of the EPSP and intein fragments was made by PCR using previously amplified DNA fragments and primers epsp1 and intepr2. The PCR product was cloned as a Nco1-BamHI fragment in pICH5300 (Icon Genetics binary vector with BAR gene for plant selection, FIG. 10). The resulting plasmid, pIC5'epsp-int (FIG. 4), contains the EPSP-N-intein fusion under control of the 35S promoter, fused translationally to an artificial chloroplast transit peptide (massm lssaav vatra saaqa smvap ftglk saasf pvtrk qnnld itsia snggr vqca). pIC5'epsp-int was checked by sequencing.

The 3' end of the EPSP gene was amplified by PCR from *Salmonella typhimurium* genomic DNA using primers epsp3 (cgc tat ctg gtc gag ggc gat) and epsp4 (cgg ggatcc tta ggc agg cgt act cat tc). A DNA fragment containing the N-terminal end of the DNAE intein from *Synechocystis* was amplified by PCR from pICintgfp3' DNA using primers intepr3 and intepr6 (atc gcc ctc gac cag ata gcg gga ttt gtt aaa aca att ggc ggc gat). A fusion of the intein and EPSP fragments was made by PCR using previously amplified DNA fragments and primers intepr3 and epsp4. The PCR product was cloned as a Nco1-BamHI fragment in pICH5300. The resulting plasmid, pICint-epsp3' (FIG. 4), contains the C-intein-EPSP fusion under control of the 35S promoter, fused translationally to the artificial chloroplast transit peptide. pICint-epsp3' was checked by sequencing.

The EPSP gene product that results from intein-mediated trans-splicing contains ten additional amino acids (KFAEY-CFNKS) between amino acids 235 (G) and 236 (R). It has been previously shown that this position in the EPSP gene can accommodate insertions of at least 5 to 12 amino acids without compromising gene function (Chen et al., 2001, *Gene*, 263, 39-48).

pIC5'epsp-int and pICint-epsp3' were transformed in agrobacterium strain GV3101 by electroporation. Both constructs were transformed in *Arabidopsis thaliana* (Col-0) plants as described by Bent et al. (1994, *Science*, 285, 1856-1860). Seeds were harvested three weeks after vacuum-infiltration, germinated in soil and screened for transformants by spraying several times with a solution containing 50 mg/L phosphinothricin (PPT).

The same constructs were also used for *Agrobacterium*-mediated leaf disc transformation of *Nicotiana tabacum* plants (Horsh et al., 1985, *Science*, 227, 1229-1231) using 10 mg/L of PPT for selection of transformants. Transformants were checked for EPSP gene activity by spraying plants with a commercial formulation of glyphosate (N-phosphonomethylglycine). For both Arabidopsis and tobacco, transformants containing either constructs alone did not exhibit glyphosate resistance. F1 plants containing both constructs were resistant to glyphosate.

Example 3

Intein-Mediated Assembly of Functional EPSP without Trans-Splicing pIC5'epsp-intM is similar to construct pIC5'epsp-int but differ at the junction EPSP-N intein by the addition of 4 native N extein amino acids instead of five and by the first N intein amino acid which was changed from Cys to Ala. PIC5'epsp-intM was made following the same strategy as for PIC5'epsp-int except that primer intepr7 (caa cag tat cac tct cca ggt ttt gcg gaa tat gcc ctc agt ttt ggc ac) was used instead of primer intepr5.

PlCint-epsp3'M is similar to construct PlCint-epsp3' but differ at the junction C intein-EPSP by the addition of 3 C extein amino acids instead of five, the first one mutated from Cys to Ala and the two other native, and by the last C intein amino acid which was changed from Asn to Ala. PlCint-epsp3'M was made following the same strategy as for PlCint-epsp3' except that primer intepr8 (atc gcc ctc gac cag ata gcg gtt aaa agc agc ggc ggc gat cgc ccc att g) was used instead of primer intepr6.

The three mutated amino acids completely prevent intein mediated trans-splicing but do not prevent association of the N and C intein fragments ((Chen et al., 2001, *Gene*, 263, 39-48). pIC5'epsp-intM and plCint-epsp3'M were transformed in *agrobacterium* strain GV3101 by electroporation. Both constructs were transformed in *Arabidopsis thaliana* (Col-0) and tobacco as described above. Primary transformants were all sensitive to glyphosate, but hybrid F1 plants containing both constructs, either in tobacco pr *Arabidopsis*, exhibited glyphosate resistance.

Example 4

Splitting the *Arabidopsis* AHAS Gene

The acetolactate synthase (AHAS) gene from *Arabidopsis* (Genbank accession AY042819) was amplified from *Arabidopsis* genomic DNA using primers Als1 (5' taaaccatgg cggcggcaac aacaac 3') and Als2 (5' gactctagac cggtttcatc tctcagtatt taatc cggcc atctcc 3') and cloned as an Nco1-Xba1 fragment in Icon Genetics binary vector plCBV24 (Kan', selection in *E coli* and *Agrobacterium*). Ser653 was mutated to Asn by PCR using primers Alsm5 (5' caggacaagt ctctcgtcgt atg 3'), Als4 (5' gaaagtgcca ccattcggga tcatcg 3'), Als3 (5' cgatgatccc gaatggtggc ac 3') and Als2. The amplified mutated fragment was cloned as an Nhe1-Age1 fragment. A second amino acid, Pro197 was mutated to Ser by PCR using primers Als1, Alsm5, Alsm6 (5' acgacgagag acttgtcctg tg 3') and Alspr1. The amplified mutated fragment was subcloned as a Sapl-Mlul fragment.

The rice actin1 promoter was amplified by PCR from rice genomic DNA using primers Actpr1 (5' atgggcgcgc cagatct-gca tgccggtcga ggtcattcat atgcttgag 3') and Actpr2 (5' cgc-catggtt tatcgatagc ttatcgtcta cctacaaaaa agctccgcac g 3'). The PCR product was cloned upstream of the AHAS gene as an Ascl-Nco1 fragment. The resulting plasmid, plCH12590 (FIG. 16) contains the rice actin1 promoter followed by the *Arabidopsis* AHAS coding sequence with two mutated amino acids, and the Nos terminator.

The mutated Ahas gene was split into two parts using the *Synechocystis* sp. PCC6803 DnaE intein. To test a position for splitting AHAS, amino acids RAEELLK (amino acids 428 to 434) were replaced by amino acids DVKAYCFNKKG using PCR with primers Alsm5, Alsm4 (5' ggccatggtt aaaacaatat tccgcaaact tgacgtcgtt ctcaagaacc ttattcatcc 3'), Alsm3 (5' gcg-gaatatt gattaacca tggccttgat tttggagttt ggagg 3') and Nosterrev (5' tcatcgcaag accggcaaca gg 3'). This substitution results in a protein that is similar to the protein that would be produced by intein-mediated trans-splicing of the constructs described below (plCH12610 and plCH12650, see FIG. 17). The mutated fragment was subcloned as a BspE1-Scat fragment. The resulting plasmid, plCH12600 (FIG. 16), was tested for AHAS activity by bombardment of *Triticum monococcum* cell suspension cultures and selection on plates containing 0.5 to 3 microMolar sulfometuron methyl (Sigma).

The intein-N part of the DnaE intein was amplified by PCR from *Synechocystis* genomic DNA with primers IntN1 (5' gcaagcttga cgtcaagttt gcggaatatt gcctcagt 3') and IntN3 (5' cgtctagagt cgacctgcag ttatttaatt gtcccagcgt caag 3'), and subcloned into plCH12600 (FIG. 16) as a Aat2-Xba1 fragment. The resulting plasmid, plCH12610 (FIG. 17), contains the N part of the AHAS gene fused to the intein-N fragment.

A PCR fragment containing the intein-C part of the DnaE intein was amplified from *Synechocystis* genomic DNA with primers Ctintei (5' ggtctagaatcgatggttaaagttatcggtcgtcg 3') and IntC2 (5' cgccatggtt aaaacaattg gcggcgatcg c 3'). A PCR fragment containing an artificial chloroplast targeting signal (sequence: massmlssaa vvatrasaaq asmvapftgl ksaasfpvtr kqnrilditsi asnggrvqca) was amplified from plCH5300 with primers Spr3 (5' cgcacaatcc cactatcctt cg 3') and Ctinte2 (5' ctttaaccat agcgcattga actcttcctc c 3'). A fragment, containing a fusion chloroplast targeting signal-intein-C fragment was obtained by amplification from both fragments with primers Spr3 and IntC2. This fragment was cloned using Cla1 and Nco1 into plCH12600 (FIG. 16). The resulting plasmid plCH12660 contains the fusion artificial chloroplast targeting signal-DnaE intein C-AHAS C fragment under control of the rice actin1 promoter, in a binary vector. To test the functionality of the split AHAS gene, plCH12610 and plCH12650 (FIG. 17) were co-bombarded into *Triticum monococcum* cell suspension cultures and the cells selected on media containing 0.5 to 3 microMolar sulfometuron methyl.

Example 5

Splitting the BARNASE Gene

The barnase gene was split using the *Synechocystis* sp. PCC6803 DnaB intein. DNA fragments for the N and C terminal parts of Barnase flanked by appropriate restriction sites were chemically synthesized by a commercial DNA-synthesis company.

The sequence of the N terminal end is:
5' gcaatcgatg gcacaggtta tcaacacgtt tgacggggtt gcggattatc ttcagacata tcataagcta cctgataatt acattacaaa atcagaagca caagccctcg gctgggacgt ccgc 3'

The sequence of the C terminal end is:
5' cgccatgggg tggcatcaaa agggaacctt gcagacgtcg ctccggggaa aagcatcggc ggagacatct tctcaaacag ggaaggcaaa ctcccgggca aaagcggacg aacatggcgt gaagcggata ttaactatac atcaggcttc agaaattcag accggattct ttactcaagc gactggctga tttacaaaac aacggaccat tatcagacct ttacaaaaat cagataagga tccgc 3'.

The N terminal end of Barnase was fused to the N part of the DnaB intein. The DnaB intein-N fragment was amplified from Synechocystis DNA using primers DnaBintNpr1 (5' gtAAGCTTGA CGTcagagag agtggatgca tcagtggaga tag 3') and DnaBintNpr2 (5' caCTGCAGct ataattgtaa agaggagctt tctag 3'). The Barnase fragment (a Cla1 Aatll fragment) and the intein fragment (a Aatll Pstl fragment) were cloned in an Icon Genetics binary vector resulting in clone plCH12790.

The C terminal end of Barnase was fused to the C part of the DnaB intein. The DnaB intein-C fragment was amplified from Synechocystis DNA using primers dnaBintCprl (gt CTG CAG ATC GAT TCA TGA gcc cag aaa tag aaa agt tgt ctc) and dnaBintCpr2 (tc AAG CTT CCA TGG tct tgc tct tca ctg tta tgg aca atg atg tca t). The intein fragment (a Sac1 Nco1 fragment) and the Barnase fragment (a Nco1 BamHI fragment) were cloned in an Icon Genetics binary vector, resulting in clone plCH12820.

Functionality of the N and C terminal Barnase-intein fusion clones was tested by agroinfiltration of Nicotiana benthamiana leaves. As expected the infiltrated sector became necrotic.

To reduce activity of Barnase, a frameshift was introduced in the N part of the Barnase gene. A PCR was performed on plCH12790 with primers Barnpr4 (5' gcaatcgatg gcacaggtta ttcaacacgt ttgac 3') that contains the frameshift, and Barnpr5 (5' gcggacgtcc cagccgaggg cttgtgc 3') and subcloned in plCH12790 resulting in plasmid plCH12800. The tapetum-specific promoter (Genbank Number D21160; Tsuchia et al., 1994, *Plant Mol. Biol.*, 26, 1737-1746) was amplified from rice genomic DNA using primers Tapp1 (5' cggaattcgg cgc-cittllt ttacacagtt caaagtgaat tttgg 3') and Tappr2 (5' cgcatcgatg cttaattagc tttggttaat tggag 3') and subcloned in plCH12800 as an EcoRI-Cla1 fragment, resulting in plasmid plCH12830 (FIG. 18). The rice tapetum-specific promoter was subcloned from plCH12830 (FIG. 18) into plCH12820 as an EcoR1-Cla1 fragment. The resulting construct plCH12840 (FIG. 18) contains the intein-CBamase-C fusion under control of the rice tapetum-specific promoter.

Example 6

Generation of Pro-Locus_Constructs

Assembly of all components required in the final construct was done in a stepwise fashion. First a sequence containing an AttP and an AttB site flanked by appropriate restriction sites was made from overlapping oligonucleotides and cloned in the Icon Genetics binary vector plCBV26 (only contains Xhol-Clal-Xbal sites between T-DNA borders, Kan' selection in *E. coli* and *Agrobacterium*). The resulting sequence (ag-atctgtgc cccaactggg gtaacctttg agttctctc agttgggggc gtagg-gaatt ctgtctgcag tctagattta tgcatggcgc gcctatctcg agctcgaagc cgcggtgcgg gtgccagggc gtgcccttgg gctccccggg cgcgtactcc acctcaccca tcactagttg tggtaccatc gcagggccc) is present in construct plCH12920. The N-terminal Barnase-intein fragment (EcoRl-Pstl fragment from plCH12830, FIG. 18), the Ahas-intein fragment (Asc1 Xho1 fragment from plCH 12610, FIG. 17), and the Ocs terminator (an Xbal Pstl fragment from plCH12900) were subcloned in plCH12920. The resulting clone plCH12950 (FIG. 19) contains both NI-terminal Bar-nase and Ahas fragments flanked by AttP and AttB sites in binary vector.

Next, a sequence containing an AttP site flanked by appropriate restriction sites was made from overlapping oligo-nucleotides and cloned in piCBV26. The resulting construct plCBV12850 contains the sequence (ggtacctgca gtattctaga ttcgaattct cgagtgtggc gcgccgtgcc ccaactgggg taaccttga gttctctcag ttgggggcgt agggccct) on the T-DNA. The C-termi-nal inteinBarnase fragment (an EcoRI-BamHI fragment from plCH12840, FIG. 18), the Ocs terminator (a BamHI-Pstl fragment from plCH12900) and the C-terminal intein-Ahas fragment (an Ascl Xhol fragment from plCH12650) were subcloned in plCH12850. The resulting clone plCH12910 (FIG. 19) contains both C-terminal Barnase and Ahas fragments and an AttP site in binary vector.

C-terminal and N-terminal fragments were combined in one binary vector by subcloning a Kpnl Apal fragment from plCH12910 into plCH12950 (FIG. 19), resulting in plCH12960 (FIG. 21).

Selectable Marker for Transformation:

A HPT gene under control of the maize ubiquitin promoter was used for plant transformation. To facilitate selection, an intron was inserted into HPT coding sequence. First a target site for cloning was inserted into the HPT coding sequence by amplifying a PCR fragment from plCO52 (HPT coding sequence-Nos terminator in pUC19) with overlapping primers Bamhpt (5' cgggatccaa tcagatatga aaaagcctga ac 3'), Hptint1 (5' ccacaactgt ggtctcaagg tgcttgacat tggggagttc ag 3'), Hptint2 (5' ggatatcggt ctcgtacctc cggaatcggg agcgcgg 3'), Sgfhpt (5' cgcagcgatc gcatccattg cctccgcgac cggctggaga acagcg 3'), and Inttarg (5' aggtacgaga ccgatatcca caactgtggt ctcaaggt 3'), and subcloning the amplified fragment as a BamHI Sgfl fragment into plCO52. An intron was amplified from petunia genomic DNA with primers Intpet3 (5' gtctg-gtctc aggtaagttc tgcatttggt tatgctcctt gcattt 3') and Intpet4 (5' gtctggtctc tacctgtagc aataattaaa acaaaaata 3') and cloned as a Bsa1 fragment in the plasmid described above, resulting in plasmid plCH12710. The maize ubiquitin promoter was amplified by PCR from genomic DNA using primers Ubi1 (5' ttgcatgcct gcagt gcagc gtgacccggt c 3') and Ubi2 (5' gggatc-ctct agagtcgacc tgcagaagta acaccaaaca acagggtg 3') and cloned as a Sph1-BamHI fragment together with HPT (a BamHI Xba1 fragment from plCH12710) in plCH12720 (an intermediate construct containing restriction sites and an AttB site; sequence 5' tctaagctac tcgagactag tgcatgctgt tcta-gactcg aagccgcggt gcggtgcca gggcgtgccc ttgggctccc cgggcgcgta ctccacctca cccatcggta ccg 3'). The resulting construct plCH12870 (FIG. 20) contains the hygromycin gene with an intron fused to the maize ubiquitin promoter, followed by an AttB site.

Finally, the HPT gene was subcloned as a Kpn1-Spe1 fragment into plCH12960 (FIG. 21). The resulting construct plCH12970 (FIG. 21) contains the N and C-terminal ends of Ahas and Barnase fused to intein fragments as well as the HPT selection marker, two AttP sites and two AttB sites.

Example 7

Constructing Integrase Clones plCH13160 (FIG. 20) was made by cloning the Streptomy-ces Phage C31 integrase (From David Ow, Plant Gene Expression Center, US Department of Agriculture—Agricultural Research Service, Albany, Calif. 94710, USA) and the Spm promoter (amplified by PCR from plCO28 with primers Spmprfwd (5' cgtctagagt caaaggagtg tcagttaatt a 3') and Spm-prrev (5' cgctgcagtg cttggcgagg ccgccc 3') in an Icon Genetics binary vector (selection in *agrobacterium* and *E. coli*: Kan$^R$).

The maize ubiquitin promoter was subcloned from plCH12720 as a BspD1-blunt Pst1 fragment into plCH13160 (FIG. 20) digested with Ascl-blunt and Pst1. The resulting plasmid, plCH13130 (FIG. 20) contains the integrase under control of the maize ubiquitin promoter.

Example 8

Generation of Transgenic Plants with Pro-Locus

The plCH12970 (FIG. 21), plCH13130 (FIG. 20) and plCH13160 (FIG. 20) constructs were transformed into maize, rice and tobacco using Hygromycin selection.

plCH12970 transformants were sprayed with chlorsulfuron (GLEAN, Dupont) to select plants that expressed the mutant split AHAS gene at a level sufficient for herbicide resistance (alternatively, construct plCH12960 (FIG. 21) can be transformed into plants using selection on chlorsulfuron or sulfometuron methyl, with the advantage of directly selecting transformants that express AHAS at a sufficient level). Plants that looked healthy despite the presence of the split Barnase gene, but that were male sterile, were analyzed by Southern blot to identify individuals containing a single transgene. Such transformants were pollinated by plCH13130 (FIG. 20) or plCH13160 (FIG. 20) transformants. The same transformants were also pollinated with wild type plants to rescue plants with an intact non-recombined transgene locus. The F1 plants (plCH12970 x integrase transformants) were checked by PCR for the presence of both transgenes (plCH12970 transgene, see FIG. 21, and the integrase, see FIG. 20), and seeds were collected. The F2 seedlings were grown and screened by PCR to detect recombinants that lacked either the N-terminal or the C-terminal parts of the split Barnase and Ahas genes. Such plants were completely fertile. Pairs of plants containing complementary parts of the construct (as a result of integrase-mediated recombination) were crossed. Seedlings obtained from these crosses were sprayed with chlorsulfuron to eliminate plants that did not contain both parts of the construct. All plants that were resistant to chlorsulfuron were also male sterile.

The following methods were used for penetrating transgenic plants:

Tobacco Transformation

The constructs were used for *Agrobacterium*-mediated leaf disc transformation of *Nicotiana tabacum* plants (Horsh et al., 1985, *Science*, 2271 1229-1231) using selection on Hygromycin (25-100 mg/I) or sulfometuron methyl (0.5-3.0 microM) or chlorsulfuron (0.2-5.0 microM).

Rice Transformation

Callus cultures were induced from mature and immature embryos of rice cvs. Pusa Basmati 1, Koshhikari etc.

The culture media were based on Chu (N6) salts and vitamins (Chu et al., Scientia Sinica, 18(5):659-68, 1975).

Callus induction and propagation medium was supplemented with 30 g/l sucrose, 600 mg/I Lproline, 2.0 mg/I of 2,4-D and 0.3% gelrite.

Pre-regeneration medium contained N6 salts and vitamins with 30 g/I sucrose, 1 mg/I NM, 2 mg/I BA, 2 mg/I ABA and 0.6% gelrite.

Regeneration medium contained N6 salts and vitamins with 30 g/I sucrose, 0.2 mg/I NAA, 2 mg/I BA, and 0.6% gelrite.

Infection medium (IM) contained N6 salts and vitamins with 2 mg/I 2,4-D, 10 g/I glucose, 60 g/l maltose, 50 mg/I ascorbic acid, 1 g/I MES (2-N-morpholinoethanesulfonic acid) and 40 mg/I Acetosyringone (AS). The pH of the medium was adjusted to 5.2 by 1 N KOH.

Cocultivation medium (CM) was same as the 1M (excluding ascorbic acid) and was solidified by adding 0.6% gelrite.

Infection medium was filter sterilized, whereas all other media were autoclaved. AS, dissolved in DMSO (400 mg/ml), was added after sterilization.

Agrobacterial cultures (strains AGL1, EHA105, LBA4404 etc.) with the appropriate binary plasmids were grown for 3 days at room temperature on LB2N (LB medium with 2 g/I NaCI and 1.5% agar) plates supplemented with the appropriate antibiotics. Bacteria were scraped from the plates and resuspended in the IM (10-20 ml) in 50-mL falcon tubes. The tubes were fixed horizontally to a shaker platform and shaken at low speed for 4 to 5 h at room temperature. Optical density of the bacterial suspension was measured and OD600 was adjusted to 1.0-2.0.

Callus pieces were incubated in the agrobacterial suspension for 20-180 min at room temperature, blotted on the filter paper disks and transferred to the gelrite-solidified CM with 60 g/I maltose. After 3-6 days of cultivation on the CM the calli were washed five times by sterile water and transferred to the gelrite-solidified CM with 60 g/l sucrose and appropriate selective agent and, if needed, 150 mg/I Timentin.

Resistant calli developed under selection were plated to the pre-regeneration medium with appropriate selective agent. Two weeks later the cultures were transferred to the regeneration medium with appropriate selective agent. Regenerated plantlets were grown on half-strength N6 medium without hormones for one month before transplanting into the soil.

Hygromycin B, for hpt (hygromycin phosphotransferase) gene-based selection, was used at concentrations 25-100 mg/I. Selection based on the herbicide-resistant forms of AHAS (Acetohydroxy acid synthase) gene was performed on sulfometuron methyl (0.5-3.0 microM) or chlorsulfuron (0.2-5.0 microM).

Maize Transformation

Maize immature embryos and callus cultures obtained from the lines A188, Hill etc. were transformed essentially in the same way as rice cultures. Most of the media and transformation steps were the same. Pre-regeneration medium was not used. Regeneration medium contained N6 salts and vitamins, 30 WI sucrose, 2 mg/I Zeatin and 0.05 mg/l 2,4-D. Silver thiosulfate was included in the regeneration medium at concentrations 0.01-0.06 mM.

That which is claimed:

1. A process of producing transgenic multi-cellular plants or parts thereof expressing a trait (1) and a trait (2) of interest, wherein said process comprises
   (i) producing a first plant having in a first locus of a nuclear chromosome a first heterologous nucleotide sequence comprising: a first fragment of a nucleotide sequence conferring trait (1) and a first fragment of a nucleotide sequence conferring trait (2);
   (ii) producing a second plant having in a second locus of a nuclear chromosome homologous to said nuclear chromosome of step (i), a second heterologous nucleotide sequence comprising a second fragment of a nucleotide sequence conferring trait (1) and a second fragment of a nucleotide sequence conferring trait (2);
   (iii) hybridising said first and said second plant to generate progeny exhibiting said functional trait (1) due to intein-mediated trans-splicing between a protein or polypeptide encoded by said first fragment of a nucleotide sequence conferring trait (1) and a protein or polypeptide encoded by said second fragment of a nucleotide sequence conferring trait (1); and exhibiting said functional trait (2) due to intein-mediated trans-splicing between a protein or polypeptide encoded by said first fragment of a nucleotide sequence conferring trait (2) and a protein or polypeptide encoded by said second fragment of a nucleotide sequence conferring trait (2); and
   (iv) selecting progeny that exhibits said trait (2) by applying a herbicide to said progeny, whereby said trait (1) endows resistance against said herbicide.

2. The process of claim 1, wherein trait (2) is female or male sterility.

3. The process of claim 2, wherein trait (2) is male sterility, and wherein said first heterologous nucleotide sequence comprises in operable linkage a first promoter, and a first fragment of a sequence comprising a male sterility gene linked to a 5' intein coding sequence, and wherein said second heterologous nucleotide sequence comprises in operable linkage a second promoter, and a 3' intein coding sequence linked to a second fragment of a sequence comprising a male sterility gene.

4. The process of claim 3, wherein said first promoter and/or said second promoter is a tapetum-specific promoter, and wherein said male sterility gene is barnase.

5. The process of claim 2, wherein step (iv) involves selecting progeny that exhibits male sterility as said trait (2) by applying a herbicide to said progeny, whereby said trait (1) endows resistance against said herbicide.

6. The process of claim 1, wherein step (i) comprises introducing said first heterologous nucleotide sequences into said first locus of a nuclear chromosome of a plant or a plant cell by site-targeted integration into a pre-engineered integration site or by homologous recombination.

7. The process of claim 1, wherein step (ii) comprises introducing said second heterologous nucleotide sequences into said second locus of a nuclear chromosome of a plant or a plant cell by site-targeted integration into a pre-engineered integration site or by homologous recombination.

8. The process of claim 1, wherein steps (i) and (ii) are carried out by
   (a) introducing a parent heterologous nucleotide sequence comprising said first and said second heterologous nucleotide sequences into a nuclear chromosome of parent plants or cells thereof;
   (b) optionally selecting plants or cells thereof having said parent heterologous nucleotide sequence integrated in a desired chromosome or chromosome locus;
   (c) subsequently splitting said parent heterologous nucleotide sequence so that said first and said second heterologous nucleotide sequences are located on homologous chromosomes in different plants or cells.

9. The process of claim 8, wherein step (c) comprises excision of said first or of said second heterologous nucleotide sequence from said parent heterologous nucleotide sequence, optionally followed by reintegration of said excised first or said excised second heterologous nucleotide sequence into a locus of a chromosome that is homologous with respect to the chromosome of said parent heterologous nucleotide sequence.

10. The process of claim 9, wherein said first and/or said second heterologous nucleotide sequence in said parent heterologous nucleotide sequence is/are contained in a non-autonomous transposon and said excision comprises providing a transposase for said transposon.

11. The process of claim 9, wherein said first heterologous nucleotide sequence in said parent heterologous nucleotide sequence is flanked by recombination sites of a first site-specific recombinase and
   wherein said second heterologous nucleotide sequence in said parent heterologous nucleotide sequence is flanked by recombination sites of a second site specific recombinase.

12. The process of claim 9, wherein said first heterologous nucleotide sequence in said parent heterologous nucleotide sequence is flanked by differing recombination sites of a site-specific integrase, and said second heterologous nucleotide sequence in said parent heterologous nucleotide sequence is flanked by differing recombination sites of the same site-specific integrase, and step (c) is carried out by
   providing said site-specific integrase to said parent plant or cells thereof,
   selecting progeny of said parent plant or cells thereof containing said first heterologous nucleotide sequence but not said second heterologous nucleotide sequence, and
   selecting progeny of said parent plant or cells thereof containing said second heterologous nucleotide sequence but not said first heterologous nucleotide sequence.

13. The process of claim 1, wherein said first and said second loci are corresponding loci on homologous chromosomes.

14. The process of claim 1, wherein said first and said second plant are made homozygous for said first and said second heterologous nucleotide sequences.

15. The process of claim 1, wherein trait (1) and trait (2) have a controlled distribution of said traits to progeny, said controlled distribution means that, upon crossing of said transgenic multi-cellular plant with a plant devoid of said first and said second heterologous sequences, the frequency of the appearance of said traits in descendent plants is less than 1%.

16. The process of claim 15, wherein said transgenic multi-cellular plant is incapable of expressing said trait of interest in the absence of either said first or said second heterologous nucleotide sequence.

17. A transgenic plant, a seed or a plant cell each expressing a trait (1) and a trait (2) of interest and comprising:
   (i) in a first locus of a nuclear chromosome a first heterologous nucleotide sequence comprising: a first fragment of a nucleotide sequence conferring a trait (1) and a first fragment of a nucleotide sequence conferring trait (2); and
   (ii) in a second locus of a nuclear chromosome homologous to item (i), a second heterologous nucleotide sequence comprising: a second fragment of a nucleotide sequence conferring a trait (1) and a second fragment of a nucleotide sequence conferring trait (2);
   said plant, seed, or plant cells exhibiting:
   said trait (1) due to intein-mediated trans-splicing between a protein or polypeptide encoded by said first fragment of a nucleotide sequence conferring trait (1) and a protein or polypeptide encoded by said second fragment of a nucleotide sequence conferring trait (1); and
   said trait (2) due to intein-mediated trans-splicing between a protein or polypeptide encoded by said first fragment of a nucleotide sequence conferring trait (2) and a protein or polypeptide encoded by said second fragment of a nucleotide sequence conferring trait (2);
   trait (1) being herbicide resistance and trait (2) being male sterility.

18. The plant of claim 17, wherein said first heterologous nucleotide sequence comprises in operable linkage a first promoter, and a first fragment of a sequence comprising a male sterility gene linked to a 5' intein coding sequence, and wherein said second heterologous nucleotide sequence comprises in operable linkage a second promoter, and a 3' intein coding sequence linked to a second fragment of a sequence comprising a male sterility gene.

19. The plant of claim 18, wherein said first promoter and/or said second promoter is a tapetum-specific promoter, and wherein said male sterility gene is barnase.

20. A process of producing hybrid seeds, comprising
   (i) producing a transgenic multi-cellular plant expressing two traits of interest, trait (1) being herbicide resistance and trait (2) being male sterility; according to the process of claim 5;
   (ii) crossing said transgenic multi-cellular plant with another plant that is male fertile; and optionally
   (iii) harvesting seeds growing on said transgenic multi-cellular plant separately from seeds growing on said plant that is male fertile.

21. Hybrid seeds obtained from the process of claim 20 or plants grown therefrom; wherein said seeds comprise at least one of said heterologous nucleotide sequences.

22. The process of claim 20, wherein said first locus and said second locus are corresponding loci on homologous chromosomes.

23. Hybrid seeds obtained from the process of claim 22 or plants grown therefrom.

* * * * *

SEQUENCE LISTING

<160> NUMBER OF SEQ ID NOS: 61

<210> SEQ ID NO 1
<211> LENGTH: 22
<212> TYPE: DNA
<213> ORGANISM: Artificial Sequence
<220> FEATURE:
<223> OTHER INFORMATION: PCR primer

<400> SEQUENCE: 1
cgcacaatcc cactatcctt cg                                          22

<210> SEQ ID NO 2

```
<211> LENGTH: 22
<212> TYPE: DNA
<213> ORGANISM: Artificial Sequence
<220> FEATURE:
<223> OTHER INFORMATION: PCR primer

<400> SEQUENCE: 2
ctgcttgtcg gccatgatat ag                                              22

<210> SEQ ID NO 3
<211> LENGTH: 46
<212> TYPE: DNA
<213> ORGANISM: Artificial Sequence
<220> FEATURE:
<223> OTHER INFORMATION: PCR primer

<400> SEQUENCE: 3
ctatatcatg gccgacaagc agaagtttgc ggaatattgc ctcagt                    46

<210> SEQ ID NO 4
<211> LENGTH: 33
<212> TYPE: DNA
<213> ORGANISM: Artificial Sequence
<220> FEATURE:
<223> OTHER INFORMATION: PCR primer

<400> SEQUENCE: 4
tttggatcct tatttaattg tcccagcgtc aag                                  33

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
aagaacggca tcaaggtgaa c                                               21

<210> SEQ ID NO 6
<211> LENGTH: 22
<212> TYPE: DNA
<213> ORGANISM: Artificial Sequence
<220> FEATURE:
<223> OTHER INFORMATION: PCR primer

<400> SEQUENCE: 6
tcatcgcaag accggcaaca gg                                              22

<210> SEQ ID NO 7
<211> LENGTH: 27
<212> TYPE: DNA
<213> ORGANISM: Artificial Sequence
<220> FEATURE:
<223> OTHER INFORMATION: PCR primer

<400> SEQUENCE: 7
tttccatggt taaagttatc ggtcgtc                                         27

<210> SEQ ID NO 8
<211> LENGTH: 45
<212> TYPE: DNA
<213> ORGANISM: Artificial Sequence
<220> FEATURE:
<223> OTHER INFORMATION: PCR primer

<400> SEQUENCE: 8
```

```
gttcaccttg atgccgttct tacaattggc ggcgatcgcc ccatt        45
```

<210> SEQ ID NO 9
<211> LENGTH: 27
<212> TYPE: DNA
<213> ORGANISM: Artificial Sequence
<220> FEATURE:
<223> OTHER INFORMATION: PCR primer

<400> SEQUENCE: 9

```
tctccatgga atccctgacg ttacaac        27
```

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10

```
acctggagag tgatactgtt g        21
```

<210> SEQ ID NO 11
<211> LENGTH: 45
<212> TYPE: DNA
<213> ORGANISM: Artificial Sequence
<220> FEATURE:
<223> OTHER INFORMATION: PCR primer

<400> SEQUENCE: 11

```
caacagtatc actctccagg taagtttgcg gaatattgcc tcagt        45
```

<210> SEQ ID NO 12
<211> LENGTH: 60
<212> TYPE: PRT
<213> ORGANISM: Artificial Sequence
<220> FEATURE:
<223> OTHER INFORMATION: transit peptide (example 2)

<400> SEQUENCE: 12

Met Ala Ser Ser Met Leu Ser Ser Ala Ala Val Val Ala Thr Arg Ala
1               5                   10                  15

Ser Ala Ala Gln Ala Ser Met Val Ala Pro Phe Thr Gly Leu Lys Ser
            20                  25                  30

Ala Ala Ser Phe Pro Val Thr Arg Lys Gln Asn Asn Leu Asp Ile Thr
        35                  40                  45

Ser Ile Ala Ser Asn Gly Gly Arg Val Gln Cys Ala
    50                  55                  60

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13

```
cgctatctgg tcgagggcga t        21
```

<210> SEQ ID NO 14
<211> LENGTH: 29
<212> TYPE: DNA
<213> ORGANISM: Artificial Sequence
<220> FEATURE:
<223> OTHER INFORMATION: PCR Primer

```
<400> SEQUENCE: 14
cggggatcct taggcaggcg tactcattc                                         29

<210> SEQ ID NO 15
<211> LENGTH: 48
<212> TYPE: DNA
<213> ORGANISM: Artificial Sequence
<220> FEATURE:
<223> OTHER INFORMATION: PCR Primer

<400> SEQUENCE: 15
atcgccctcg accagatagc gggatttgtt aaaacaattg gcggcgat                    48

<210> SEQ ID NO 16
<211> LENGTH: 50
<212> TYPE: DNA
<213> ORGANISM: Artificial Sequence
<220> FEATURE:
<223> OTHER INFORMATION: PCR Primer

<400> SEQUENCE: 16
caacagtatc actctccagg ttttgcggaa tatgccctca gttttggcac                  50

<210> SEQ ID NO 17
<211> LENGTH: 52
<212> TYPE: DNA
<213> ORGANISM: Artificial Sequence
<220> FEATURE:
<223> OTHER INFORMATION: PCR Primer

<400> SEQUENCE: 17
atcgccctcg accagatagc ggttaaaagc agcggcggcg atcgccccat tg               52

<210> SEQ ID NO 18
<211> LENGTH: 26
<212> TYPE: DNA
<213> ORGANISM: Artificial Sequence
<220> FEATURE:
<223> OTHER INFORMATION: PCR Primer

<400> SEQUENCE: 18
taaaccatgg cggcggcaac aacaac                                            26

<210> SEQ ID NO 19
<211> LENGTH: 46
<212> TYPE: DNA
<213> ORGANISM: Artificial Sequence
<220> FEATURE:
<223> OTHER INFORMATION: PCR Primer

<400> SEQUENCE: 19
gactctagac cggtttcatc tctcagtatt taatccggcc atctcc                      46

<210> SEQ ID NO 20
<211> LENGTH: 23
<212> TYPE: DNA
<213> ORGANISM: Artificial Sequence
<220> FEATURE:
<223> OTHER INFORMATION: PCR Primer

<400> SEQUENCE: 20
caggacaagt ctctcgtcgt atg                                               23

<210> SEQ ID NO 21
<211> LENGTH: 26
<212> TYPE: DNA
```

```
<213> ORGANISM: Artificial Sequence
<220> FEATURE:
<223> OTHER INFORMATION: PCR Primer

<400> SEQUENCE: 21
gaaagtgcca ccattcggga tcatcg                                          26

<210> SEQ ID NO 22
<211> LENGTH: 22
<212> TYPE: DNA
<213> ORGANISM: Artificial Sequence
<220> FEATURE:
<223> OTHER INFORMATION: PCR Primer

<400> SEQUENCE: 22
cgatgatccc gaatggtggc ac                                              22

<210> SEQ ID NO 23
<211> LENGTH: 22
<212> TYPE: DNA
<213> ORGANISM: Artificial Sequence
<220> FEATURE:
<223> OTHER INFORMATION: PCR primer

<400> SEQUENCE: 23
acgacgagag acttgtcctg tg                                              22

<210> SEQ ID NO 24
<211> LENGTH: 49
<212> TYPE: DNA
<213> ORGANISM: Artificial Sequence
<220> FEATURE:
<223> OTHER INFORMATION: PCR Primer

<400> SEQUENCE: 24
atgggcgcgc cagatctgca tgccggtcga ggtcattcat atgcttgag                 49

<210> SEQ ID NO 25
<211> LENGTH: 50
<212> TYPE: DNA
<213> ORGANISM: Artificial Sequence
<220> FEATURE:
<223> OTHER INFORMATION: PCR Primer

<400> SEQUENCE: 25
cgccatggtt tatcgatagc ttatcgtcta cctacaaaaa agctccgcac                50

<210> SEQ ID NO 26
<211> LENGTH: 60
<212> TYPE: DNA
<213> ORGANISM: Artificial Sequence
<220> FEATURE:
<223> OTHER INFORMATION: PCR Primer

<400> SEQUENCE: 26
ggccatggtt aaacaatat tccgcaaact tgacgtcgtt ctcaagaacc ttattcatcc      60

<210> SEQ ID NO 27
<211> LENGTH: 45
<212> TYPE: DNA
<213> ORGANISM: Artificial Sequence
<220> FEATURE:
<223> OTHER INFORMATION: PCR Primer

<400> SEQUENCE: 27
gcggaatatt gttttaacca tggccttgat tttggagttt ggagg                     45
```

<210> SEQ ID NO 28
<211> LENGTH: 38
<212> TYPE: DNA
<213> ORGANISM: Artificial Sequence
<220> FEATURE:
<223> OTHER INFORMATION: PCR Primer

<400> SEQUENCE: 28
gcaagcttga cgtcaagttt gcggaatatt gcctcagt                    38

<210> SEQ ID NO 29
<211> LENGTH: 44
<212> TYPE: DNA
<213> ORGANISM: Artificial Sequence
<220> FEATURE:
<223> OTHER INFORMATION: PCR Primer

<400> SEQUENCE: 29
cgtctagagt cgacctgcag ttatttaatt gtcccagcgt caag             44

<210> SEQ ID NO 30
<211> LENGTH: 35
<212> TYPE: DNA
<213> ORGANISM: Artificial Sequence
<220> FEATURE:
<223> OTHER INFORMATION: PCR Primer

<400> SEQUENCE: 30
ggtctagaat cgatggttaa agttatcggt cgtcg                       35

<210> SEQ ID NO 31
<211> LENGTH: 31
<212> TYPE: DNA
<213> ORGANISM: Artificial Sequence
<220> FEATURE:
<223> OTHER INFORMATION: PCR Primer

<400> SEQUENCE: 31
cgccatggtt aaaacaattg gcggcgatcg c                           31

<210> SEQ ID NO 32
<211> LENGTH: 60
<212> TYPE: PRT
<213> ORGANISM: Artificial Sequence
<220> FEATURE:
<223> OTHER INFORMATION: artificial chloroplast targeting signal

<400> SEQUENCE: 32

Met Ala Ser Ser Met Leu Ser Ser Ala Ala Val Val Ala Thr Arg Ala
1               5                   10                  15

Ser Ala Ala Gln Ala Ser Met Val Ala Pro Phe Thr Gly Leu Lys Ser
            20                  25                  30

Ala Ala Ser Phe Pro Val Thr Arg Lys Gln Asn Asn Leu Asp Ile Thr
        35                  40                  45

Ser Ile Ala Ser Asn Gly Gly Arg Val Gln Cys Ala
    50                  55                  60

<210> SEQ ID NO 33
<211> LENGTH: 22
<212> TYPE: DNA
<213> ORGANISM: Artificial Sequence
<220> FEATURE:
<223> OTHER INFORMATION: PCR Primer

<400> SEQUENCE: 33
cgcacaatcc cactatcctt cg                                              22

<210> SEQ ID NO 34
<211> LENGTH: 31
<212> TYPE: DNA
<213> ORGANISM: Artificial Sequence
<220> FEATURE:
<223> OTHER INFORMATION: PCR Primer

<400> SEQUENCE: 34
ctttaaccat agcgcattga actcttcctc c                                    31

<210> SEQ ID NO 35
<211> LENGTH: 124
<212> TYPE: DNA
<213> ORGANISM: Artificial Sequence
<220> FEATURE:
<223> OTHER INFORMATION: N-terminal sequence of barnase flanked by
      restriction sites

<400> SEQUENCE: 35
gcaatcgatg gcacaggtta tcaacacgtt tgacggggtt gcggattatc ttcagacata     60
tcataagcta cctgataatt acattacaaa atcagaagca caagccctcg gctgggacgt    120
ccgc                                                                 124

<210> SEQ ID NO 36
<211> LENGTH: 245
<212> TYPE: DNA
<213> ORGANISM: Artificial Sequence
<220> FEATURE:
<223> OTHER INFORMATION: C-terminal sequence of barnase flanked by
      restriction sites

<400> SEQUENCE: 36
cgccatgggg tggcatcaaa agggaacctt gcagacgtcg ctccggggaa aagcatcggc     60
ggagacatct tctcaaacag ggaaggcaaa ctcccgggca aaagcggacg aacatggcgt    120
gaagcggata ttaactatac atcaggcttc agaaattcag accggattct ttactcaagc    180
gactggctga tttacaaaac aacggaccat tatcagacct tacaaaaat cagataagga     240 tccgc                                                                245

<210> SEQ ID NO 37
<211> LENGTH: 43
<212> TYPE: DNA
<213> ORGANISM: Artificial Sequence
<220> FEATURE:
<223> OTHER INFORMATION: PCR primer

<400> SEQUENCE: 37
gtaagcttga cgtcagagag agtggatgca tcagtggaga tag                       43

<210> SEQ ID NO 38
<211> LENGTH: 35
<212> TYPE: DNA
<213> ORGANISM: Artificial Sequence
<220> FEATURE:
<223> OTHER INFORMATION: PCR primer

<400> SEQUENCE: 38
cactgcagct ataattgtaa agaggagctt tctag                                35

<210> SEQ ID NO 39
<211> LENGTH: 44
<212> TYPE: DNA

<210> SEQ ID NO 39
<211> LENGTH: 44
<212> TYPE: DNA
<213> ORGANISM: Artificial Sequence
<220> FEATURE:
<223> OTHER INFORMATION: PCR primer

<400> SEQUENCE: 39
gtctgcagat cgattcatga gcccagaaat agaaaagttg tctc			44

<210> SEQ ID NO 40
<211> LENGTH: 48
<212> TYPE: DNA
<213> ORGANISM: Artificial Sequence
<220> FEATURE:
<223> OTHER INFORMATION: PCR primer

<400> SEQUENCE: 40
tcaagcttcc atggtcttgc tcttcactgt tatggacaat gatgtcat			48

<210> SEQ ID NO 41
<211> LENGTH: 35
<212> TYPE: DNA
<213> ORGANISM: Artificial Sequence
<220> FEATURE:
<223> OTHER INFORMATION: PCR primer

<400> SEQUENCE: 41
gcaatcgatg gcacaggtta ttcaacacgt ttgac			35

<210> SEQ ID NO 42
<211> LENGTH: 27
<212> TYPE: DNA
<213> ORGANISM: Artificial Sequence
<220> FEATURE:
<223> OTHER INFORMATION: PCR primer

<400> SEQUENCE: 42
gcggacgtcc cagccgaggg cttgtgc			27

<210> SEQ ID NO 43
<211> LENGTH: 45
<212> TYPE: DNA
<213> ORGANISM: Artificial Sequence
<220> FEATURE:
<223> OTHER INFORMATION: PCR primer

<400> SEQUENCE: 43
cggaattcgg cgcctttttt ttacacagtt caaagtgaat tttgg			45

<210> SEQ ID NO 44
<211> LENGTH: 35
<212> TYPE: DNA
<213> ORGANISM: Artificial Sequence
<220> FEATURE:
<223> OTHER INFORMATION: PCR primer

<400> SEQUENCE: 44
cgcatcgatg cttaattagc tttggttaat tggag			35

<210> SEQ ID NO 45
<211> LENGTH: 198
<212> TYPE: DNA
<213> ORGANISM: Artificial Sequence
<220> FEATURE:
<223> OTHER INFORMATION: resulting sequence present in construct
    pICH12920

<400> SEQUENCE: 45
agatctgtgc cccaactggg gtaacctttg agttctctca gttgggggcg tagggaattc			60 tgtctgcagt ctagatttat gcatggcgcg cctatctcga gctcgaagcc gcggtgcggg    120
tgccagggcg tgcccttggg ctccccgggc gcgtactcca cctcacccat cactagttgt    180
ggtaccatcg cagggccc                                                  198

<210> SEQ ID NO 46
<211> LENGTH: 98
<212> TYPE: DNA
<213> ORGANISM: Artificial Sequence
<220> FEATURE:
<223> OTHER INFORMATION: resulting sequence present in construct
      pICBV12850

<400> SEQUENCE: 46
ggtacctgca gtattctaga ttcgaattct cgagtgtggc gcgccgtgcc ccaactgggg    60
taacctttga gttctctcag ttggggggcgt agggccct                           98

<210> SEQ ID NO 47
<211> LENGTH: 32
<212> TYPE: DNA
<213> ORGANISM: Artificial Sequence
<220> FEATURE:
<223> OTHER INFORMATION: PCR primer

<400> SEQUENCE: 47
cgggatccaa tcagatatga aaaagcctga ac                                  32

<210> SEQ ID NO 48
<211> LENGTH: 42
<212> TYPE: DNA
<213> ORGANISM: Artificial Sequence
<220> FEATURE:
<223> OTHER INFORMATION: PCR primer

<400> SEQUENCE: 48
ccacaactgt ggtctcaagg tgcttgacat tggggagttc ag                       42

<210> SEQ ID NO 49
<211> LENGTH: 37
<212> TYPE: DNA
<213> ORGANISM: Artificial Sequence
<220> FEATURE:
<223> OTHER INFORMATION: PCR primer

<400> SEQUENCE: 49
ggatatcggt ctcgtacctc cggaatcggg agcgcgg                             37

<210> SEQ ID NO 50
<211> LENGTH: 46
<212> TYPE: DNA
<213> ORGANISM: Artificial Sequence
<220> FEATURE:
<223> OTHER INFORMATION: PCR primer

<400> SEQUENCE: 50
cgcagcgatc gcatccattg cctccgcgac cggctggaga acagcg                   46

<210> SEQ ID NO 51
<211> LENGTH: 37
<212> TYPE: DNA
<213> ORGANISM: Artificial Sequence
<220> FEATURE:
<223> OTHER INFORMATION: PCR primer

<400> SEQUENCE: 51

-continued

```
ggatatcggt ctcgtacctc cggaatcggg agcgcgg                              37
```

<210> SEQ ID NO 52
<211> LENGTH: 38
<212> TYPE: DNA
<213> ORGANISM: Artificial Sequence
<220> FEATURE:
<223> OTHER INFORMATION: PCR primer

<400> SEQUENCE: 52

```
aggtacgaga ccgatatcca caactgtggt ctcaaggt                             38
```

<210> SEQ ID NO 53
<211> LENGTH: 46
<212> TYPE: DNA
<213> ORGANISM: Artificial Sequence
<220> FEATURE:
<223> OTHER INFORMATION: PCR primer

<400> SEQUENCE: 53

```
gtctggtctc aggtaagttc tgcatttggt tatgctcctt gcattt                    46
```

<210> SEQ ID NO 54
<211> LENGTH: 39
<212> TYPE: DNA
<213> ORGANISM: Artificial Sequence
<220> FEATURE:
<223> OTHER INFORMATION: PCR primer

<400> SEQUENCE: 54

```
gtctggtctc tacctgtagc aataattaaa acaaaaata                            39
```

<210> SEQ ID NO 55
<211> LENGTH: 31
<212> TYPE: DNA
<213> ORGANISM: Artificial Sequence
<220> FEATURE:
<223> OTHER INFORMATION: PCR primer

<400> SEQUENCE: 55

```
ttgcatgcct gcagtgcagc gtgacccggt c                                    31
```

<210> SEQ ID NO 56
<211> LENGTH: 48
<212> TYPE: DNA
<213> ORGANISM: Artificial Sequence
<220> FEATURE:
<223> OTHER INFORMATION: PCR primer

<400> SEQUENCE: 56

```
gggatcctct agagtcgacc tgcagaagta acaccaaaca acagggtg                  48
```

<210> SEQ ID NO 57
<211> LENGTH: 113
<212> TYPE: DNA
<213> ORGANISM: Artificial Sequence
<220> FEATURE:
<223> OTHER INFORMATION: sequence cloned in pICH12720 to obtain
      pICH12870

<400> SEQUENCE: 57

```
tctaagctac tcgagactag tgcatgctgt tctagactcg aagccgcggt gcgggtgcca     60
gggcgtgccc ttgggctccc cgggcgcgta ctccacctca cccatcggta ccg           113
```

<210> SEQ ID NO 58
<211> LENGTH: 31

```
<212> TYPE: DNA
<213> ORGANISM: Artificial Sequence
<220> FEATURE:
<223> OTHER INFORMATION: PCR primer

<400> SEQUENCE: 58
cgtctagagt caaaggagtg tcagttaatt a                                    31

<210> SEQ ID NO 59
<211> LENGTH: 26
<212> TYPE: DNA
<213> ORGANISM: Artificial Sequence
<220> FEATURE:
<223> OTHER INFORMATION: PCR primer

<400> SEQUENCE: 59
cgctgcagtg cttggcgagg ccgccc                                          26

<210> SEQ ID NO 60
<211> LENGTH: 10
<212> TYPE: PRT
<213> ORGANISM: Artificial Sequence
<220> FEATURE:
<223> OTHER INFORMATION: ten additional amino acids of EPSP gene product

<400> SEQUENCE: 60

Lys Phe Ala Glu Tyr Cys Phe Asn Lys Ser
1               5                   10

<210> SEQ ID NO 61
<211> LENGTH: 11
<212> TYPE: PRT
<213> ORGANISM: Artificial Sequence
<220> FEATURE:
<223> OTHER INFORMATION: replaced amino acids in 428-414 for splitting
      AHAS

<400> SEQUENCE: 61

Asp Val Lys Ala Tyr Cys Phe Asn Lys Lys Gly
1               5                   10
```